United States Patent
Gomelsky et al.

(10) Patent No.: US 10,041,057 B2
(45) Date of Patent: Aug. 7, 2018

(54) NEAR-INFRARED LIGHT-ACTIVATED PROTEINS

(71) Applicant: University of Wyoming, Laramie, WY (US)

(72) Inventors: Mark Gomelsky, Laramie, WY (US); Min-Hyung Ryu, Laramie, WY (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 15/000,896

(22) Filed: Jan. 19, 2016

(65) Prior Publication Data

US 2017/0081652 A1    Mar. 23, 2017

Related U.S. Application Data

(63) Continuation-in-part of application No. 14/326,778, filed on Jul. 9, 2014, which is a continuation-in-part (Continued)

(51) Int. Cl.
  *C12N 9/00*  (2006.01)
  *C12N 15/62*  (2006.01)
  (Continued)

(52) U.S. Cl.
  CPC .............. *C12N 9/88* (2013.01); *A61K 31/711* (2013.01); *A61K 31/713* (2013.01);
  (Continued)

(58) Field of Classification Search
  None
  See application file for complete search history.

(56) References Cited

U.S. PATENT DOCUMENTS 6,858,429 B2    2/2005  Quail
8,835,399 B2    9/2014  Gomelsky et al.
(Continued)

FOREIGN PATENT DOCUMENTS

WO    WO 2009/151948    12/2012

OTHER PUBLICATIONS

Iseki et al., A blue-light-activated adenylyl cyclase mediates photoavoidance in Euglena gracilis. Nature, 2002, 415:1047-1051.*
(Continued)

*Primary Examiner* — Kevin K Hill
*Assistant Examiner* — Arthur S Leonard
(74) *Attorney, Agent, or Firm* — Leydig, Voit & Mayer, Ltd.

(57) ABSTRACT

Methods and constructs are provided for controlling processes in live animals, plants or microbes via genetically engineered near-infrared light-activated or light-inactivated proteins including chimeras including the photosensory modules of bacteriohytochromes and output modules that possess enzymatic activity and/or ability to bind to DNA, RNA, protein, or small molecules. DNA encoding these proteins are introduced as genes into live animals, plants or microbes, where their activities can be turned on by near-infrared light, controlled by the intensity of light, and turned off by near-infrared light of a different wavelength than the activating light. These proteins can regulate diverse cellular processes with high spatial and temporal precision, in a nontoxic manner, often using external light sources. For example, near-infrared light-activated proteins possessing nucleotidyl cyclase, protein kinase, protease, DNA-binding and RNA-binding activities are useful to control signal transduction, cell apoptosis, proliferation, adhesion, differentiation and other cell processes.

15 Claims, 23 Drawing Sheets

Related U.S. Application Data of application No. 13/560,645, filed on Jul. 27, 2012, now Pat. No. 8,835,399.

(60) Provisional application No. 61/512,065, filed on Jul. 27, 2011.

(51) Int. Cl.
| | |
|---|---|
| *A61K 48/00* | (2006.01) |
| *A61N 5/00* | (2006.01) |
| *G01N 33/52* | (2006.01) |
| *C12N 9/88* | (2006.01) |
| *C07K 14/195* | (2006.01) |
| *A61K 38/16* | (2006.01) |
| *A61K 38/51* | (2006.01) |
| *A61K 41/00* | (2006.01) |
| *A61N 5/06* | (2006.01) |
| *A61K 31/711* | (2006.01) |
| *A61K 31/713* | (2006.01) |
| *C07K 7/06* | (2006.01) |
| *C12N 9/50* | (2006.01) |
| *C12N 9/64* | (2006.01) |
| *G01N 33/50* | (2006.01) |

(52) U.S. Cl.
CPC ............ *A61K 38/164* (2013.01); *A61K 38/51* (2013.01); *A61K 41/00* (2013.01); *A61N 5/062* (2013.01); *C07K 7/06* (2013.01); *C07K 14/195* (2013.01); *C12N 9/50* (2013.01); *C12N 9/6472* (2013.01); *C12N 9/6475* (2013.01); *C12N 15/62* (2013.01); *C12Y 114/14* (2013.01); *C12Y 304/22056* (2013.01); *C12Y 406/01001* (2013.01); *C12Y 406/01002* (2013.01); *G01N 33/5023* (2013.01); *G01N 33/5088* (2013.01); *A61K 48/00* (2013.01); *A61N 2005/0659* (2013.01); *C07K 2319/00* (2013.01); *C07K 2319/60* (2013.01)

(56) References Cited

U.S. PATENT DOCUMENTS

| | | |
|---|---|---|
| 2006/0110827 A1 | 5/2006 | Lagarias et al. |
| 2010/0093051 A1 | 4/2010 | Kehoe |
| 2015/0013024 A1 | 1/2015 | Gomelsky et al. |

OTHER PUBLICATIONS

NCBI gene Accession No. Q76L34, Photoactivated adenylate cyclase subunit alpha, (May 10, 2017, pp. 1-3).*
Sharrock et al. (2008) "The phytochrome red/far-red photoreceptor superfamily," Genome Biol. 9:230. pp. 1-7.
Office Action corresponding to U.S. Appl. No. 14/326,778, dated Mar. 24, 2017.
Adam E, Hussong A. Bindics J, Wust F, Viczian A, Essing M, Medzihradszky M, Kircher S, Schafer E, Nagy F (2011) Altered dark- and photoconversion of Phyto-chrome B mediate extreme light sensitivity and loss of photoreversibility of the phyB-401 mutant. PLoS ONE 6, e27250.
Adamantidis AR, Zhang F, Aravanis AM, Deisseroth K and de Lecea L. (2007). "Neural substrates of awakening probed with optogenetic control of hypocretin neurons." Nature 450: 420-424.
Airan, RD, Thompson KR, Fenno LE, Bernstein H, Deisseroth K. (2009). "Temporally precise in vivo control of intracellular signaling." Nature 458: 1025-1029.
Arai, R. et ai.,Conformations of variably linked chimeric proteins evaluated by synchrotron X-ray small-angle scattering. Proteins. Dec. 1, 2004;57(4):829-38.
Arai, R. et al., "Design of the linkers which effectively separate domains of a bifunctional fusion protein" Protein Engineering, vol. 14, No. 8, pp. 529-532 (2001).
Arnold K, Bordoli L, Kopp J, Schwede T (2006) The Swiss-Model Workspace: A web-based environment for protein structure homology modelling. Bioinformatics 22, 195-201.
Auldridge ME, Forest K T (2011) Bacterial phyto-chromes: more than meets the light. Crit Rev Biochem Mol Biot 46, 67-88.
Barends, T.R.M., E. Hartmann, J. Griese, N.V. Kirienko, D.A. Ryjenkov, J. Reinstein, R.L. Shoeman, M. Gomelsky, I. Schlichting. (2009). "Structure and mechanism of a light-regulated cyclic nucleotide phosphodiesterase." Nature 459: 1015-1018.
Barends et al. "Structure and mechanism of a bacterial light-regulated cyclic nucleotide phosphodiesterase" Nature vol. 459, pp. 1015-1020 (2009).
Bellini D, Papiz M Z (2012) Structure of a bacteria-phytochrome and light-stimulated protomer swapping with a gene repressor. Structure 20:1436-46.
Benkert P, Biasini M, Schwede T (2011) Toward the estimation of the absolute quality of individual protein structure models. Bioinformatics 27, 343-50.
Bhoo, S-H, Davis, SJ, Walker, J., Karniol B, Vierstra R. (2001). "Bacteriophytochromes are photochromic histidine kinases using a biliverdin chromophore". Nature 414: 776-779.
Bruder, S., J.U. Linder, S.E. Martinez, N. Zheng, J.A. Beavo, and J.E. Schultz. (2005). "The cyanobacterial tandem GAF domains from the CyaB2 adenylyl cyclase signal via both cAMP-binding sites." Proc Natl Acad Sci U S A.102:3088-92.
Bulina ME, Chudakov OM, Britanova OV, Yanushevich YG, Staroverov DB, Chepurnykh TV, Merzlyak EM, Shkrob MA, Lukyanov S, Lukyanov KA. (2006) "A genetically encoded photosensitizer." Nat Biotechnol 24: 95-9.
Busby S, Ebright R H (1999) Transcription activation by catabolite activator protein (CAP). J Mol Biof 293, 199-213.
Byrnes KR, Waynant RW, Ilev IK, Wu X, Barna L, Smith K, Heckert R, Gerst H, Anders JJ. (2005). "Light promotes regeneration and functional recovery and alters the immune response after spinal cord injury." Lasers Surg Med. 36:171-85.
Cardin JA, Carlen M, Meletis K, Knoblich U, Zhang F, Deisseroth K, Tsai LH and Moore CI. (2009). "Driving fast-spiking cells induces gamma rhythm and controls sensory responses." Nature 459: 663-667.
Chin, K V, Yang W L, Ravatn R, Kita T, Reitman E, Vettori D, Cvijic ME, Shin M, Iacono L (2002) Reinvent-ing the wheel of cyclic AMP novel mechanisms of cAMP signaling. Ann NY Acad Sci 968, 49-64.
Cho M-H, Yoo Y, Bhoo S-H, Lee, S-W. Feb. 12, 2011. "Purification and Characterization of a Recombinant Bacteriophytochrome of Xanthomonas oryzae pathovar oryzae." Protein J (2011) 30:124-131.
Cole C, Barber J D, Barton G J (2008) The Jpred 3 secondary structure prediction server. Nucl Acids Res 36. W197-W201.
Crawford ED and Wells JA. (2011). "Caspase substrates and cellular remodeling." Annu Rev Biochemistry 80:1055-1087.
Cubeddu R, Pifferi A, Taroni P, Torricelli A, Valentini G. (1999) "Noninvasive absorption and scattering spectroscopy of bulk diffusive media: An application to the optical characterization of human breast." Appl Phys Lett 74:874-6.
Davis M W, Somerville D, Lee R Y, Lockery S, AveryL, Fambrough D M (1995) Mutations in theCae-norhabditis elegans Na,K-ATPase alpha-subunit gene, eat-6, disrupt excitable cell function. J Neurosci 15, 8408-18.
De N, Nevarro MV, Raghavan RV, Sondermann H. (2009) "Determinants for the Activation and Autoinhibition of the Diguanylate Cyclase Response Regulator WspR." J. Mol. Bioi. 393: 619-633.
De N, Pirruccello M, Krasteva PV, Bae N, Raghavan RV, Sondermann H. (2008) "Phosphorylation-independent regulation of the diguanylate cyclase WspR." PLoS Bioi 6, e67.
Desmet KD, Paz DA, Cory JJ, Eells JT, Wong-Riley MT, Henry MM, Buchmann EV, Connelly MP, Dovi JV, Liang HL, Henshel OS, Yeager RL, Millsap OS, Lim J, Gould LJ, Das R, Jett M, Hodgson BD, Margolis D, Whelan HT. (2006) "Clinical and experimental applications of NIR-LED photobiomodulation." Photomed Laser Surg 24:121-128.

(56) References Cited

OTHER PUBLICATIONS

Edgar R C (2004) Muscle: multiple sequence alignment with high accuracy and high throughput. Nuci Acids Res 32, 1792-7.

Edwards S L, Charlie N K, Milfort M C, Brown B S, Gravlin C N, Knecht J E, Miller K G (2008) A novel molecular solution for ultraviolet light detection in Cae-norhabditis elegans. PLoS Biol6, e198.

Efetova M Petereit L, Rosiewicz K, Overend G, Hau ig F, Hovemann B T, Cabrera P, Dow J A, Schwarze!M (2013) Separate roles of PKA and EPAC in renal func-tion unraveled by the optogenetic control of cAMP levels in vivo. J Cell Sci 126, 778-788.

EP Supplemental Search report for application No. 12817578.3 dated May 13, 2015, 10 pages.

Fang Q, Carp SA, Selb J, Boverman G, Zhang Q, Kopans DB, Moore RH, Miller EL, Brooks DH, Boas DA. (2009). "Combined optical imaging and mammography of the healthy breast: optical contrast derived from breast structure and compression." IEEE Trans Med Imaging 28:30-42.

Gambetta G A, Lagarias J C (2001) Genetic engi-neering of phytochrome biosynthesis in bacteria. Proc Nat! Acad Sci USA 98, 10566-71.

Gasser C, Taiber S, Yeh C, Wittig C H, Hegemann P, Ryu S, Wunder F, Moglich A. (2014) Engineering of a red-light-activated human cAMPlcGMP-specific phos-phodesterase. Proc Natl Acad Sci USA 111, 8803-8.

Georgianna WE, Deiters A. (2010) "Reversible light switching of cell signalling by genetically encoded protein dimerization." Chembiochem 11:301-3.

Gomelsky, M and HoffWH. (2011) "Light helps bacteria make important lifestyle decisions." Trends Microbial 19:441-8.

Gradinaru V, Magri M, Thompson KR, Henderson JM and Deis-seroth K. (2009) "Optical deconstruction of parkinsonian neural circuitry." Science 324:354-359.

Gradinaru V, Zhang F, Ramakrishnan C, Mattis J, Prakash R, Diester I, Goshen I, Thompson KR, Deisseroth K. (2010) "Molecu-lar and cellular approaches for diversifying and extending optogenetics." Cell 141:154-65.

Hayashi H, Cuddy M, Shu VC, Yip KW, Madiraju C, Diaz P, Matsuyama T, Kaibara M, Taniyama K, Vasile S, Sergienko E, Reed JC. (2009) "Versatile assays for high throughput screening for activators or inhibitors of intracellular proteases and their cellular regulators." PLoS One 4, e7655.

Hockberger P E, Skimina T A, Centonze V E, Lavin C. Chu S, Dadras S, Reddy J K, White J G (1999) Activa-tion of flavin-containing oxidases underlies light-induced production of H2O2 in mammalian cells. Proc Nat Acad Sci USA 96, 6255-60.

Iseki M, Matsunaga S, Murakami A, Ohno K, Shiga K, Yoshida K, Sugai M, Takahashi T, Hori T, Watanabe M. (2002) "A blue-light-activated adenylyl cyclase mediates photoavoidance in Euglena gracilis." Nature. 415:1047-51.

Jacobson K, Rajfur Z, Vitriol E and Klaus H. "Chromophore-assisted laser inactivation in cell biology." Trends Cell Biology 18:434-450.

Kanacher T, Schultz A, Linder J U, Schultz J E (2002) A GAP-domain-regulated adenylyl cyclase from Anabaena is a self-activat-ing cAMP switch. EMBO J 21, 3672-80.

Kuzin A, Chen Y, Seetharaman J, Mao M, Xiao R, Ciccosanti C, Foote EL, Wang H, Everett JK, Nair R, Acton TB, Rost B, Montelione GT, Tong L, Hunt JF. (2009) "X-Ray Structure of Protein (EAL/GGDEF domain protein) from M. capsulatus", North-east Structural Genomics Consortium Target McR174C. PDB 3ICL.

Lamparter et al. Phtochrome from Agrobacterium tumef aciens has unusual spectral properties and reveaIls an N-terminal chromophore attachment site. PNAS, 2002, 99:11628-11633.

Landry Y, Niederhoffer N, Sick E, Gies JP. Heptahelical and other Gprotein-coupled receptors (GPCRs) signaling. Curr Med Chern (2006), 13:51-63.

Leung DW, Otomo C, Chory J, Rosen MK. (2008) "Genetically encoded photoswitching of actin assembly through the Cdc42-WASP-Arp2/3 complex pathway." Proc Natl Acad Sci USA. 105:12797-802.

Levskaya A, Chevalier AA, Tabor JJ, Simpson ZB, Lavery LA, Levy M, Davidson EA. Scouras A, Ellington AD, Marcotte EM, Voigt CA. (2005) "Synthetic biology: engineering *Escherichia coli* to see light." Nature 438: 441-442.

Levskaya A, Weiner OD, Lim WA, Voigt CA. (2009) "Spatiotemporal control of cell signalling using a light-switchable protein interaction." Nature 461:997-1001.

Li P, Gao X-G, Arellano RO, Renugopalakrishnan V. (2001) "Glycosylated and Phosphorylated Proteins-Expression in Yeast and Oocytes of Xenopus: Prospects and Challenges-Relevance to Expression of Thermostable Proteins." Protein Expression and Purification, 22:369-380.

Linder J U (2006) Class III adenylyl cyclases: molecular mecha-nisms of catalysis and regulation. Cell Mol Life Sci 63, 1736-51.

Liu X and Tonegawa S. (2010) "Optogenetics 3.0". Cell 141:22-24.

Losi et al. "Bacterial bilin- and flavin-binding photoreceptors", Photochem. Photobiol. Sci., (2008), 7:1168-1178.

Mackenzie S H and Clay C. (2008) "Targeting cell death in tumors by activating caspases." Curr Cancer Drg Targets 8:190-209.

Maheshwari SC, Khurana JP, Sopory SK. (1999) "Novel light-activated protein kinases as key regulators of plant growth and development." J. Biosci. 24 No. 4 49-514.

Miesenbock G. "The optogenetic catechism." (2009) Science 326:395-9.

Mills E, Chen X, Pham E, Wong SS, and Truong K. (2012) "Engineering a photoactivated caspase-7 for rapid induction of apoptosis." ACS Synthetic Biol 3:75-82.

Moglich A, Ayers RA, Moffat K. (2009) "Design and signaling mechanism of light-regulated histidine kinases." J Mol Bioi 385:1433-44.

Moglich A, Moffat K. (Sep. 2010) "Engineered photoreceptors as novel optogenetic tools." Photochemical and Photobiological Sci-ences, 9:1286-1300.

Moglich A, Yang X, Ayers RA, Moffat K. (2010) "Structure and function of plant photoreceptors." Annu Rev Plant Bioi 61:21-47.

Muller K, Weber W (2013) Optogenetic tools for mammalian systems. Mol BioSyst 9, 596-608.

Noak et al., Protein Conformational Changes of Agro bacterium Phytochrome Agp 1 during Chromophore Assembly and Photoconversion. Biochem, 2007, 46:4164-4176.

Pathak G P, Vrana J D, Tucker C L (2013) Optoge-netic control of cell function using engineered photorecep-tors. Biol Cell 105, 59-72.

Pei J, Grishin NV. (2001) GGDEF domain is homologous to adenylyl cyclase. Proteins. 42:210-216.

Piatkevich K D, Subach F V, Verkhusha VV (2013) Engineering of bacterial phylochromes for near-infrared imaging, sensing, and light-control in mammals. Chern Soc Rev 42, 3441-52.

Pop C., Feeney, A. Tripathy, and A. C. Clark. (2003) "Mutations in the procaspase-3 dimer interface affect the activity of the zymogen." Biochemistry, 42:12311-12320.

Punta M, Coggill PC, Eberhardt R Y, Mistry J, Tate J, Boursnell C, Pang N, Forslund K, Ceric G, Clements J, Heger A, Holm L, Sonnhammer E L, Eddy S R, Bateman A, Finn R D (2012) The Pfam protein families database. Nucl Acids Res 40 (Database issue), D290-301.

Rockwell NC, Su YS, Lagarias JC. (2006) "Phytochrome structure and signaling mechanisms." Annu Rev Plant Bioi. 57:837-858.

Romling U, Galperin MY, Gomelsky M (2013) Cyclic di-GMP: the first 25 years of a universal bacterial second messenger. Microbial Mol Biol Rev 77, 1-52.

Ryjenkov, D.A., M. Tarutina, O.V. Moskvin and M. Gomelsky. (2005) "Cyclic diguanylate is a ubiquitous signaling molecule in bacteria: Insights into the biochemistry of the GGDEF protein domain." J Bacterial 187:1792-1798.

Ryu M.-H. et al. "Engineering adenylate cyclases regulated by near-infrared windo light" PNAS, vol. 111 (28): 10167-10172 (2014).

(56) References Cited

OTHER PUBLICATIONS

Ryu, M.-H. et al., "Near-infrared Light Responsive Synthetic c-di-GMP Module for Optogenetic applications" ACS Synth. Biol. (2014) 3:802-810.

Ryu, M.-H., O.V. Moskvin, J Siltberg-Liberles, and M. Gomelsky. (2011) "Natural and engineered photoactivated nucleotidyl cyclases for optogenetic applications." J Biol Chem Oct. 28, 2010 [Epub ahead of print].

Ryu, Min-Hyung et al. (2010) "Natural and Engineered Photoactivated Nucleotidyl Cyclases for Optogenetic Applications" J. of Bio. Chem., 285(53):41501-41508.

Schade MA, Reynolds N K, Dollins C M, Miller K G (2005) Mutations that rescue the paralysis of Cae-norhabditis elegans ric-8 (synembryn) mutants activate the G alpha(s) pathway and define a third major branch of the synaptic signaling network. Genetics 169, 631-49.

Schirmer T, Jenal U. (2009) "Structural and mechanistic determinants of c-di-GMP signalling." Nat Rev Microbial 7:724-735.

Schroder-Lang S, Schwarze!M, Seifert R. StrOnker T, Kateriya S, Looser J, Watanabe M, Kaupp U B, Hege-mann P, Nagel G (2007) Fast manipulation of cellular cAMP level by light in vivo. Nat Methods 4, 39-42.

Serezani CH, Ballinger MN, Aronoff DM, Peters-Golden M. (2008) "Cyclic AMP: master regulator of innate immune cell function." Am J Respir Cell Mol Bioi. 39:127-32.

Shu X, Royant A, Lin MZ, Aguilera TA, Lev-Ram Varda, Steinbach PA, Tsien RY. (2009) "Mammalian expression of infrared fluorescent proteins engineered from a bacterial phytochrome." Science 324:804-7.

Sinha SC, Sprang SR. (2006) "Structures, mechanism, regulation and evolution of class III nucleotidyl cyclases." Rev Physiol Biochem Pharmacol 157:105-140.

Sjulson Land Miesenbock G. (2008) "Photocontrol of neural activity: Biophysical mechanisms and performance in vivo." Chem. Rev 108, 1588-1602.

Sohal VS, Zhang F, Yizhar O and Deisseroth K. (2009) "Parvalbumin neurons and gamma rhythms enhance cortical circuit performance." Nature 459:698-702.

Sorokina O, Kapus A, Terecske K, Dixon LE, Kozma-Bognar L, Nagy F, and Millar AJ. (2009) "A switchable light-input, light-output system modelled and constructed in yeast." Journal of Biological Engineering, 3:15.

Stierl M, Stumpf P, Udwari D, Gueta R, Hagedorn R, Losi A, Gartner W, Petereit L, Efetova M, Schwarzel M, Oertner TG, Nagel G, Hegemann P. "Light modulation of cellular cAMP by a small bacterial photoactivated adenylyl cyclase, bPAC, of the soil bacterium Beggiatoa." J Biol Chem. 2011, 286:1181-8.

Stinchcomb D T, Shaw J E, Carr S H, Hirsh D (1985) Extrachromosomal DNA transformation of Caenorhabdi-tis elegans. Mol Cell Biol 5, 3484-96.

Strickland D, Moffat K, Sosnick TR. (2008) "Light-activated DNA binding in a designed allosteric protein." Proc Natl Acad Sci USA 105:10709-10714.

Takala H, Bjorling A, Berntsson 0, Lehtivuori H, Niebling S, Hoernke M, Kosheleva I, Henning R, Menzel A, Ihalainen J A, Westenhoff S (2014) Signal amplification and transduction in phytochrome photosensors. Nature 509, 245-8.

Tarutina, M., Ryjenkov, D.A., and Gomelsky, M. (2006) "An unorthodox bacteriophytochrome from Rhodobacter sphaeroides involved in turnover of the second messenger c-di-GMP." J Biol Chem 281:34751-34758.

Toettcher JE, Voigt CA, Weiner OD, and Lim WA. (2011) "The promise of optogenetics in cell biology: interrogating molecular circuits in space and time." Nature Methods 8:35-38.

Tonnesen J, Sorensen AT, Deisseroth K, Lundberg C and Kokaia M. (2009) "Optogenetic control of epileptiform activity." Proc Natl Acad Sci USA 106:12162-12167.

Topal H, Fulcher N B, Bitterman J, Salazar E, Buck J, LevinLR, CannMJ, WolfgangMC, SteegbornC(2012) Crystal structure and regulation mechanisms of the CyaB adenylyl cyclase from the human pathogen *Pseudomonas aeruginosa*. J Mol Biol 416, 271-86.

Tsai HC, Zhang F, Adamantidis A, Stuber GD, Bonci A, de Lecea L, and Deisseroth K. (2009) "Phasic firing in dopaminergic neurons is sufficient for behavioral conditioning." Science 324:1080-1084.

Tyszkiewicz AB, Muir TW. (2008) "Activation of protein splicing with light in yeast." Nature Methods 5:303-305.

UlijaszA T, Vierstra RD (2011) Phytochrome structure and photochemistry: recent advances toward a com-plete molecular picture. Curr Opin Plant Bio114, 498-506.

Vera, Aris A, Daura X, Martinez MA, Villaverde A. (2005) "Engineering the *E. coli* beta-galactosidase for the screening of antiviral protease inhibitors." Biochem Biophys Res Commun 329:453-6.

Vuillet L, Kojadinovic M, Zappa S, Jaubert M, Adriano J.M., Fardoux JI, Hannibal L, Pignol D, Vermeglio A, Giraud E. (2007) "Evolution of a bacteriophytochrome from light to redox sensor." EMBO Journal, 26:3322-3331.

Walters J, Pop C, Scott FL. Drag M, Swartz P, Mattos C, Salvesen GS, Clark AC. (2009) "A constitutively active and uninhibitable caspase-3 zymogen efficiently induces apoptosis." Biochem J 424:335-45.

Wan S, Parrish JA, Anderson RR, Madden M. (1981) Transmittance of nonionizing radiation in human tissues. Photochem Photobiol 34:679-81.

Weissleder R. (2001) "A clearer vision for in vivo imaging." Nature Biotechnol 19:316-7.

Weissenberger S, Schultheis C, Liewald J F, Erb-guth K, Nagel G, Gottschalk A (2011) PACalpha-an optogenetic tool for in vivo manipulation of cellular cAMP levels, neurotransmitter release, and behavior in Cae-norhabditis elegans. J Neurochem 116, 616-25.

Wu Yi, Frey D, Lungu O., Jaehrig A, Schlichting I, Kuhlman B, Hahn KM. (2009) "A genetically encoded photoactivatable Rac controls the motility of living cells." Nature 461:104-108.

Yang X, Kuk J, Moffat K. (2008) "Crystal structure of *Pseudomonas aeruginosa* bacteriophytochrome: photoconversion and signal transduction." Proc Natl Acad Sci USA 105:14715-14720.

Yang X, Kuk J, Moffat K. (2009) "Conformational differences between the Pfr and Pr states in *Pseudomonas aeruginosa* bacteriophytochrome." Proc Natl Acad Sci USA 106:15639-15644.

Yazawa M, Sadaghiani AM, Hsueh B, Dolmetsch RE. (2009) "Induction of protein-protein interactions in live cells using light." Nat Biotechnol 27:941-945.

Zahringer F. Lacanna E, Jenal U, Schirmer T, Boehm A (2013) Structure and signaling mechanism of a zinc-sensory diguanylate cyclase. Structure 21, 1149-57.

Zhang J, Stankey, R J, Vierstra R D (2013) Struc-ture-guided engineering of plant phytochrome B with altered photochemistry and light signaling. Plant Physiol 161, 1445-57.

Zimmer M. (2009) "GFP: from jellyfish to the Nobel prize and beyond." Chem Soc Rev 38:2823-2832.

USPTO, Office Action in U.S. Appl. No. 14/326,778 dated Jan. 25, 2018.

U.S. Appl. No. 14/326,778, filed Jul. 9, 2015.

\* cited by examiner

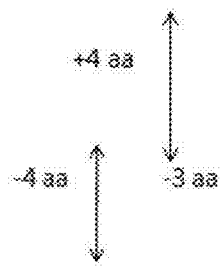

Near-infrared light-regulated adenylyl cyclases, IlaC

| | Construct | Fusion site | Activity IPTG, µM 5 50 |
|---|---|---|---|
| SEQ ID NO:1 | RlaC18 | MAQRTRAELAHLRHYDERKEVT | I + |
| SEQ ID NO:2 | RlaC29 | MAQRTRAELAHLR---ERKEVT | ~ A |
| SEQ ID NO:3 | RlaC28 | MAQRTRAELARL----ERKEVT | + + |
| SEQ ID NO:4 | RlaC34 | MAQRTRAELAR-----ERKEVT | ~ + |
| SEQ ID NO:5 | RlaC33 | MAQRTRAELA------ERKEVT | ~ + |
| SEQ ID NO:6 | RlaC17 | MAQRTRAEL-------ERKEVT | A + |
| SEQ ID NO:7 | RlaC20 | MAQRTRAE--------ERKEVT | ~ + |
| SEQ ID NO:8 | RlaC15 | MAQRTRA---------ERKEVT | ~ ~ |
| SEQ ID NO:9 | RlaC22 | MAQRTR----------ERKEVT | ~ A |
| SEQ ID NO:10 | RlaC25 | MAQRT-----------ERKEVT | ~ A |
| SEQ ID NO:11 | RlaC30 | MAQR------------ERKEVT | ~ ~ |
| SEQ ID NO:12 | RlaC26 | MAQ-------------ERKEVT | ~ ~ |
| SEQ ID NO:13 | RlaC27 | MA--------------ERKEVT | ~ ~ |
| | | PHY  Linker  AC | |

I, light-Inactivated
A, light-Activated
~, inactive
+, active

| | | 506 | 594 |
|---|---|---|---|
| SEQ ID NO: 46 | 0aa | DTLTGALGERLS ---------------------- | ERKEVTV |
| SEQ ID NO: 47 | +2aa | DTLTGALGERL RAE------------------ | ERKEVTV |
| SEQ ID NO: 48 | +3aa | DTLTGALGERL RAEL---------------- | ERKEVTV |
| SEQ ID NO: 49 | +10aa | DTLTGALGERL RAELARLRHYD | ERKEVTV |

| | | |
|---|---|---|
| SEQ ID NO: 50 | −1aa | DTLTGALGER ———————————— *ERKE VTVAFADLVGF* |
| SEQ ID NO: 51 | +4aa | DTLTGALGERL RAEL ————————— *ERKE VTVAFADLVGF* |
| SEQ ID NO: 52 | +5aa | DTLTGALGERL RAELA ———————— *ERKE VTVAFADLVGF* |
| SEQ ID NO: 53 | +8aa | DTLTGALGERL RAELARLR ———— *ERKE VTVAFADLVGF* |
| SEQ ID NO: 54 | +9aa | DTLTGALGERL RAELARLRA — *ERKE VTVAFADLVGF* |
| SEQ ID NO: 55 | +12aa | DTLTGALGERL RAELARLRAELA *ERKE VTVAFADLVGF* |

SEQUENCE LISTING

```
<160> NUMBER OF SEQ ID NOS: 55

<210> SEQ ID NO 1
<211> LENGTH: 22
<212> TYPE: PRT
<213> ORGANISM: Rhodobacter sphaeroides

<400> SEQUENCE: 1

Met Ala Gln Arg Thr Arg Ala Glu Leu Ala Arg Leu Arg His Tyr Asp
1               5                   10                  15

Glu Arg Lys Glu Val Thr
            20

<210> SEQ ID NO 2
<211> LENGTH: 19
<212> TYPE: PRT
<213> ORGANISM: Rhodobacter sphaeroides
```

-continued

```
<400> SEQUENCE: 2

Met Ala Gln Arg Thr Arg Ala Glu Leu Ala Arg Leu Arg Glu Arg Lys
1               5                   10                  15

Glu Val Thr

<210> SEQ ID NO 3
<211> LENGTH: 18
<212> TYPE: PRT
<213> ORGANISM: Rhodobacter sphaeroides

<400> SEQUENCE: 3

Met Ala Gln Arg Thr Arg Ala Glu Leu Ala Arg Leu Glu Arg Lys Glu
1               5                   10                  15

Val Thr

<210> SEQ ID NO 4
<211> LENGTH: 17
<212> TYPE: PRT
<213> ORGANISM: Rhodobacter sphaeroides

<400> SEQUENCE: 4

Met Ala Gln Arg Thr Arg Ala Glu Leu Ala Arg Glu Arg Lys Glu Val
1               5                   10                  15

Thr

<210> SEQ ID NO 5
<211> LENGTH: 16
<212> TYPE: PRT
<213> ORGANISM: Burkholderia sp.

<400> SEQUENCE: 5

Met Ala Gln Arg Thr Arg Ala Glu Leu Ala Glu Arg Lys Glu Val Thr
1               5                   10                  15

<210> SEQ ID NO 6
<211> LENGTH: 15
<212> TYPE: PRT
<213> ORGANISM: Prauserella rugosa

<400> SEQUENCE: 6

Met Ala Gln Arg Thr Arg Ala Glu Leu Glu Arg Lys Glu Val Thr
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Engineered peptide

<400> SEQUENCE: 7

Met Ala Gln Arg Thr Arg Ala Glu Glu Arg Lys Glu Val Thr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Engineered peptide

<400> SEQUENCE: 8

Met Ala Gln Arg Thr Arg Ala Glu Arg Lys Glu Val Thr
```

<210> SEQ ID NO 9
<211> LENGTH: 12
<212> TYPE: PRT
<213> ORGANISM: Artificial Sequence
<220> FEATURE:
<223> OTHER INFORMATION: Engineered peptide

<400> SEQUENCE: 9

Met Ala Gln Arg Thr Arg Glu Arg Lys Glu Val Thr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Engineered peptide

<400> SEQUENCE: 10

Met Ala Gln Arg Thr Glu Arg Lys Glu Val Thr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Engineered peptide

<400> SEQUENCE: 11

Met Ala Gln Arg Glu Arg Lys Glu Val Thr
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Engineered peptide

<400> SEQUENCE: 12

Met Ala Gln Glu Arg Lys Glu Val Thr
1               5

<210> SEQ ID NO 13
<211> LENGTH: 29
<212> TYPE: PRT
<213> ORGANISM: Rhodobacter sphaeroides

<400> SEQUENCE: 13

Ile Ala Ala Glu Met Ala Gln Arg Thr Arg Ala Glu Leu Ala Arg Leu
1               5                   10                  15

Arg His Tyr Asp Met Val Gly Glu Arg Lys Glu Val Thr
            20                  25

<210> SEQ ID NO 14
<211> LENGTH: 43
<212> TYPE: PRT
<213> ORGANISM: Artificial Sequence
<220> FEATURE:
<223> OTHER INFORMATION: Chimeric peptide

<400> SEQUENCE: 14

Ile Ala Ala Glu Met Ala Gln Arg Thr Arg Ala Glu Leu Ala Arg Leu

```
                1               5                  10                  15
Arg His Tyr Asp Pro Leu Thr Gly Ile Leu Ala Asn Leu Gly Glu Asp
            20                  25                  30

Ala Leu Met Val Gly Glu Arg Lys Glu Val Thr
            35                  40
```

<210> SEQ ID NO 15
<211> LENGTH: 42
<212> TYPE: PRT
<213> ORGANISM: Artificial Sequence
<220> FEATURE:
<223> OTHER INFORMATION: Chimeric peptide

<400> SEQUENCE: 15

```
Ile Ala Ala Glu Met Ala Gln Arg Thr Arg Ala Glu Leu Ala Arg Leu
1               5                   10                  15

Arg His Tyr Asp Pro Leu Thr Gly Ile Leu Ala Asn Gly Glu Asp Ala
            20                  25                  30

Leu Met Val Gly Glu Arg Lys Glu Val Thr
            35                  40
```

<210> SEQ ID NO 16
<211> LENGTH: 41
<212> TYPE: PRT
<213> ORGANISM: Artificial Sequence
<220> FEATURE:
<223> OTHER INFORMATION: Chimeric peptide

<400> SEQUENCE: 16

```
Ile Ala Ala Glu Met Ala Gln Arg Thr Arg Ala Glu Leu Ala Arg Leu
1               5                   10                  15

Arg His Tyr Asp Pro Leu Thr Gly Ile Leu Ala Asn Glu Asp Ala Leu
            20                  25                  30

Met Val Gly Glu Arg Lys Glu Val Thr
            35                  40
```

<210> SEQ ID NO 17
<211> LENGTH: 39
<212> TYPE: PRT
<213> ORGANISM: Artificial Sequence
<220> FEATURE:
<223> OTHER INFORMATION: Chimeric peptide

<400> SEQUENCE: 17

```
Ile Ala Ala Glu Met Ala Gln Arg Thr Arg Ala Glu Leu Ala Arg Leu
1               5                   10                  15

Arg His Tyr Asp Pro Leu Thr Gly Ile Leu Ala Asn Ala Leu Met Val
            20                  25                  30

Gly Glu Arg Lys Glu Val Thr
            35
```

<210> SEQ ID NO 18
<211> LENGTH: 34
<212> TYPE: PRT
<213> ORGANISM: Artificial Sequence
<220> FEATURE:
<223> OTHER INFORMATION: Chimeric peptide

<400> SEQUENCE: 18

```
Ile Ala Ala Glu Met Ala Gln Arg Thr Arg Ala Glu Leu Ala Arg Leu
1               5                   10                  15

Arg His Tyr Asp Pro Leu Thr Gly Ile Leu Ala Asn Glu Arg Lys Glu
```

Val Thr

<210> SEQ ID NO 19
<211> LENGTH: 29
<212> TYPE: PRT
<213> ORGANISM: Rhodobacter sphaeroides

<400> SEQUENCE: 19

Ile Ala Ala Glu Met Ala Gln Arg Thr Arg Ala Glu Leu Ala Arg Leu
1               5                   10                  15

Arg His Tyr Asp Met Val Gly Glu Arg Lys Glu Val Thr
            20                  25

<210> SEQ ID NO 20
<211> LENGTH: 26
<212> TYPE: PRT
<213> ORGANISM: Rhodobacter sphaeroides

<400> SEQUENCE: 20

Ile Ala Ala Glu Met Ala Gln Arg Thr Arg Ala Glu Leu Ala Arg Leu
1               5                   10                  15

Arg His Tyr Asp Glu Arg Lys Glu Val Thr
            20                  25

<210> SEQ ID NO 21
<211> LENGTH: 23
<212> TYPE: PRT
<213> ORGANISM: Rhodobacter sphaeroides

<400> SEQUENCE: 21

Ile Ala Ala Glu Met Ala Gln Arg Thr Arg Ala Glu Leu Ala Arg Leu
1               5                   10                  15

Arg Glu Arg Lys Glu Val Thr
            20

<210> SEQ ID NO 22
<211> LENGTH: 22
<212> TYPE: PRT
<213> ORGANISM: Rhodobacter sphaeroides

<400> SEQUENCE: 22

Ile Ala Ala Glu Met Ala Gln Arg Thr Arg Ala Glu Leu Ala Arg Leu
1               5                   10                  15

Glu Arg Lys Glu Val Thr
            20

<210> SEQ ID NO 23
<211> LENGTH: 21
<212> TYPE: PRT
<213> ORGANISM: Rhodobacter sphaeroides]

<400> SEQUENCE: 23

Ile Ala Ala Glu Met Ala Gln Arg Thr Arg Ala Glu Leu Ala Arg Glu
1               5                   10                  15

Arg Lys Glu Val Thr
            20

<210> SEQ ID NO 24
<211> LENGTH: 20
<212> TYPE: PRT
<213> ORGANISM: Rhodobacter sphaeroides

<400> SEQUENCE: 24

Ile Ala Ala Glu Met Ala Gln Arg Thr Arg Ala Glu Leu Ala Glu Arg
1               5                   10                  15

Lys Glu Val Thr
            20

<210> SEQ ID NO 25
<211> LENGTH: 19
<212> TYPE: PRT
<213> ORGANISM: Artificial Sequence
<220> FEATURE:
<223> OTHER INFORMATION: Engineered peptide

<400> SEQUENCE: 25

Ile Ala Ala Glu Met Ala Gln Arg Thr Arg Ala Glu Leu Glu Arg Lys
1               5                   10                  15

Glu Val Thr

<210> SEQ ID NO 26
<211> LENGTH: 18
<212> TYPE: PRT
<213> ORGANISM: Rhodobacter sphaeroides

<400> SEQUENCE: 26

Ile Ala Ala Glu Met Ala Gln Arg Thr Arg Ala Glu Glu Arg Lys Glu
1               5                   10                  15

Val Thr

<210> SEQ ID NO 27
<211> LENGTH: 17
<212> TYPE: PRT
<213> ORGANISM: Rhodobacter sphaeroides

<400> SEQUENCE: 27

Ile Ala Ala Glu Met Ala Gln Arg Thr Arg Ala Glu Arg Lys Glu Val
1               5                   10                  15

Thr

<210> SEQ ID NO 28
<211> LENGTH: 16
<212> TYPE: PRT
<213> ORGANISM: Rhodobacter sphaeroides

<400> SEQUENCE: 28

Ile Ala Ala Glu Met Ala Gln Arg Thr Arg Glu Arg Lys Glu Val Thr
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Engineered peptide

<400> SEQUENCE: 29

Ile Ala Ala Glu Met Ala Gln Arg Thr Glu Arg Lys Glu Val Thr
1               5                   10                  15

<210> SEQ ID NO 30
<211> LENGTH: 14
<212> TYPE: PRT
<213> ORGANISM: Artificial Sequence

```
<220> FEATURE:
<223> OTHER INFORMATION: Engineered peptide

<400> SEQUENCE: 30

Ile Ala Ala Glu Met Ala Gln Arg Glu Arg Lys Glu Val Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Engineered peptide

<400> SEQUENCE: 31

Ile Ala Ala Glu Met Ala Gln Glu Arg Lys Glu Val Thr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Engineered peptide

<400> SEQUENCE: 32

Ile Ala Ala Glu Met Ala Glu Arg Lys Glu Val Thr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Engineered peptide

<400> SEQUENCE: 33

Ile Ala Ala Glu Met Glu Arg Lys Glu Val Thr
1               5                   10

<210> SEQ ID NO 34
<211> LENGTH: 779
<212> TYPE: PRT
<213> ORGANISM: Artificial Sequence
<220> FEATURE:
<223> OTHER INFORMATION: Engineered protein

<400> SEQUENCE: 34

Met Ala Arg Gly Cys Leu Met Thr Ile Ser Gly Gly Thr Phe Asp Pro
1               5                   10                  15

Ser Ile Cys Glu Met Glu Pro Ile Ala Thr Pro Gly Ala Ile Gln Pro
                20                  25                  30

His Gly Ala Leu Met Thr Ala Arg Ala Asp Ser Gly Arg Val Ala His
            35                  40                  45

Ala Ser Val Asn Leu Gly Glu Ile Leu Gly Leu Pro Ala Ala Ser Val
        50                  55                  60

Leu Gly Ala Pro Ile Gly Glu Val Ile Gly Arg Val Asn Glu Ile Leu
65                  70                  75                  80

Leu Arg Glu Ala Arg Arg Ser Gly Ser Glu Thr Pro Glu Thr Ile Gly
                85                  90                  95

Ser Phe Arg Arg Ser Asp Gly Gln Leu Leu His Leu His Ala Phe Gln
                100                 105                 110

Ser Gly Asp Tyr Met Cys Leu Asp Ile Glu Pro Val Arg Asp Glu Asp
```

```
            115                 120                 125
Gly Arg Leu Pro Pro Gly Ala Arg Gln Ser Val Ile Glu Thr Phe Ser
130                 135                 140

Ser Ala Met Thr Gln Val Glu Leu Cys Glu Leu Ala Val His Gly Leu
145                 150                 155                 160

Gln Leu Val Met Gly Tyr Asp Arg Val Met Ala Tyr Arg Phe Gly Ala
                    165                 170                 175

Asp Gly His Gly Glu Val Ile Ala Glu Arg Arg Gln Asp Leu Glu
                180                 185                 190

Pro Tyr Leu Gly Leu His Tyr Pro Ala Ser Asp Ile Pro Gln Ile Ala
                195                 200                 205

Arg Ala Leu Tyr Leu Arg Gln Arg Val Gly Ala Ile Ala Asp Ala Cys
210                 215                 220

Tyr Arg Pro Val Pro Leu Leu Gly His Pro Glu Leu Asp Asp Gly Lys
225                 230                 235                 240

Pro Leu Asp Leu Thr His Ser Ser Leu Arg Ser Val Ser Pro Val His
                245                 250                 255

Leu Asp Tyr Met Gln Asn Met Asn Thr Ala Ala Ser Leu Thr Ile Gly
                260                 265                 270

Leu Ala Asp Gly Asp Arg Leu Trp Gly Met Leu Val Cys His Asn Thr
            275                 280                 285

Thr Pro Arg Ile Ala Gly Pro Glu Trp Arg Ala Ala Gly Met Ile
        290                 295                 300

Gly Gln Val Val Ser Leu Leu Ser Arg Leu Gly Glu Val Glu Asn
305                 310                 315                 320

Ala Ala Glu Thr Leu Ala Arg Gln Ser Thr Leu Ser Thr Leu Val Glu
                325                 330                 335

Arg Leu Ser Thr Gly Asp Thr Leu Ala Ala Ala Phe Val Ala Ala Asp
                340                 345                 350

Gln Leu Ile Leu Asp Leu Val Gly Ala Ser Ala Ala Val Val Arg Leu
                355                 360                 365

Ala Gly His Glu Leu His Phe Gly Arg Thr Pro Val Asp Ala Met
        370                 375                 380

Gln Lys Val Leu Asp Ser Leu Gly Arg Pro Ser Pro Leu Glu Val Leu
385                 390                 395                 400

Ser Leu Asp Asp Val Thr Leu Arg His Pro Glu Leu Pro Glu Leu Leu
                405                 410                 415

Ala Ala Gly Ser Gly Ile Leu Leu Pro Leu Thr Ser Gly Asp Gly
                420                 425                 430

Asp Leu Ile Ala Trp Phe Arg Pro Glu His Val Gln Thr Ile Thr Trp
            435                 440                 445

Gly Gly Asn Pro Ala Glu His Gly Thr Trp Asn Pro Ala Thr Gln Arg
        450                 455                 460

Met Arg Pro Arg Ala Ser Phe Asp Ala Trp Lys Glu Thr Val Thr Gly
465                 470                 475                 480

Arg Ser Leu Pro Trp Thr Ser Ala Glu Arg Asn Cys Ala Arg Glu Leu
                485                 490                 495

Gly Glu Ala Ile Ala Ala Glu Met Ala Gln Arg Thr Trp Glu Arg Lys
                500                 505                 510

Glu Val Thr Val Leu Phe Ser Asp Ile Arg Gly Tyr Thr Thr Leu Thr
            515                 520                 525

Glu Asn Leu Gly Ala Ala Glu Val Val Ser Leu Leu Asn Gln Tyr Phe
        530                 535                 540
```

```
Glu Thr Met Val Glu Ala Val Phe Asn Tyr Glu Gly Thr Leu Asp Lys
545                 550                 555                 560

Phe Ile Gly Asp Ala Leu Met Ala Val Phe Gly Ala Pro Leu Pro Leu
                565                 570                 575

Thr Glu Asn His Ala Trp Gln Ala Val Arg Ser Ala Leu Asp Met Arg
            580                 585                 590

Gln Arg Leu Lys Glu Phe Asn Gln Arg Ile Ile Gln Ala Gln Pro
        595                 600                 605

Gln Ile Lys Ile Gly Ile Gly Ile Ser Ser Gly Glu Val Val Ser Gly
    610                 615                 620

Asn Ile Gly Ser His Lys Arg Met Asp Tyr Thr Val Ile Gly Asp Gly
625                 630                 635                 640

Val Asn Leu Ser Ser Arg Leu Glu Thr Val Thr Lys Glu Tyr Gly Cys
                645                 650                 655

Asp Ile Ile Leu Ser Glu Phe Thr Tyr Gln Leu Cys Ser Asp Arg Ile
            660                 665                 670

Arg Val Arg Gln Leu Asp Lys Ile Arg Val Lys Gly Lys His Gln Ala
        675                 680                 685

Val Asn Ile Tyr Glu Leu Ile Ser Asp Arg Ser Thr Pro Leu Asp Asp
    690                 695                 700

Asn Thr Gln Glu Phe Leu Phe His Tyr His Asn Gly Arg Thr Ala Tyr
705                 710                 715                 720

Leu Val Arg Asp Phe Thr Gln Ala Ile Ala Cys Phe Asn Ser Ala Lys
                725                 730                 735

His Ile Arg Pro Thr Asp Gln Ala Val Asn Ile His Leu Glu Arg Ala
            740                 745                 750

Tyr Asn Tyr Gln Gln Thr Pro Pro Pro Gln Trp Asp Gly Val Trp
        755                 760                 765

Thr Ile Phe Thr Lys His His His His His His
    770                 775

<210> SEQ ID NO 35
<211> LENGTH: 508
<212> TYPE: PRT
<213> ORGANISM: Rhodobacter sphaeroides

<400> SEQUENCE: 35

Met Ala Arg Gly Cys Leu Met Thr Ile Ser Gly Gly Thr Phe Asp Pro
1               5                   10                  15

Ser Ile Cys Glu Met Glu Pro Ile Ala Thr Pro Gly Ala Ile Gln Pro
            20                  25                  30

His Gly Ala Leu Met Thr Ala Arg Ala Asp Ser Gly Arg Val Ala His
        35                  40                  45

Ala Ser Val Asn Leu Gly Glu Ile Leu Gly Leu Pro Ala Ala Ser Val
    50                  55                  60

Leu Gly Ala Pro Ile Gly Glu Val Ile Gly Arg Val Asn Glu Ile Leu
65                  70                  75                  80

Leu Arg Glu Ala Arg Arg Ser Gly Ser Glu Thr Pro Glu Thr Ile Gly
                85                  90                  95

Ser Phe Arg Arg Ser Asp Gly Gln Leu Leu His Leu His Ala Phe Gln
            100                 105                 110

Ser Gly Asp Tyr Met Cys Leu Asp Ile Glu Pro Val Arg Asp Glu Asp
        115                 120                 125

Gly Arg Leu Pro Pro Gly Ala Arg Gln Ser Val Ile Glu Thr Phe Ser
```

```
                130                 135                 140
Ser Ala Met Thr Gln Val Glu Leu Cys Glu Leu Ala Val His Gly Leu
145                 150                 155                 160

Gln Leu Val Leu Gly Tyr Asp Arg Val Met Ala Tyr Arg Phe Gly Ala
            165                 170                 175

Asp Gly His Gly Glu Val Ile Ala Glu Arg Arg Gln Asp Leu Glu
        180                 185                 190

Pro Tyr Leu Gly Leu His Tyr Pro Ala Ser Asp Ile Pro Gln Ile Ala
            195                 200                 205

Arg Ala Leu Tyr Leu Arg Gln Arg Val Gly Ala Ile Ala Asp Ala Cys
210                 215                 220

Tyr Arg Pro Val Pro Leu Leu Gly His Pro Glu Leu Asp Asp Gly Lys
225                 230                 235                 240

Pro Leu Asp Leu Thr His Ser Ser Leu Arg Ser Val Ser Pro Val His
            245                 250                 255

Leu Asp Tyr Met Gln Asn Met Asn Thr Ala Ala Ser Leu Thr Ile Gly
            260                 265                 270

Leu Ala Asp Gly Asp Arg Leu Trp Gly Met Leu Val Cys His Asn Thr
        275                 280                 285

Thr Pro Arg Ile Ala Gly Pro Glu Trp Arg Ala Ala Gly Met Ile
290                 295                 300

Gly Gln Val Val Ser Leu Leu Ser Arg Leu Gly Glu Val Glu Asn
305                 310                 315                 320

Ala Ala Glu Thr Leu Ala Arg Gln Ser Thr Leu Ser Thr Leu Val Glu
            325                 330                 335

Arg Leu Ser Thr Gly Asp Thr Leu Ala Ala Ala Phe Val Ala Ala Asp
            340                 345                 350

Gln Leu Ile Leu Asp Leu Val Gly Ala Ser Ala Val Val Arg Leu
        355                 360                 365

Ala Gly Gln Glu Leu His Phe Gly Arg Thr Pro Pro Val Asp Ala Met
370                 375                 380

Gln Lys Val Leu Asp Ser Leu Gly Arg Pro Ser Pro Leu Glu Val Leu
385                 390                 395                 400

Ser Leu Asp Asp Val Thr Leu Arg His Pro Glu Leu Pro Glu Leu Leu
            405                 410                 415

Ala Ala Gly Ser Gly Ile Leu Leu Pro Leu Thr Ser Gly Asp Gly
            420                 425                 430

Asp Leu Ile Ala Trp Phe Arg Pro Glu His Val Gln Thr Ile Thr Trp
        435                 440                 445

Gly Gly Asn Pro Ala Glu His Gly Thr Trp Asn Pro Ala Thr Gln Arg
450                 455                 460

Met Arg Pro Arg Ala Ser Phe Asp Ala Trp Lys Glu Thr Val Thr Gly
465                 470                 475                 480

Arg Ser Leu Pro Trp Thr Ser Ala Glu Arg Asn Cys Ala Arg Glu Leu
            485                 490                 495

Gly Glu Ala Ile Ala Ala Glu Met Ala Gln Arg Thr
            500                 505
```

<210> SEQ ID NO 36
<211> LENGTH: 633
<212> TYPE: PRT
<213> ORGANISM: Arabidopsis thaliana

<400> SEQUENCE: 36

```
Met Val Ser Gly Val Gly Gly Ser Gly Gly Arg Gly Gly Arg
1               5                  10                 15

Gly Gly Glu Glu Glu Pro Ser Ser His Thr Pro Asn Asn Arg Arg
            20              25              30

Gly Gly Glu Gln Ala Gln Ser Ser Gly Thr Lys Ser Leu Arg Pro Arg
            35              40              45

Ser Asn Thr Glu Ser Met Ser Lys Ala Ile Gln Gln Tyr Thr Val Asp
50              55              60

Ala Arg Leu His Ala Val Phe Glu Gln Ser Gly Ser Gly Lys Ser
65              70              75              80

Phe Asp Tyr Ser Gln Ser Leu Lys Thr Thr Thr Tyr Gly Ser Ser Val
                85              90              95

Pro Glu Gln Gln Ile Thr Ala Tyr Leu Ser Arg Ile Gln Arg Gly Gly
            100             105             110

Tyr Ile Gln Pro Phe Gly Cys Met Ile Ala Val Asp Glu Ser Ser Phe
            115             120             125

Arg Ile Ile Gly Tyr Ser Glu Asn Ala Arg Glu Met Leu Gly Ile Met
            130             135             140

Pro Gln Ser Val Pro Thr Leu Glu Lys Pro Glu Ile Leu Ala Met Gly
145             150             155             160

Thr Asp Val Arg Ser Leu Phe Thr Ser Ser Ser Ile Leu Leu Glu
                165             170             175

Arg Ala Phe Val Ala Arg Glu Ile Thr Leu Leu Asn Pro Val Trp Ile
            180             185             190

His Ser Lys Asn Thr Gly Lys Pro Phe Tyr Ala Ile Leu His Arg Ile
            195             200             205

Asp Val Gly Val Val Ile Asp Leu Glu Pro Ala Arg Thr Glu Asp Pro
210             215             220

Ala Leu Ser Ile Ala Gly Ala Val Gln Ser Gln Lys Leu Ala Val Arg
225             230             235             240

Ala Ile Ser Gln Leu Gln Ala Leu Pro Gly Gly Asp Ile Lys Leu Leu
            245             250             255

Cys Asp Thr Val Val Glu Ser Val Arg Asp Leu Thr Gly Tyr Asp Arg
            260             265             270

Val Met Val Tyr Lys Phe His Glu Asp Glu His Gly Glu Val Ile Ala
            275             280             285

Glu Ser Lys Arg Asp Asp Leu Glu Pro Tyr Ile Gly Leu His Tyr Pro
            290             295             300

Ala Thr Asp Ile Pro Gln Ala Ser Arg Phe Leu Phe Lys Gln Asn Arg
305             310             315             320

Val Arg Met Ile Val Asp Cys Asn Ala Thr Pro Val Leu Val Val Gln
            325             330             335

Asp Asp Arg Leu Thr Gln Ser Met Cys Leu Val Gly Ser Thr Leu Arg
            340             345             350

Ala Pro His Gly Cys His Ser Gln Tyr Met Ala Asn Met Gly Ser Ile
            355             360             365

Ala Ser Leu Ala Met Ala Val Ile Ile Asn Gly Asn Glu Asp Asp Gly
            370             375             380

Ser Asn Val Ala Ser Gly Arg Ser Ser Met Arg Leu Trp Gly Leu Val
385             390             395             400

Val Cys His His Thr Ser Ser Arg Cys Ile Pro Phe Pro Leu Arg Tyr
                405             410             415

Ala Cys Glu Phe Leu Met Gln Ala Phe Gly Leu Gln Leu Asn Met Glu
```

```
                420                 425                 430
Leu Gln Leu Ala Leu Gln Met Ser Glu Lys Arg Val Leu Arg Thr Gln
            435                 440                 445
Thr Leu Leu Cys Asp Met Leu Arg Asp Ser Pro Ala Gly Ile Val
        450                 455                 460
Thr Gln Ser Pro Ser Ile Met Asp Leu Val Lys Cys Asp Gly Ala Ala
465                 470                 475                 480
Phe Leu Tyr His Gly Lys Tyr Tyr Pro Leu Gly Val Ala Pro Ser Glu
                485                 490                 495
Val Gln Ile Lys Asp Val Val Glu Trp Leu Leu Ala Asn His Ala Asp
            500                 505                 510
Ser Thr Gly Leu Ser Thr Asp Ser Leu Gly Asp Ala Gly Tyr Pro Gly
        515                 520                 525
Ala Ala Ala Leu Gly Asp Ala Val Cys Gly Met Ala Val Ala Tyr Ile
        530                 535                 540
Thr Lys Arg Asp Phe Leu Phe Trp Phe Arg Ser His Thr Ala Lys Glu
545                 550                 555                 560
Ile Lys Trp Gly Gly Ala Lys His His Pro Glu Asp Lys Asp Gly
                565                 570                 575
Gln Arg Met His Pro Arg Ser Ser Phe Gln Ala Phe Leu Glu Val Val
            580                 585                 590
Lys Ser Arg Ser Gln Pro Trp Glu Thr Ala Glu Met Asp Ala Ile His
        595                 600                 605
Ser Leu Gln Leu Ile Leu Arg Asp Ser Phe Lys Glu Ser Glu Ala Ala
        610                 615                 620
Met Asn Ser Lys Val Val Asp Gly Val
625                 630

<210> SEQ ID NO 37
<211> LENGTH: 755
<212> TYPE: PRT
<213> ORGANISM: Deinococcus radiodurans

<400> SEQUENCE: 37

Met Ser Arg Asp Pro Leu Pro Phe Phe Pro Leu Tyr Leu Gly Gly
1               5                   10                  15
Pro Glu Ile Thr Thr Glu Asn Cys Glu Arg Glu Pro Ile His Ile Pro
            20                  25                  30
Gly Ser Ile Gln Pro His Gly Ala Leu Leu Thr Ala Asp Gly His Ser
        35                  40                  45
Gly Glu Val Leu Gln Met Ser Leu Asn Ala Ala Thr Phe Leu Gly Gln
    50                  55                  60
Glu Pro Thr Val Leu Arg Gly Gln Thr Leu Ala Ala Leu Leu Pro Glu
65                  70                  75                  80
Gln Trp Pro Ala Leu Gln Ala Ala Leu Pro Pro Gly Cys Pro Asp Ala
                85                  90                  95
Leu Gln Tyr Arg Ala Thr Leu Asp Trp Pro Ala Ala Gly His Leu Ser
            100                 105                 110
Leu Thr Val His Arg Val Gly Glu Leu Leu Ile Leu Glu Phe Glu Pro
        115                 120                 125
Thr Glu Ala Trp Asp Ser Thr Gly Pro His Ala Leu Arg Asn Ala Met
    130                 135                 140
Phe Ala Leu Glu Ser Ala Pro Asn Leu Arg Ala Leu Ala Glu Val Ala
145                 150                 155                 160
```

```
Thr Gln Thr Val Arg Glu Leu Thr Gly Phe Asp Arg Val Met Leu Tyr
                165                 170                 175
Lys Phe Ala Pro Asp Ala Thr Gly Glu Val Ile Ala Glu Ala Arg Arg
            180                 185                 190
Glu Gly Leu His Ala Phe Leu Gly His Arg Phe Pro Ala Ser Asp Ile
        195                 200                 205
Pro Ala Gln Ala Arg Ala Leu Tyr Thr Arg His Leu Leu Arg Leu Thr
    210                 215                 220
Ala Asp Thr Arg Ala Ala Val Pro Leu Asp Pro Val Leu Asn Pro
225                 230                 235                 240
Gln Thr Asn Ala Pro Thr Pro Leu Gly Gly Ala Val Leu Arg Ala Thr
                245                 250                 255
Ser Pro Met His Met Gln Tyr Leu Arg Asn Met Gly Val Gly Ser Ser
            260                 265                 270
Leu Ser Val Ser Val Val Gly Gln Leu Trp Gly Leu Ile Ala
        275                 280                 285
Cys His His Gln Thr Pro Tyr Val Leu Pro Pro Asp Leu Arg Thr Thr
    290                 295                 300
Leu Glu Tyr Leu Gly Arg Leu Ser Leu Gln Val Gln Val Lys Glu
305                 310                 315                 320
Ala Ala Asp Val Ala Ala Phe Arg Gln Ser Leu Arg Glu His His Ala
                325                 330                 335
Arg Val Ala Leu Ala Ala His Ser Leu Ser Pro His Asp Thr Leu
            340                 345                 350
Ser Asp Pro Ala Leu Asp Leu Leu Gly Leu Met Arg Ala Gly Gly Leu
        355                 360                 365
Ile Leu Arg Phe Glu Gly Arg Trp Gln Thr Leu Gly Glu Val Pro Pro
    370                 375                 380
Ala Pro Ala Val Asp Ala Leu Ala Trp Leu Glu Thr Gln Pro Gly
385                 390                 395                 400
Ala Leu Val Gln Thr Asp Ala Leu Gly Gln Leu Trp Pro Ala Gly Ala
                405                 410                 415
Asp Leu Ala Pro Ser Ala Ala Gly Leu Leu Ala Ile Ser Val Gly Glu
            420                 425                 430
Gly Trp Ser Glu Cys Leu Val Trp Leu Arg Pro Glu Leu Arg Leu Glu
        435                 440                 445
Val Ala Trp Gly Gly Ala Thr Pro Asp Gln Ala Lys Asp Asp Leu Gly
    450                 455                 460
Pro Arg His Ser Phe Asp Thr Tyr Leu Glu Glu Lys Arg Gly Tyr Ala
465                 470                 475                 480
Glu Pro Trp His Pro Gly Glu Ile Glu Glu Ala Gln Asp Leu Arg Asp
                485                 490                 495
Thr Leu Thr Gly Ala Leu Gly Glu Arg Leu Ser Val Ile Arg Asp Leu
            500                 505                 510
Asn Arg Ala Leu Thr Gln Ser Asn Ala Glu Trp Arg Gln Tyr Gly Phe
        515                 520                 525
Val Ile Ser His His Met Gln Glu Pro Val Arg Leu Ile Ser Gln Phe
    530                 535                 540
Ala Glu Leu Leu Thr Arg Gln Pro Arg Ala Gln Asp Gly Ser Pro Asp
545                 550                 555                 560
Ser Pro Gln Thr Glu Arg Ile Thr Gly Phe Leu Leu Arg Glu Thr Ser
                565                 570                 575
Arg Leu Arg Ser Leu Thr Gln Asp Leu His Thr Tyr Thr Ala Leu Leu
```

-continued

```
            580                 585                 590
Ser Ala Pro Pro Val Arg Arg Pro Thr Pro Leu Gly Arg Val Val
                595                 600                 605

Asp Asp Val Leu Gln Asp Leu Glu Pro Arg Ile Ala Asp Thr Gly Ala
            610                 615                 620

Ser Ile Glu Val Ala Pro Glu Leu Pro Val Ile Ala Ala Asp Ala Gly
625                 630                 635                 640

Leu Leu Arg Asp Leu Leu His Leu Ile Gly Asn Ala Leu Thr Phe
                645                 650                 655

Gly Gly Pro Glu Pro Arg Ile Ala Val Arg Thr Glu Arg Gln Gly Ala
                660                 665                 670

Gly Trp Ser Ile Ala Val Ser Asp Gln Gly Ala Gly Ile Ala Pro Glu
                675                 680                 685

Tyr Gln Glu Arg Ile Phe Leu Leu Phe Gln Arg Leu Gly Ser Leu Asp
                690                 695                 700

Glu Ala Leu Gly Asn Gly Leu Gly Leu Pro Leu Cys Arg Lys Ile Ala
705                 710                 715                 720

Glu Leu His Gly Gly Thr Leu Thr Val Glu Ser Ala Pro Gly Glu Gly
                725                 730                 735

Ser Thr Phe Arg Cys Trp Leu Pro Asp Ala Gly Pro Leu Pro Gly Ala
                740                 745                 750

Ala Asp Ala
        755

<210> SEQ ID NO 38
<211> LENGTH: 397
<212> TYPE: PRT
<213> ORGANISM: Mycobacterium tuberculosis

<400> SEQUENCE: 38

Met Thr Asp His Val Arg Glu Ala Asp Ala Asn Ile Asp Asp Leu
1               5                   10                  15

Leu Gly Asp Leu Gly Gly Thr Ala Arg Ala Glu Arg Ala Lys Leu Val
                20                  25                  30

Glu Trp Leu Leu Glu Gln Gly Ile Thr Pro Asp Glu Ile Arg Ala Thr
            35                  40                  45

Asn Pro Pro Leu Leu Leu Ala Thr Arg His Leu Val Gly Asp Asp Gly
        50                  55                  60

Thr Tyr Val Ser Ala Arg Glu Ile Ser Glu Asn Tyr Gly Val Asp Leu
65                  70                  75                  80

Glu Leu Leu Gln Arg Val Gln Arg Ala Val Gly Leu Ala Arg Val Asp
                85                  90                  95

Asp Pro Asp Ala Val Val His Met Arg Ala Asp Gly Glu Ala Ala Ala
            100                 105                 110

Arg Ala Gln Arg Phe Val Glu Leu Gly Leu Asn Pro Asp Gln Val Val
        115                 120                 125

Leu Val Val Arg Val Leu Ala Glu Gly Leu Ser His Ala Ala Glu Ala
    130                 135                 140

Met Arg Tyr Thr Ala Leu Glu Ala Ile Met Arg Pro Gly Ala Thr Glu
145                 150                 155                 160

Leu Asp Ile Ala Lys Gly Ser Gln Ala Leu Val Ser Gln Ile Val Pro
                165                 170                 175

Leu Leu Gly Pro Met Ile Gln Asp Met Leu Phe Met Gln Leu Arg His
            180                 185                 190
```

Met Met Glu Thr Glu Ala Val Asn Ala Gly Glu Arg Ala Ala Gly Lys
            195                 200                 205

Pro Leu Pro Gly Ala Arg Gln Val Thr Val Ala Phe Ala Asp Leu Val
        210                 215                 220

Gly Phe Thr Gln Leu Gly Glu Val Val Ser Ala Glu Glu Leu Gly His
225                 230                 235                 240

Leu Ala Gly Arg Leu Ala Gly Leu Ala Arg Asp Leu Thr Ala Pro Pro
                245                 250                 255

Val Trp Phe Ile Lys Thr Ile Gly Asp Ala Val Met Leu Val Cys Pro
            260                 265                 270

Asp Pro Ala Pro Leu Leu Asp Thr Val Leu Lys Leu Val Glu Val Val
        275                 280                 285

Asp Thr Asp Asn Asn Phe Pro Arg Leu Arg Ala Gly Val Ala Ser Gly
290                 295                 300

Met Ala Val Ser Arg Ala Gly Asp Trp Phe Gly Ser Pro Val Asn Val
305                 310                 315                 320

Ala Ser Arg Val Thr Gly Val Ala Arg Pro Gly Ala Val Leu Val Ala
                325                 330                 335

Asp Ser Val Arg Glu Ala Leu Gly Asp Ala Pro Glu Ala Asp Gly Phe
            340                 345                 350

Gln Trp Ser Phe Ala Gly Pro Arg Arg Leu Arg Gly Ile Arg Gly Asp
        355                 360                 365

Val Arg Leu Phe Arg Val Arg Arg Gly Ala Thr Arg Thr Gly Ser Gly
            370                 375                 380

Gly Ala Ala Gln Asp Asp Asp Leu Ala Gly Ser Ser Pro
385                 390                 395

<210> SEQ ID NO 39
<211> LENGTH: 4
<212> TYPE: PRT
<213> ORGANISM: Artificial Sequence
<220> FEATURE:
<223> OTHER INFORMATION: Engineered peptide

<400> SEQUENCE: 39

Arg Ala Glu Leu
1

<210> SEQ ID NO 40
<211> LENGTH: 5
<212> TYPE: PRT
<213> ORGANISM: Artificial Sequence
<220> FEATURE:
<223> OTHER INFORMATION: Engineered peptide

<400> SEQUENCE: 40

Arg Ala Glu Leu Ala
1               5

<210> SEQ ID NO 41
<211> LENGTH: 3
<212> TYPE: PRT
<213> ORGANISM: Artificial Sequence
<220> FEATURE:
<223> OTHER INFORMATION: Engineered peptide

<400> SEQUENCE: 41

Arg Ala Glu
1

```
<210> SEQ ID NO 42
<211> LENGTH: 8
<212> TYPE: PRT
<213> ORGANISM: Artificial Sequence
<220> FEATURE:
<223> OTHER INFORMATION: Engineered peptide

<400> SEQUENCE: 42

Arg Ala Glu Leu Ala Arg Leu Arg
1               5

<210> SEQ ID NO 43
<211> LENGTH: 9
<212> TYPE: PRT
<213> ORGANISM: Artificial Sequence
<220> FEATURE:
<223> OTHER INFORMATION: Engineered peptide

<400> SEQUENCE: 43

Arg Ala Glu Leu Ala Arg Leu Arg Ala
1               5

<210> SEQ ID NO 44
<211> LENGTH: 11
<212> TYPE: PRT
<213> ORGANISM: Artificial Sequence
<220> FEATURE:
<223> OTHER INFORMATION: Engineered peptide

<400> SEQUENCE: 44

Arg Ala Glu Leu Ala Arg Leu Arg His Tyr Asp
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Engineered peptide

<400> SEQUENCE: 45

Arg Ala Glu Leu Ala Arg Leu Arg Ala Glu Leu Ala
1               5                   10

<210> SEQ ID NO 46
<211> LENGTH: 19
<212> TYPE: PRT
<213> ORGANISM: Artificial Sequence
<220> FEATURE:
<223> OTHER INFORMATION: Engineered peptide

<400> SEQUENCE: 46

Asp Thr Leu Thr Gly Ala Leu Gly Glu Arg Leu Ser Glu Arg Lys Glu
1               5                   10                  15

Val Thr Val

<210> SEQ ID NO 47
<211> LENGTH: 21
<212> TYPE: PRT
<213> ORGANISM: Artificial Sequence
<220> FEATURE:
<223> OTHER INFORMATION: Engineered peptide

<400> SEQUENCE: 47

Asp Thr Leu Thr Gly Ala Leu Gly Glu Arg Leu Arg Ala Glu Glu Arg
1               5                   10                  15
```

```
Lys Glu Val Thr Val
        20

<210> SEQ ID NO 48
<211> LENGTH: 22
<212> TYPE: PRT
<213> ORGANISM: Artificial Sequence
<220> FEATURE:
<223> OTHER INFORMATION: Engineered peptide

<400> SEQUENCE: 48

Asp Thr Leu Thr Gly Ala Leu Gly Glu Arg Leu Arg Ala Glu Leu Glu
1               5                   10                  15

Arg Lys Glu Val Thr Val
        20

<210> SEQ ID NO 49
<211> LENGTH: 29
<212> TYPE: PRT
<213> ORGANISM: Artificial Sequence
<220> FEATURE:
<223> OTHER INFORMATION: Engineered peptide

<400> SEQUENCE: 49

Asp Thr Leu Thr Gly Ala Leu Gly Glu Arg Leu Arg Ala Glu Leu Ala
1               5                   10                  15

Arg Leu Arg His Tyr Asp Glu Arg Lys Glu Val Thr Val
        20                  25

<210> SEQ ID NO 50
<211> LENGTH: 25
<212> TYPE: PRT
<213> ORGANISM: Artificial Sequence
<220> FEATURE:
<223> OTHER INFORMATION: Engineered peptide

<400> SEQUENCE: 50

Asp Thr Leu Thr Gly Ala Leu Gly Glu Arg Glu Arg Lys Glu Val Thr
1               5                   10                  15

Val Ala Phe Ala Asp Leu Val Gly Phe
        20                  25

<210> SEQ ID NO 51
<211> LENGTH: 30
<212> TYPE: PRT
<213> ORGANISM: Artificial Sequence
<220> FEATURE:
<223> OTHER INFORMATION: Engineered peptide

<400> SEQUENCE: 51

Asp Thr Leu Thr Gly Ala Leu Gly Glu Arg Leu Arg Ala Glu Leu Glu
1               5                   10                  15

Arg Lys Glu Val Thr Val Ala Phe Ala Asp Leu Val Gly Phe
        20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Engineered peptide

<400> SEQUENCE: 52

Asp Thr Leu Thr Gly Ala Leu Gly Glu Arg Leu Arg Ala Glu Leu Ala
1               5                   10                  15
```

```
-continued

Glu Arg Lys Glu Val Thr Val Ala Phe Ala Asp Leu Val Gly Phe
            20                  25                  30

<210> SEQ ID NO 53
<211> LENGTH: 34
<212> TYPE: PRT
<213> ORGANISM: Artificial Sequence
<220> FEATURE:
<223> OTHER INFORMATION: Engineered peptide

<400> SEQUENCE: 53

Asp Thr Leu Thr Gly Ala Leu Gly Glu Arg Leu Arg Ala Glu Leu Ala
1               5                   10                  15

Arg Leu Arg Glu Arg Lys Glu Val Thr Val Ala Phe Ala Asp Leu Val
            20                  25                  30

Gly Phe

<210> SEQ ID NO 54
<211> LENGTH: 35
<212> TYPE: PRT
<213> ORGANISM: Artificial Sequence
<220> FEATURE:
<223> OTHER INFORMATION: Engineered peptide

<400> SEQUENCE: 54

Asp Thr Leu Thr Gly Ala Leu Gly Glu Arg Leu Arg Ala Glu Leu Ala
1               5                   10                  15

Arg Leu Arg Ala Glu Arg Lys Glu Val Thr Val Ala Phe Ala Asp Leu
            20                  25                  30

Val Gly Phe
        35

<210> SEQ ID NO 55
<211> LENGTH: 38
<212> TYPE: PRT
<213> ORGANISM: Artificial Sequence
<220> FEATURE:
<223> OTHER INFORMATION: Engineered peptide

<400> SEQUENCE: 55

Asp Thr Leu Thr Gly Ala Leu Gly Glu Arg Leu Arg Ala Glu Leu Ala
1               5                   10                  15

Arg Leu Arg Ala Glu Leu Ala Glu Arg Lys Glu Val Thr Val Ala Phe
            20                  25                  30

Ala Asp Leu Val Gly Phe
            35
```

NEAR-INFRARED LIGHT-ACTIVATED PROTEINS

CROSS-REFERENCE TO RELATED APPLICATIONS

This application claims priority to and is a continuation-in-part of pending U.S. patent application Ser. No. 14/326,778, filed Jul. 9, 2014, which in turn is a continuation in part of patented U.S. patent application Ser. No. 13/560,645 filed Jul. 27, 2012, which in turn claims priority from U.S. Provisional Patent Application No. 61/512,065 filed Jul. 27, 2011, both of which are incorporated herein by reference to the extent not inconsistent herewith for purposes of written description and enablement.

STATEMENT REGARDING FEDERALLY SPONSORED RESEARCH

This invention was made with Government support under NIH Contracts No. 2P20 RR016474 and R21 CA167862. The Government has certain rights in the invention.

Incorporated by reference herein in its entirety is the Sequence Listing entitled "Sequence Listing_ST25", created Jan. 19, 2016, size of 40 KB.

BACKGROUND

Light-activated fluorescent proteins have revolutionized imaging technologies, and with them our fundamental understanding of cellular processes (Zimmer, 2009). The use of light to control protein activities in live animals with spatiotemporal resolution unmatched by drugs has even greater potential (Miesenbock et al. 2009; Liu & Tonegawa, 2010). Optogenetic approaches utilizing natural photoreceptors have provided insights into the underpinnings of information processing in the nervous system, locomotion, awakening, neural circuits in Parkinson's disease, progression of epilepsy, etc. (Airan et al., 2009; Adamantidis et al., 2007; Cardin et al., 2009; Gradinaru et al., 2009; Sohal et al., 2009; Tønnesen et al., 2009; Tsai et al., 2009; and Gradinaru et al., 2010). Several groups have succeeded in engineering photoactivated proteins with new functions (Lee et al., 2008; Strickland et al., 2008; Tyszkiewicz and Muir, 2008; Yazawa et al., 2009; Möglich et al., 2009; Wu et al., 2009; and Georgianna & Deiters, 2010). However, the use of optogenetic approaches outside neurobiology remains very limited (reviewed in Möglich et al., 2010; Toettcher et al., 2011). The potential of using proteins activated by far-red and near-infrared (NIR) light, which penetrates animal tissues to the depths of several centimeters (Cuberddu et al., 1999; Wan et al., 1981; Byrnes et al., 2005) and therefore can be applied externally, has remained largely unexplored because of limitations in the ability to engineer such proteins with desired output activities.

SUMMARY

The ability to precisely activate or inactivate desired proteins in vivo—in specific cells or tissues of live animals, during normal or disease conditions—offers unprecedented insights into understanding diverse biological processes. However, current genetic and pharmaceutical approaches do not provide the spatiotemporal resolution and/or target specificity to accurately interrogate cellular functions in real time in vivo.

Light has emerged as an alternative means to control cellular activities with spatiotemporal precision unattainable by other approaches. The recently emerged field of optogenetics involves delivery into model organisms of recombinant genes encoding proteins that can be turned "on" and "off" by light. While natural photoactivated proteins (e.g., channelrhodopsins) have revolutionized neurobiology, the enormous potential of engineered photoactivated proteins remains largely untapped. We have elucidated principles of engineering far-red/NIR light-activated proteins using photosensory modules of bacteriophytochromes, a subclass of phytochromes containing the biliverdin IXα chromophore (Rockwell & Lagarias, 2006). Far-red/NIR light penetrates animal tissues much deeper (centimeter scale) than visible light (millimeter scale) absorbed by currently used photoreceptors; therefore bacteriophytochromes are particularly attractive and potentially transformative for optogenetic applications in mammalian models of development and disease as well as for disease treatment.

Applicants have designed bacteriophytochrome-based homodimeric photoactivated proteins and provide principles for engineering a broad spectrum of photoactivated functions. A large fraction of important signal transduction proteins operate as homodimers, e.g., membrane receptors, protein kinases, protein phosphatases, proteases, nucleases, and transcription factors. Three-dimensional structures of many of these proteins are known to the art. All these proteins represent targets for protein engineering.

"Transplantation" of a phytochrome photoreceptor module has been achieved previously, albeit only to homologous downstream domains (Levskaya et al., 2005, 2009). Phytochromes have also been designed to control protein-protein interactions in a light-dependent manner (Leung et al., 2008). However, the present disclosure is the first to provide photosensory modules of bacteriophytochromes to directly activate heterologous outputs. No such engineered modules have previously been available, and specifically, no light-activated bacteriophytochrome-based nucleotidyl cyclases or caspases have previously been available.

Provided herein are methods of controlling processes in live animal, plant or microbial organisms via genetically engineered far-red/NIR-light activated homodimeric proteins, NIRLAHPs. These proteins are chimeras comprised of photosensory modules of bacteriophytochromes that are activated (or inactivated) by far-red/NIR light and output modules that possess enzymatic activity and/or ability to bind to DNA, RNA, protein, or small molecules.

In this application, the term "NIR light" is used to describe light of 700-3000 nm wavelengths, commonly defined as NIR or infra-red A (IR-A), as well as an adjacent region of far-red light of 650-700 nm wavelengths.

Genes encoding NIRLAHPs can be introduced into live animals, plants or microbes, where their activities can be turned on by NIR light, controlled by the duration and/or intensity of light, and turned off by light of a different wavelength than the activating light. By using NIRLAHPs one can regulate diverse cellular processes with high spatial and temporal precision in a nontoxic manner, often using external light sources. For example, NIRLAHPs possessing nucleotidyl cyclase, protein kinase, protease, DNA-binding and RNA-binding activities can be used to control metabolic enzymes, signal transduction, cell apoptosis, proliferation, adhesion, differentiation and other processes. These features of NIRLAHPs can be used in various medical applications. For example, a NIR light-activated executor (effector) caspase can be introduced into tumors (or other kinds of disease-causing cells, e.g., cells carrying viruses) to induce an apoptotic cell death pathway, thus providing a noninvasive gene therapy of cancer (or viral diseases). Human cells expressing hormones (e.g., insulin) can be regulated by NIRLAHPs (e.g., due to the light-regulated gene expression or hormone-synthesizing activity) and can be used to treat hormone deficiencies (e.g., diabetes). NIRLAHPs can be used to photoactivate immune cells at desired locations (e.g., tumor or infection sites). NIRLAHPs can also be used to convert prodrugs into active drugs in irradiated tissues and/or organs. NIRLAHPs expressed in bacteria (e.g., *E. coli* or *Lactobacillus*) that belong to normal human or animal microflora can be used to photoactivate organ-localized (e.g., colon, vagina) synthesis of bacteriophages, antibiotics, and other drugs to target pathogenic microorganisms, polyps and tumors or to produce probiotics. Some NIRLAHPs can be used as protein-based drugs directly (e.g., by light-activated binding and control of cellular receptors). NIRLAHPs can also be used in cell-based nanomanufacturing (by virtue of light-dependent cell growth or light-dependent production of a desired product), and in industrial applications (e.g., light-induced dissolution of bacterial biofilms formed in the presence of engineered near-infrared light-sensitive cells that secrete biofilm-dispersion agents).

The principal advantages of NIR light over ultraviolet (UV) and visible light, which are sensed by all other types of photoreceptor proteins, is superior penetration into biological tissues (centimeter scale) and lack of toxicity. Therefore, activities of NIRLAHPs can be controlled in tissues that are not accessible to UV and visible light (e.g., most animal tissues); they can be controlled not only by implanted light sources, but in many cases, by external light sources (e.g., by lasers or light-emitting diodes, LEDs, placed outside organisms that are being controlled). Additional advantages of bacteriophytochrome-based NIRLAHPs involve their capacity for instant photoinactivation (usually by light of a longer wavelength than the activating light); lack of known toxicity of NIR light; and lack of toxicity, at low doses, of the chromophore biliverdin IXα, which is naturally present in most animal tissues or can be supplied via injection, diet, or via synthesis in vivo by a heterologous heme oxygenase gene.

Methods are provided herein for producing photoactive fusion proteins having a desired activity controllable by NIR light, said method comprising the steps: a. designing one or more homodimeric fusion proteins, each comprising a photoreceptor protein module and a heterologous output module, wherein: i. said homodimeric fusion proteins comprise two monomers that each comprise: (1) a photoreceptor module of a bacteriophytochrome; and (2) a heterologous output module capable of being activated upon homodimerization to perform said desired activity; and ii. said monomers are not active when separated, but are capable of combining to form homodimers that are controllable by NIR light; wherein designing said fusion proteins comprises identifying candidate output domains based on 3D structures or structural models, identifying candidate protein fusion sites and estimating lengths of α-helices linking said output modules to said photosensory modules; b. producing a plurality of DNA molecules, each encoding a said monomer of a said homodimeric fusion protein that has at least one unique fusion site; c. screening said DNA molecules for their ability to produce homodimeric photoactive fusion proteins capable of performing said desired activity by a method comprising: transforming a designed test organism with a plurality of different said DNA molecules such that different said fusion proteins are expressed in each test organism; ii. allowing the expressed fusion proteins to bind bacteriophytochrome chromophore and form homodimeric proteins; and iii. applying selected wavelengths of NIR light to said transformed organisms and determining the level of said desired activity of said fusion proteins in said organisms in the presence and absence of said selected wavelengths of light; wherein the level of said desired activity of said fusion proteins is controllable by NIR light when the level of said desired activity is changed by the presence and/or absence of NIR light having said selected wavelengths. Controllability by NIR light of the fusion proteins exists when the fusion proteins have higher ratios of activity in the light versus dark or vice versa.

The bacteriophytochrome photoreceptor module can be from the BphG1 protein from *Rhodobacter sphaeroides*. The test organism for expression of said fusion protein can be a cultured organism selected from the group consisting of *E. coli*, yeast, plant, and animal cells selected or modified so as to detectably exhibit the level of activity of said expressed fusion protein controllable by the presence or absence of NIR light. Examples of light-activated fusion proteins produced by the methods hereof are light-responsive nucleotidyl cyclases and light-responsive uncleavable procaspase-3.

The test organisms can comprise an endogenous chromophore or they may not. If required, they are transformed with DNA encoding a heme oxygenase gene capable of being expressed therein to produce a biliverdin Ixa chromophore, e.g. the BphO1 protein from *Rhodobacter sphaeroides*.

The method also comprises modifying the design of the fusion proteins that are controllable by NIR light to produce additional candidate fusion proteins by designing additional fusion sites and linkers for said fusion proteins and repeating the steps of producing DNA encoding the additional fusion proteins, transforming suitable organisms with this DNA, expressing the DNA, and screening the resultant fusion proteins for additional fusion proteins controllable by NIR light. This is achieved by increasing or decreasing the lengths and amino acid sequences of the α-helical linkers linking the photoreceptor modules with the output modules, e.g., the linker lengths can be increased or decreased by three or four amino acids, representing one full turn of the linker strand. Accordingly, the amino acid sequence of the linker used herein optionally comprises or consists essentially of an amino acid sequence which is capable of forming one or more complete alpha helical turns. The number of alpha helical turns that the linker is capable of forming is at least one, at least two, at least three, at least four, at least five, at least six, at least seven or more.

Fusion proteins controllable by NIR light, or additional fusion proteins controllable by NIR light produced by increasing or decreasing their linker lengths, can be mutagenized to create further candidate fusion proteins controllable by NIR light, followed by repeating the screening steps to identify photoactivated fusion proteins with improved properties, e.g. low background activity and high photoactivation ratio.

In various embodiments, fusion proteins are produced by the methods hereof whose activity can be increased by the application of NIR light of a selected wavelength, or can be decreased by the application of NIR light of a selected wavelength. In embodiments, the desired activity can be gradually decreased or gradually increased by ceasing to apply NIR light of a selected wavelength or by application of NIR light of a selected wavelength.

Provided herein are homodimeric fusion proteins controllable by NIR light, said fusion proteins comprising a photoreceptor module comprising a bacteriophytochrome and a heterologous output module capable of producing a desired activity, e.g., light-activated nucleotidyl cyclases or light-activated uncleavable procaspase-3. Recombinant DNA molecules encoding portions of homodimeric fusion proteins hereof are also provided.

In addition, methods are provided herein for controlling an in vivo process in a host, which is a living cell or organism using the fusion proteins hereof. The method comprises: a. introducing into the cell or organism a DNA sequence encoding a homodimeric fusion protein comprising a photoreceptor module comprising a bacteriophytochrome and a heterologous output module capable of modulating said process; b. allowing said fusion protein to be expressed in said host; and c. applying NIR light of a selected wavelength to the host or preventing NIR light of a selected wavelength from reaching the host; thereby modulating the process under control of NIR light. Such processes can be selected from the group consisting of metabolic processes, signal transduction, cell apoptosis, cell proliferation, cell adhesion, and cell differentiation.

In embodiments hereof, methods hereof for producing NIRLAHPs having a desired activity controllable by NIR light comprise the steps of designing one or more homodimeric fusion proteins, each comprising a bacteriophytochrome photoreceptor module and a heterologous output module, capable of being NIR-light activated to perform said desired activity. The monomers of the fusion proteins combine spontaneously to form homodimers, and have autocatalytic activity to bind biliverdin IXα, thus forming NIRLAHPs. Designing NIRLAHPs comprises (a) identifying, based on biochemical information candidate protein output domains that function as homodimers and can be activated by homodimerization; (b) using 3D structures or building 3D models to identify optimal fusion sites and peptide linkers for attaching the heterologous output modules to the bacteriophytochrome photoreceptor modules; (c) producing a plurality of DNA molecules (a DNA library), each encoding a monomer of a homodimeric fusion protein that has at least one unique fusion site or linker sequence; and (d) screening the DNA molecules for their ability to produce homodimeric photoactive fusion proteins capable of performing the desired activity in a test organism. The screening is done by transforming a test organism designed to respond to the desired activity with the DNA constructs encoding the monomers of the homodimeric fusion proteins; allowing the expressed fusion proteins to spontaneously bind biliverdin IXα and form homodimers; applying light of selected wavelengths to the transformed organisms; and comparing the level of said desired activity of the expressed fusion proteins in the test organism in the dark and in the light. The method can then comprise (e) subjecting fusion proteins that have NIR light-activated activities identified by screening to random mutagenesis and subsequent screening (by the method described above) for mutant derivatives with improved qualities, e.g., low activity in the dark and a high light-to-dark activation ratio. The method can further comprise: (f) purification, and spectral and/or biochemical characterization of NIRLAHPs.

The optimized NIRLAHPs can be used for controlling in vivo processes in other organisms, including animals and humans, using internal and/or external sources of NIR light. The genes encoding NIRLAHPs can be introduced into the cell or organism via methods known to the art, including transformation by DNA, viral infection, and bacteriofection.

Light-activated fusion proteins, DNA molecules encoding them, and methods for using them to control processes in living hosts are also provided herein.

BRIEF DESCRIPTION OF THE DRAWINGS

The following drawings illustrate various aspects of the photoreceptor modules for optogenetic applications provided in the present disclosure.

FIG. 5 far left panel is a schematic depiction of the *R. sphaeroides* BphG protein comprising the photoreceptor (PAS-GAF-PHY) and output (GGDEF) modules. The BphG protein is depicted as a parallel homodimer. FIG. 5 middle left panel is a 3D model of the BphG protein based on the 3D structure 3c2w for the phototreceptor module and 3ic1 for the output domain (3D structures from Protein Data Bank [PDB], rcsb.org/pdb). The dashed line represents the approximate position within the α-helices (extending from the photoreceptor PHY domain) for fusion with a heterologous homodimeric output module. An arrow indicates rotation of an output domain as a potential outcome of light-induced conformational changes in BphG. FIG. 5 middle right panel depicts a 3D model of the homodimeric adenylyl cyclase domains of protein CyaB1 from *Nostoc* sp. (modeled based upon the PDB structure 1wc5, the protein with the highest sequence identity to CyaB1). The output module of *R. sphaeroides* BphG, the diguanylyl cyclase GGDEF domain, was replaced with a distantly related adenylyl cyclase (ACyc) domain from *Nostoc* sp. CyaB1 resulting in the photoactivated adenylyl cyclase. FIG. 5 far right panel is a schematic representation of the protein domain architecture (GAF-PAS-ACyc) of *Nostoc* sp. CyaB1 depicted as a homodimer.

FIG. 9 provides protein sequences near fusion points of selected engineered adenylyl cyclase fusions between the photoreceptor module of BphG and adenylyl cyclase (ACyc domain) of CyaB1. Photoresponses in *E. coli* of the fusion proteins were recorded at two levels of expression of the chimeric proteins: low (5 µM isopropyl-beta-D-thiogalactopyranoside, IPTG) and high (50 µM IPTG). β-galactosidase expression (judged by the intensity of blue color) is dependent on intracellular cAMP levels. A: light-activated (higher β-galactosidase expression in the light versus dark); I: light-inactivated (higher β-galactosidase expression in the dark versus light); +: light-independent activity; –: no activity (in the dark or light). It is emphasized that protein fusions containing approximately one helical turn (+/–3-4 amino acids, aa) longer or shorter α-helical sequences had the same type of light-responsiveness, e.g., light-activated RlaC17 (SEQ ID NO:6); RlaC29 which includes MAQRTRAELARLRERKEVT [SEQ ID NO:2]; RlaC17 (which includes SEQ ID NO:6+4 aa); RlaC25 (which includes SEQ ID NO:10) (which has the sequence of SEQ ID NO:6–4 aa); and RlaC22 MAQRTRERKEVT [which includes SEQ ID NO:9] (which has the sequence of SEQ ID NO:6–3 aa).

With respect to the remaining constructs shown in FIG. 9, RlaC28 whose sequence includes MAQRTRAELARLERKEVT [SEQ ID NO: 3] showed activity. RlaC24, whose sequence includes MAQRTRAELARERKEVT [SEQ ID NO: 4] showed no activity, as did RlaC23, whose sequence includes MAQRTRAELAERKEVT [SEQ ID NO:5], RlaC30, whose sequence includes MAQRERKEVT [SEQ ID NO:11], RlaC26, whose sequence includes MAQERKEVT [SEQ ID NO:12] and Rlac27, whose sequence includes MAERKEVT [SEQ ID NO:13].

Figure 10:
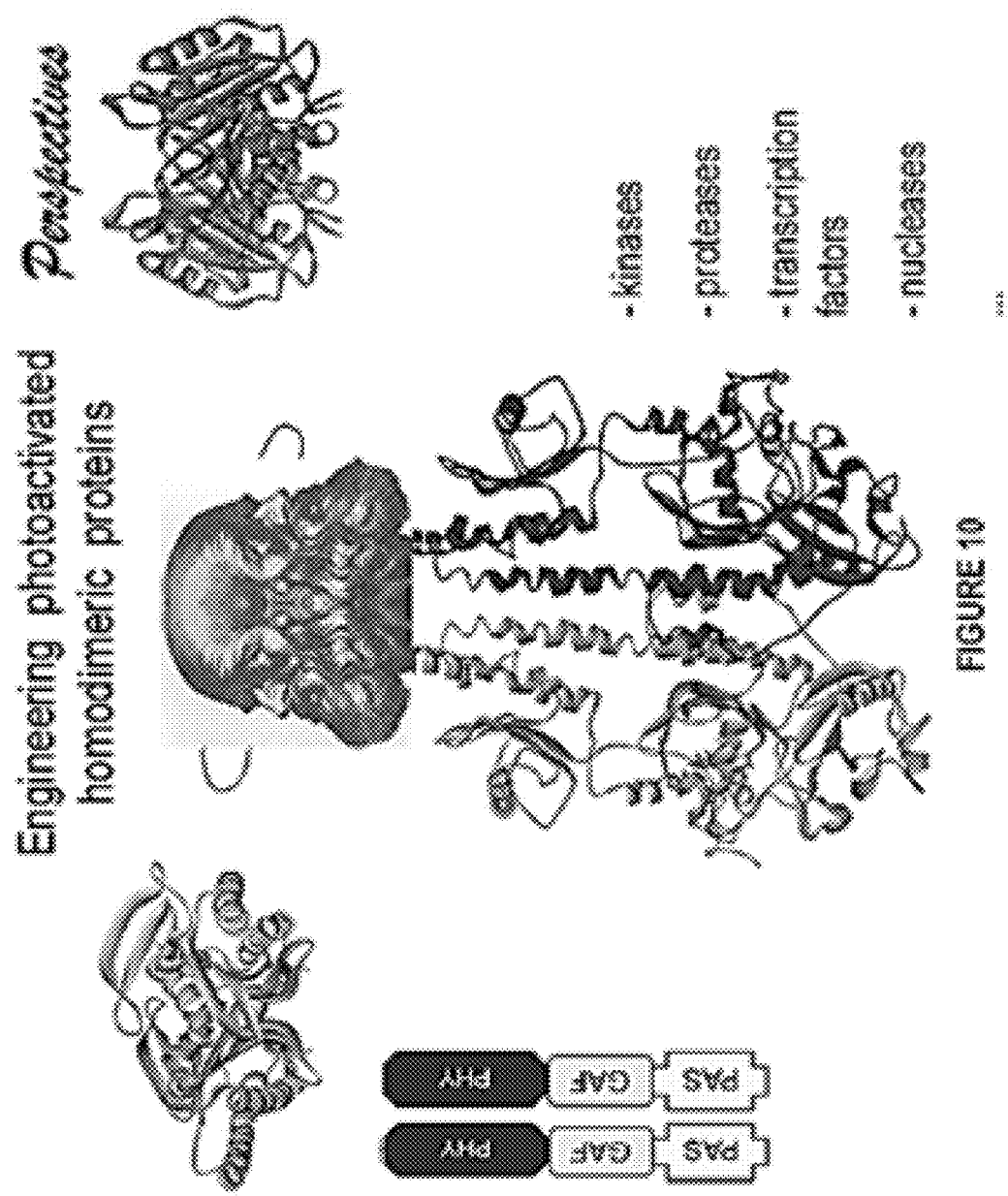

FIG. 10 illustrates an overview of principles elucidated herein. The photosensory module of a bacteriophytochrome is shown schematically in the lower left with a modeled heterologous active module shown above. In the center of the figure, a modeled photosensory module is shown with the active module symbolized by a "homodimeric head". On the right, a generic modeled active module is illustrated above a list of examples of modules that can be used to engineer NIRLAHPs, e.g., kinases, proteases, transcription factors, nucleases, etc.

Figure 11:
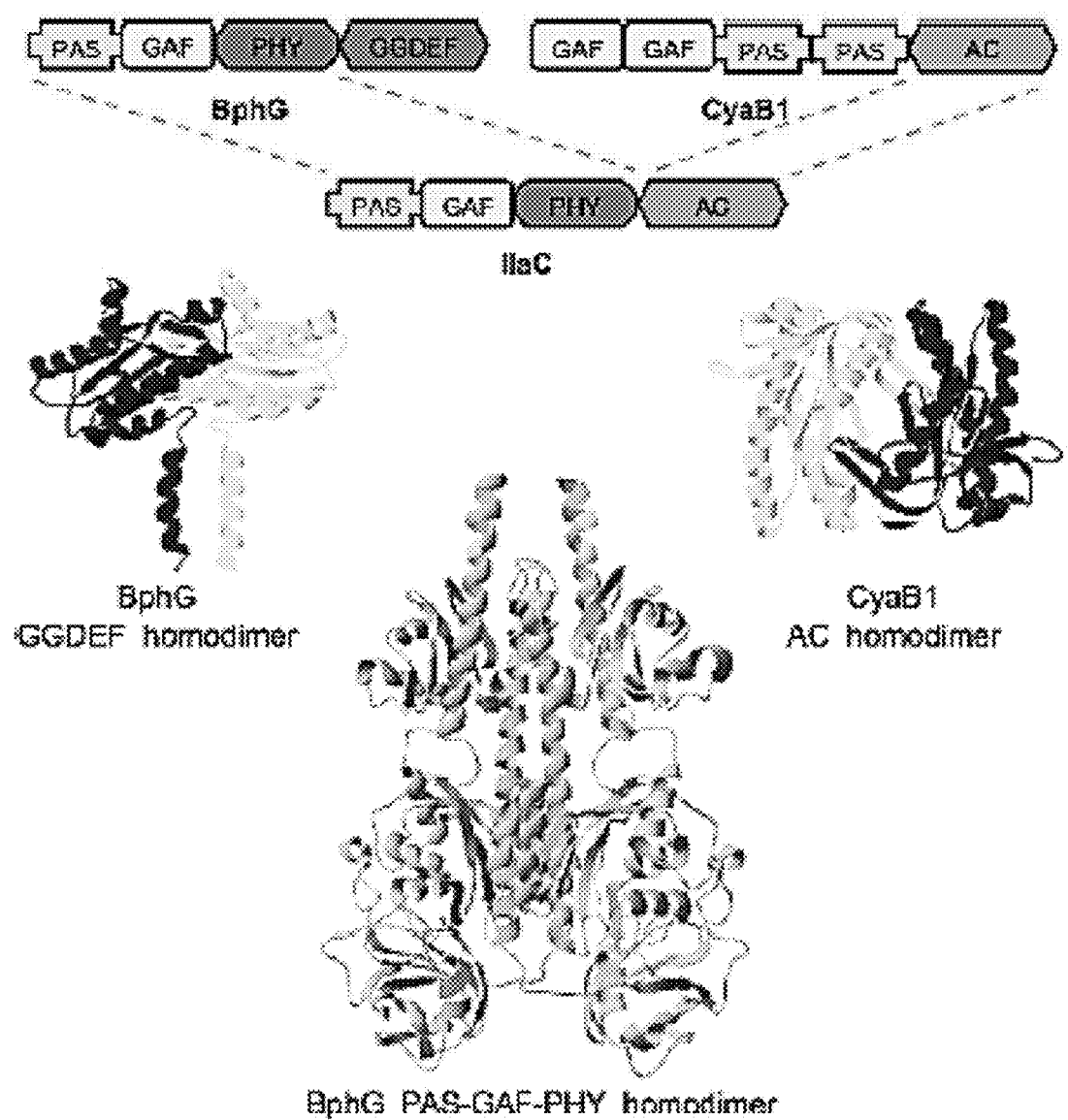

FIG. 11 illustrates domain architectures, and 3D models of the components used in infrared light-activated adenyl cyclase (IlaC) engineering. *R. sphaeroides* bacteriophytochrome BphG is bacteriophytochrome DGC; *Nostoc* sp CyaB1 is homodimeric adenylyl cyclase. In this application, RlaC and IlaC are used interchangeably.

Figure 12:

FIG. 12 illustrates IlaC engineering strategy, a subset of BphG-CyaB1 protein fusion sequences, their AC activities and responsiveness to light. The aa shades of gray correspond to the shades of protein domains shown above protein sequences. Interdomain linkers are shown in black. Predicted secondary structure elements, α-helix and β-strand, are shown above sequences. AC activity: +, active; –, inactive, according to the lacZ plate assays (see panel B). Response to light: –, no response; ↑, activation; ↓, inactivation.

Figure 13:
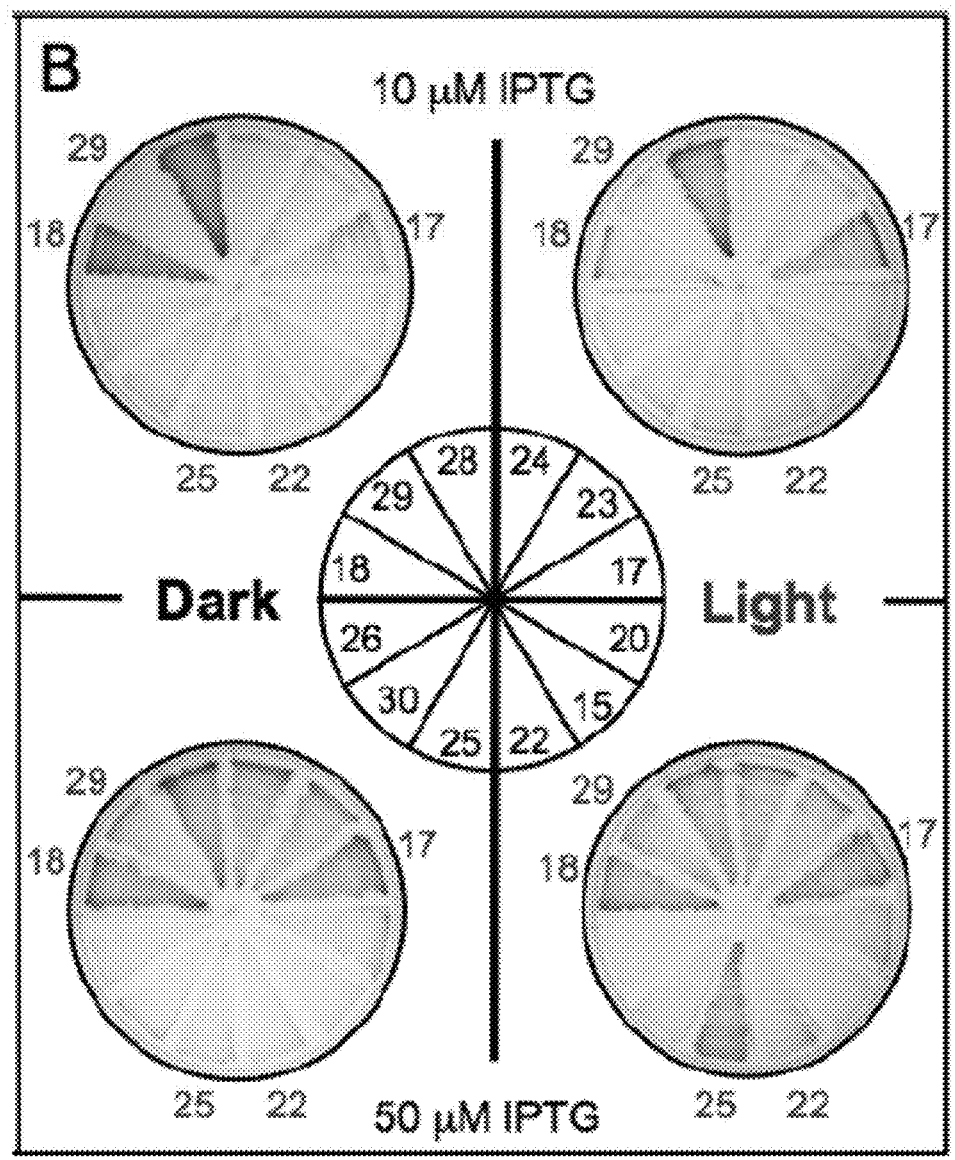

FIG. 13 shows images of the lacZ plate assays of AC activity. Selected *E. coli* BL21[DE3] (pETilaC#; pT7-ho1-1) strains from panel A were grown on LB agar containing X-gal and IPTG, either in the dark (left of center) or in the red light (right). Blue colony color indicates cAMP-CRP-induced lacZ expression. Each strain expressing an IlaC# was plated in a sector of each of the 4 plates. The plating guide is in the center of the panel. IlaC expression from pETilaC# was induced at two IPTG levels: 10 µM (top plates) and 50 µM (bottom plates).

Figure 14:
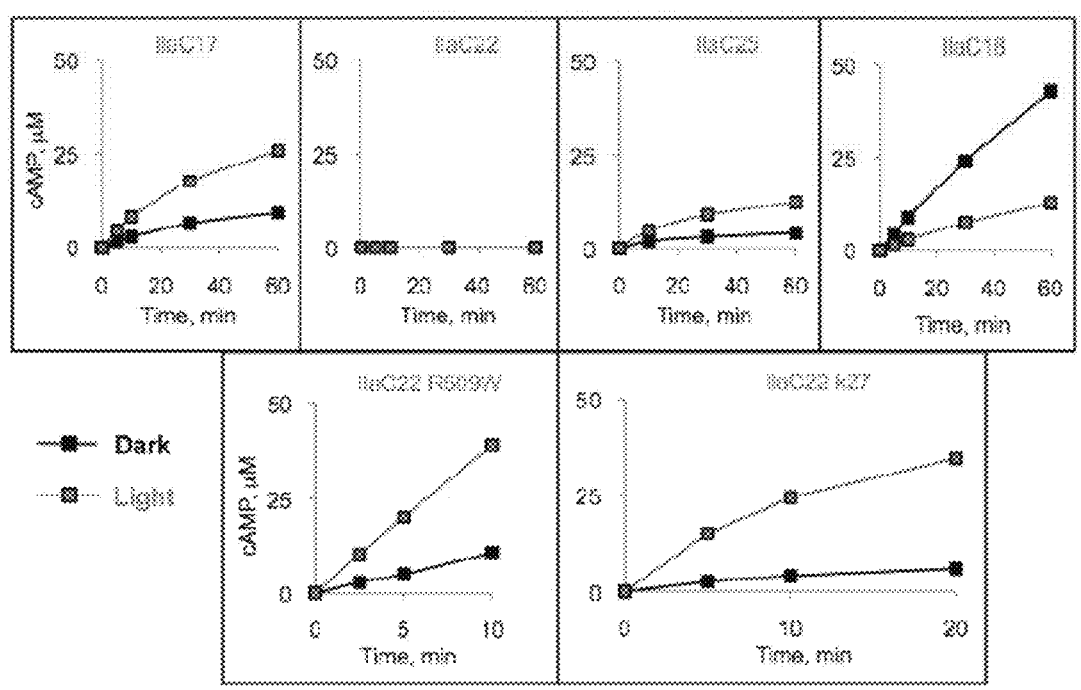

FIG. 14 shows kinetics of cAMP accumulation by the purified IlaC proteins in the dark and light. Top row, first-generation light-responsive proteins: IlaC18, light-inactivated AC; IlaC17, 22 and 25, light-activated AC. Bottom row, IlaC22 mutants with improved photodynamic ranges: IlaC22 R509W and IlaC k27. AC activity was measured at room temperature. cAMP was quantified by high pressure liquid chromatography (HPLC). Black traces, dark (dim green light); gray traces, irradiation with 700-nm light.

Figure 15:
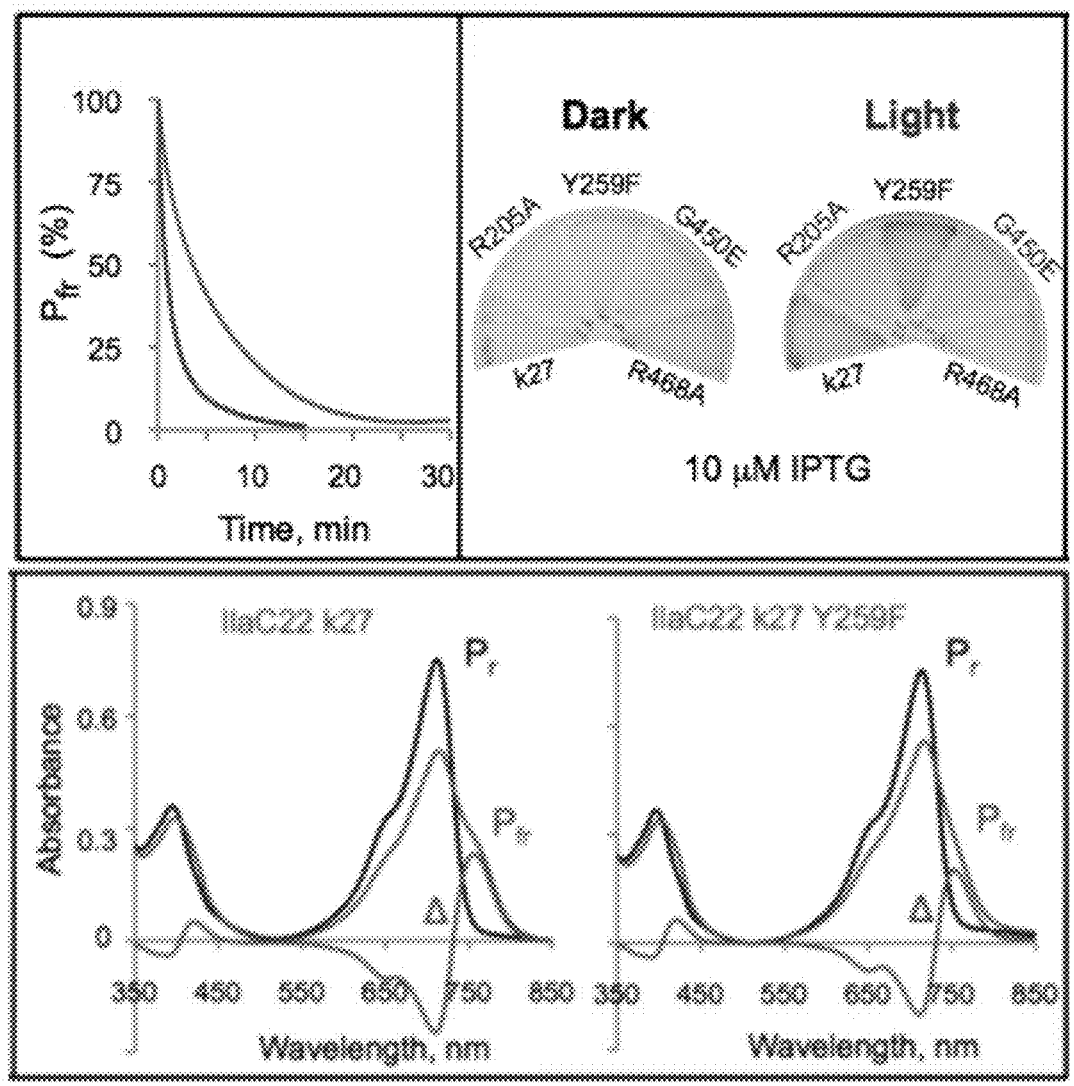

FIG. 15 shows photochemical characterization of IlaC variants. Top left panel shows kinetics of the dark recovery of IlaC derivatives from the lit (Pfr) state. Plotted are changes in absorbance at 755 nm over time following 5-min excitation with 700-nm light. Bottom trace, IlaC22 k27; top trace, IlaC22 k27 Y259F. Half of the Pfr form of IlaC22 k27 decayed after 46±3 s and half of the Pfr form of the IlaC22 k27 Y259F mutant decayed after 197±9 s. Top right panel shows plate assays of the IlaC k22 dark recovery mutants. Bottom panel shows light induced spectral changes in IlaC22 derivatives. Top trace (Pr), prior to irradiation, middle trace (Pfr), after irradiation with 700-nm light; Δ, difference (Pfr–Pr) spectra. IlaC22 k27, left panel; IlaC22 k27 Y259F, right panel.

Figure 16:
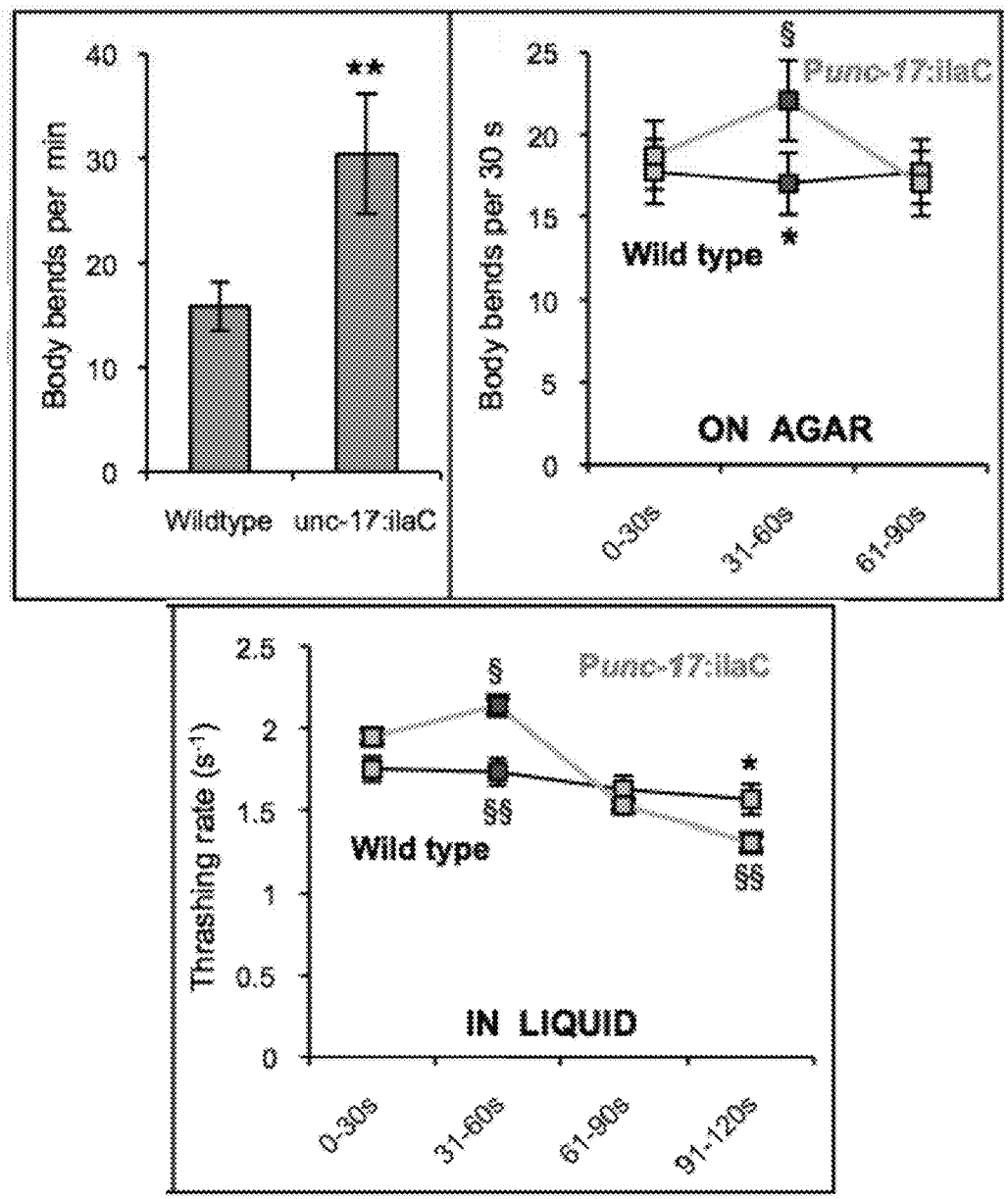

FIG. 16 shows red light-stimulated locomotion of animals expressing IlaC22 k27 in *C. elegans* cholinergic neurons (Punc-17:ilaC). Top left panel. When exposed to environmental light on an agar surface, transgenic Punc-17:IlaC animals have higher frequency of anterior body bends relative to wild-type animals (two-tailed Student's test, **$p<0.001$, N_12). Top right panel. Red (650 nm) light increases the number of body bends performed on an agar surface by Punc-17:IlaC animals (two-tailed Wilcoxon Rank-Sum test, § $p<0.05$, N=11). Bottom panel. Red light increases the thrashing rate in liquid of Punc-17:IlaC animals (two-tailed Wilcoxon Rank-Sum test, § $p<0.05$). After re-exposure to green light (532 nm; 61-120 s interval), Punc-17:IlaC animals thrash slower compared to their first green light exposure (two-tailed Wilcoxon Rank-Sum test, §§ $p<0.005$) and compared to wild-type controls (two-tailed Student's t-test, *$p<0.05$, N_20). Two transgenic strains were analyzed, both showing similar results. Analysis of body bends on an agar surface was performed on the strain NQ721 and analysis of the thrashing rate in liquid was performed on the strain NQ719. All experiments with *C. elegans* were performed by Mathew D. Nelson and David M. Raizen (University of Pensylvania).

Figure 17:
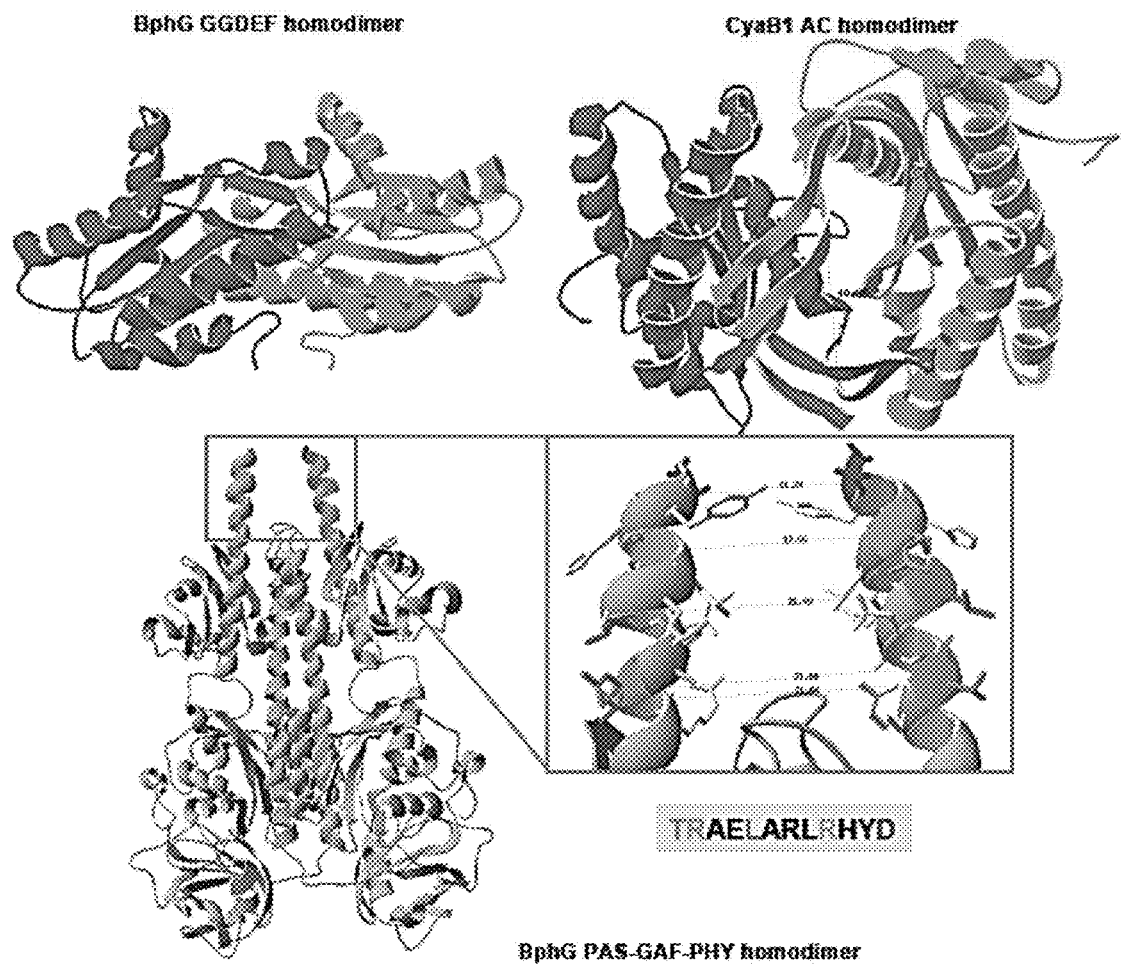

FIG. 17 shows structural models of BphG and the AC domain of CyaB1. The parallel dimer of the phytochrome domains was constructed using two PDB structures, combined in several steps.

Figure 18:
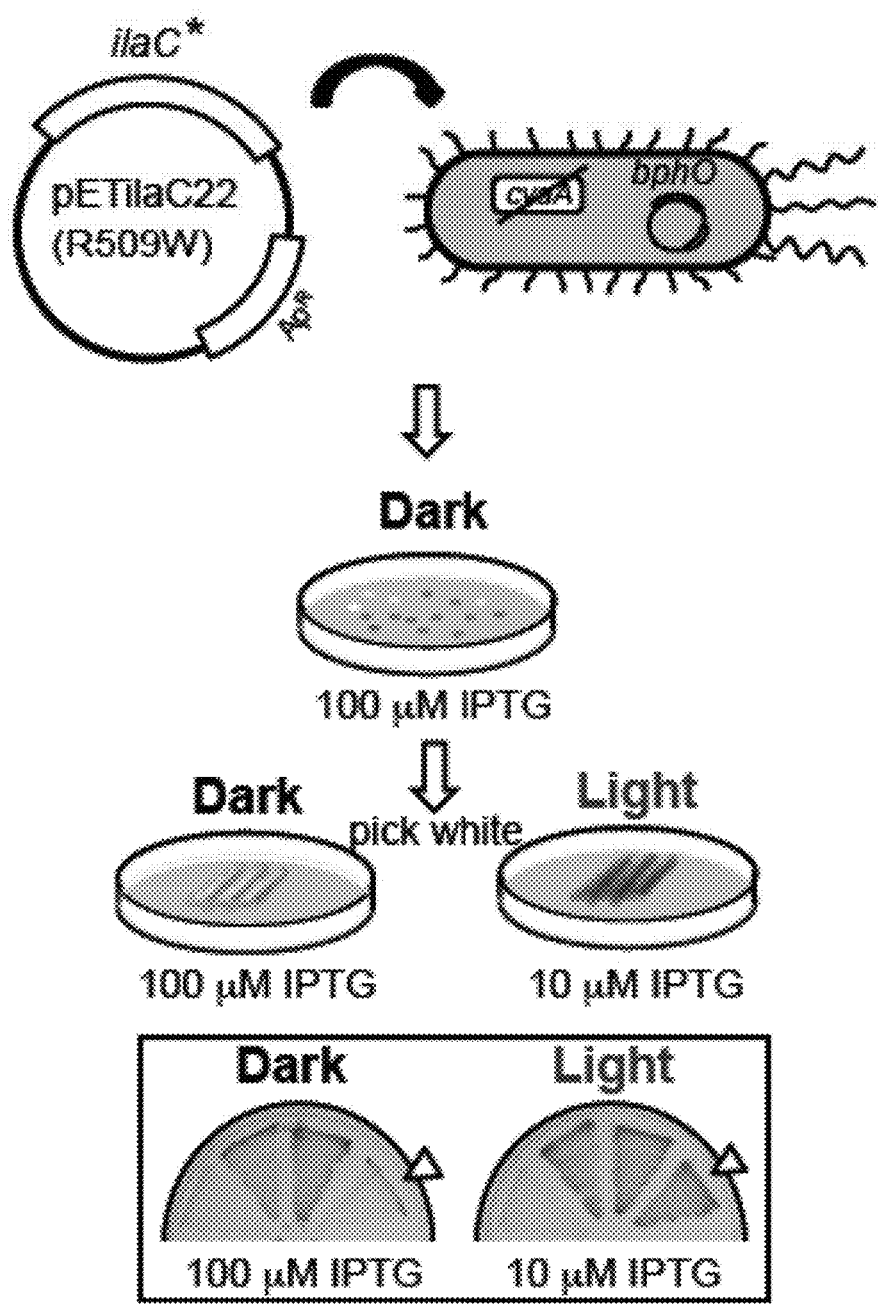

FIG. 18 shows a selection strategy used for isolating IlaC22 R509W mutants with decreased dark AC activities.

Figure 19:
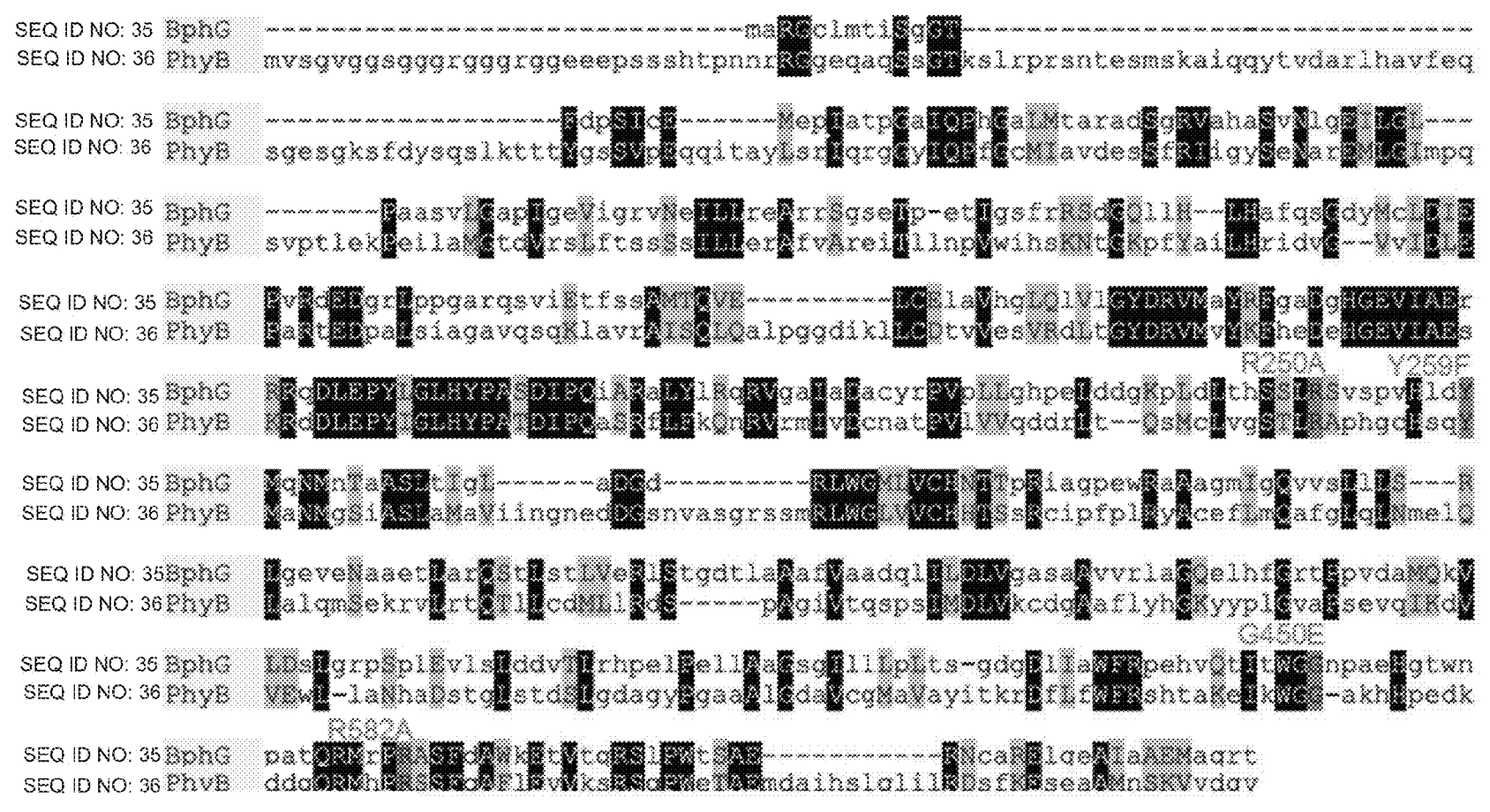

FIG. 19 illustrates identification of residues involved in slowing the dark thermal recovery of IlaC. Shown is alignment of the *R. sphaeroides* BphG bacteriophytochrome and the *Arabidopsis thaliana* phytochrome PhyB. Residues of PhyB affecting its photocycle and conserved in BphG are highlighted in dark gray Mutations of PhyB that extend the lit (Pfr) state of PhyB are shown in light gray.

Figure 20:
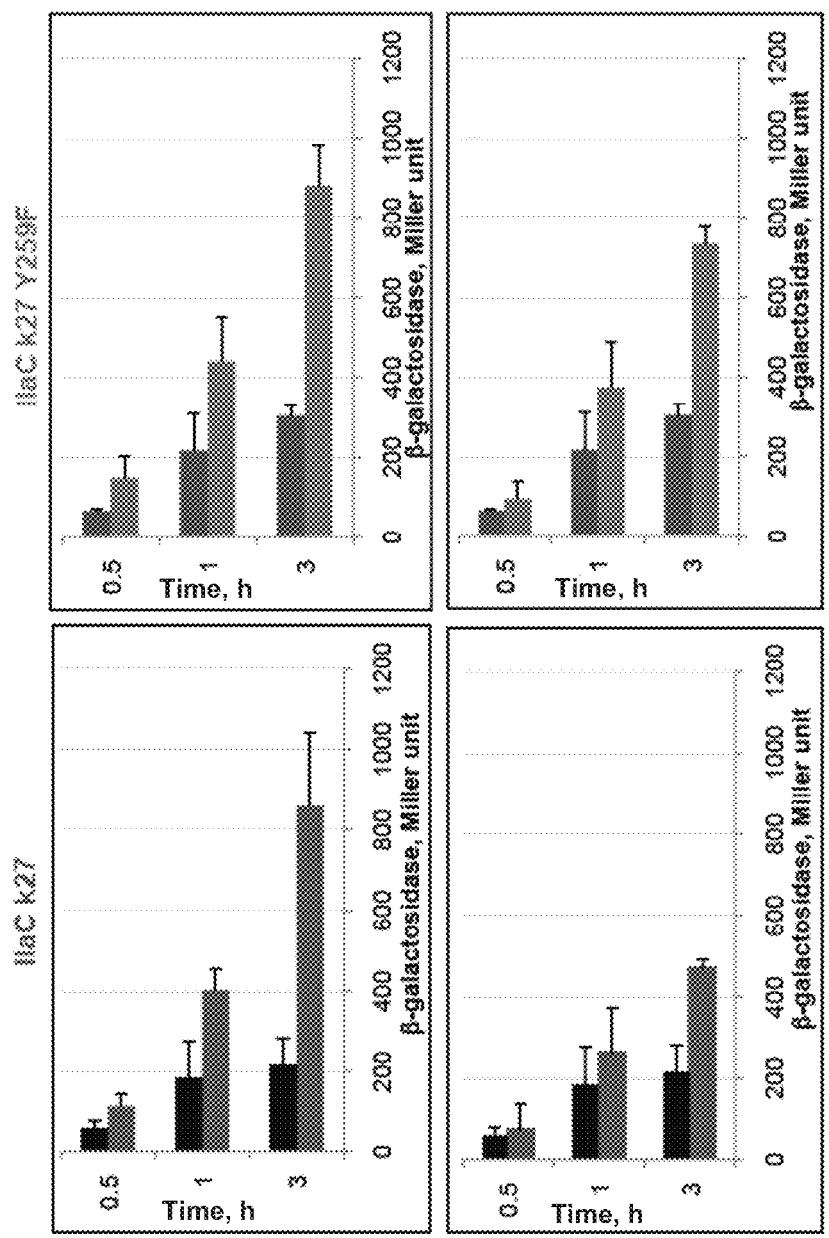

FIG. 20 shows effects of IlaC k27 and IlaC k27 Y259F on cAMP-CRP-dependent lacZ gene expression in *E. coli*. Strain BL21[DE3] cya (pT7-ho1-1) containing either pET-ilaCK27 or pET-ilaC k27 Y259F were grown in culture tubes on a shaking platform at 30° C. in LB supplemented with ampicillin (50 µg/mL) and kanamycin (50 µg/mL).

Figure 21:
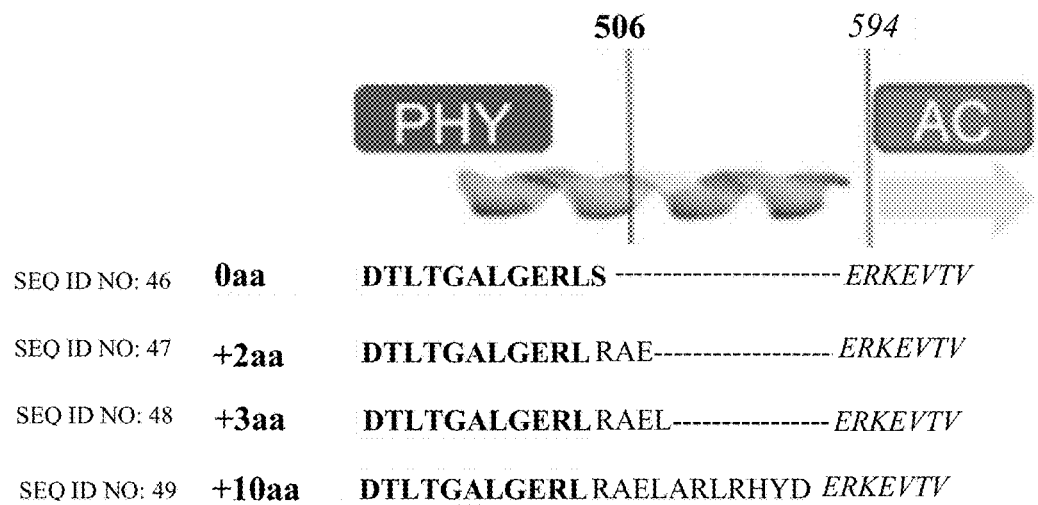

FIG. 21 provides protein sequences near fusion points of selected engineered nucleotidyl cyclase fusions between the photoreceptor module of *Deinococcus radiodurans* bacteriophytochrome BphP and adenylyl cyclase (ACyc domain) of CyaB1. Shown is a subset of the engineered fusion DrBphP-CyaB1 proteins possessing far-red/NIR light activated adenylyl cyclase activities.

Figure 22:
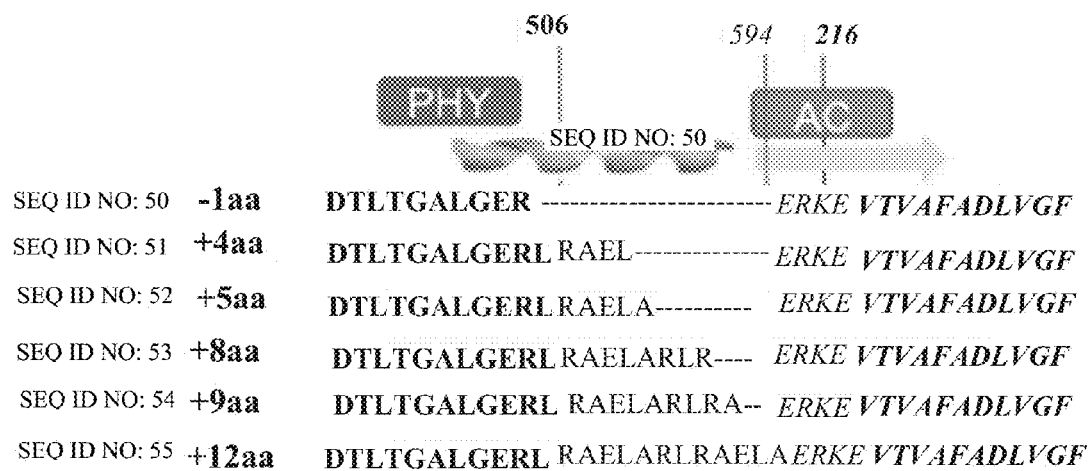

FIG. 22 provides protein sequences near fusion points of selected engineered nucleotidyl cyclase fusions between the photoreceptor module of *Deinococcus radiodurans* bacteriophytochrome BphP and adenylyl cyclase (ACyc domain) of *Mycobacterium tuberculosis* Rv1264 protein. Shown is a subset of the engineered fusion DrBphP-MtCya proteins possessing far-red/NIR light activated adenylyl cyclase activities.

All publications and websites disclosed herein are incorporated by reference to the extent not inconsistent herewith.

DETAILED DESCRIPTION

Definitions

Terms used herein have their generally accepted, conventional meaning in the art unless otherwise specifically defined.

A "fusion protein" hereof (also referred to herein as an "engineered protein," a "chimeric protein" and/or a "hybrid protein") is a protein that comprises an output module and a photosensory module that do not occur together in the same protein in nature.

An "output module" (also referred to herein as an "output domain") is the portion of a protein that performs a function, e.g., enzymatic activity, or binding to DNA, RNA or another protein.

A "photosensory module" (also referred to herein as a "photoreceptor module") is a portion of a protein that contains a chromophore, through which it senses and responds to light.

A "chromophore" is a molecule bound to the photoreceptor module that serves to detect NIR light and cause a conformational change in the output domain of the fusion protein when NIR light is applied. In bacteriophytochromes, the chromophore is biliverdin IXα.

A homodimer is a protein having two identical portions (monomers) that are not linked to each other by covalent bonds but can form stable structures involving protein-protein (monomer-monomer) interactions. In the homodimeric fusion proteins hereof that are photoactive, monomers making up the homodimeric proteins are inactive until they have joined to form a particular homodimeric conformation.

Bacteriophytochromes are a subclass of phytochrome photoreceptor proteins containing biliverdin IXα as a chromophore. The photosensory modules of biliverdin IXα comprise PAS-GAF-PHY protein domains. Bacteriophytochromes covalently bind biliverdin IXα to a conserved cysteine residue via an intrinsic biliverdin ligase activity.

"Near infrared" (NIR) light is generally considered in the art to have a wavelength of between about 700-750 and about 3000 nm. "Far-red" light is generally defined as light having a wavelength at the long-wavelength red end of the visible (red) spectrum, from about 700 to about 750 nm. The visible spectrum is generally defined as having a wavelength of about 390 to about 750 nm. Bacteriophytochromes sense light from about 650 to about 800 nm, within the "NIR window." Since this "NIR window" contains light variously defined as being in the visible, far-red and NIR categories, the term "near-infrared" ("NIR") is used herein to describe light in the "NIR window" that activates bacteriophytochromes, switching them from one (dark) conformation to another (lit) conformation and back, regardless of whether the light would be generally defined as being in the NIR range, the far-red range, or in the visible range.

The term "light activation" (also referred to herein as "photoactivation") is used herein to refer to control of a protein activity by application of NIR light of selected wavelengths or removal of light from a fusion protein as described herein. The fusion protein is "activated" when NIR light applied to the photoreceptor causes a change in conformation of the output module of the fusion protein such that it changes the activity of the output module. This change is believed to be caused, at least in part, by rotation of the monomeric output modules with respect to each other such that a desired activity of the fusion protein is changed, e.g., stopped, started, enhanced, or decreased. The term "light activated" (also called "photoactive" in reference to proteins hereof) means a protein capable of being controlled by NIR light to be active or inactive, or more or less active or inactive. Thus, the terms "photoactive proteins" or "photoactivated proteins" also include "photoinactive proteins" or "photoinactivated proteins," respectively.

A "photoactivation ratio" (also referred to as a "light-activation ratio" or "dynamic range") is the ratio of protein activity upon NIR irradiation to protein activity in the dark. In embodiments, the protein activity can be achieved by applying light of selected wavelength to the protein, or by removal of such light. In embodiments, the protein can be made active by applying light of a selected wavelength and can be made immediately inactive by applying light of a different selected wavelength, or can be allowed to become gradually inactive by removing light of said different selected wavelength. In embodiments, the protein can be made inactive by applying light of a selected wavelength and can be made immediately active by applying light of a different selected wavelength, or can be allowed to become gradually active by removing said light of a different selected wavelength. In embodiments, the fusion proteins hereof can be controlled to be substantially completely inactive or substantially completely inactive by the foregoing means (when high light activation ratios are achieved), or can be controlled to be relatively inactive or to be relative active (when low light activation ratios are achieved).

A "fusion site" defines the amino acid of the photoreceptor module that is linked to the specific amino acid of the output module of the fusion protein.

A "linker region" of fusion protein hereof is the α-helical protein region that includes a fusion site. The linker region of the fusion protein may be composed entirely of α-helical regions or partly of α-helical region. Linker regions hereof may be shortened or lengthened using amino acid sequence of the photoreceptor module or artificial sequence in order to cause or improve control of activity of NIRLAHPs by light.

A "plurality" as used herein means two or more.

Microbial photoreceptors, bacteriophytochromes, absorb near-infrared light, which penetrates deep into animal tissues and is harmless. Bacteriophytochromes delivered as genes can be used to control biological activities in live animals via external light sources. However, the lack of understanding of light-induced conformational changes has hindered development of bacteriophytochrome-based optogenetic tools. Here, we show that homodimeric bacteriophytochromes can be engineered to activate heterologous output domains that require homodimerization.

Light has advantages over chemical means of regulating biological processes because it acts noninvasively and provides superior spatial and temporal resolution. Optogenetic approaches that rely on algal and archaeal channel rhodopsins activating specific animal neurons opened up a new era in neurobiology. Photoreceptors of several other types have been engineered to regulate biological processes and used in cell cultures and transparent animals (Pathak et al., 2013; Müller and Weber, 2013). However, application of optogenetic tools in heme-rich animal tissues has been hindered by high scattering and poor penetration of visible light. Light in the near-infrared window (NIRW), which encompasses the spectral region of approximately 680-880 nm, penetrates animal tissues much better than light outside NIRW (Weissleder, 2001). A significant fraction of NIRW light can pass through several cm of human tissues (Wan et al., 1981; Cubeddu et al., 1999; Byrnes et al., 2005), which makes it possible to control biological processes in animals using NIRW light. Absence of photoreceptors of NIRW light in most animal tissues is an additional advantage that makes NIRW light harmless (Piatkevich et al. 2013). This is in contrast to blue light, which is absorbed by flavins and porphyrins, and therefore promotes photooxidative damage (Hockberger et al., 1991).

Phytochromes are photoreceptors that absorb light in the NIRW of the spectrum (Rockwell et al. 2006; Auldridge and Forest 2011; Ulijasz and Vierstra 2011). The photosensory modules of these photoreceptors covalently bind bilin chromophores. Plant and cyanobacterial phytochromes bind phycocyanobilins or phycoerythrobilins, while bacteriophytochromes bind biliverdin IX.

As the first product of heme turnover, biliverdin IXα is naturally present in animal cells, which makes bacteriophytochromes preferred over plant and cyanobacterial phytochromes, whose chromophore synthesis requires dedicated enzymes. Further, absorption wavelength maxima of bacteriophytochromes are red-shifted compared to the absorption maxima of plant and cyanobacterial phytochromes. This results in a 2-10-fold gain in the penetration depth of light through mammalian tissues (Wan et al., 1981; Piatkevich et al., 2013). Up to now, bacteriophytochrome engineering for optogenetic applications has lagged behind the engineering of photoreceptors of other types (Pathak et al., 2013), including engineering of plant phytochromes (Levskaya et al., 2009).

The major obstacle to bacteriophytochrome engineering has been the lack of understanding of the mechanisms though which light induced conformational changes are transduced to regulate output activities (Rockwell et al., 2006; Auldridge and Forest, 2013; Ulijasz et al., 2011; Möglich et al., 2010).

Most or all bacteriophytochromes function as homodimeric enzymes, usually histidine kinases and, more rarely, diguanylate cyclases (DGCs). Enzymatic activities of both histidine kinases and DGCs require precise alignment of two monomers in a homodimer. In case of DGCs, their product, cyclic dimeric GMP (cdi-GMP), is synthesized from two GTP molecules at the interface between two GGDEF domains (Pfam database; [Punta et al., 2012]) responsible for DGC activity. Each GGDEF domain brings a substrate molecule to the catalytic site (Schirmer and Jenal, 2009; Römling et al., 2013). In the inhibited state, the photosensory modules were shown to prevent enzymatic domains from forming a properly aligned homodimer, while light-induced conformational changes restore enzymatically productive domain alignment. We believe the conformational changes are mediated by the α-helical linkers that connect the photosensory modules to the output domains (Yang et al., 2009; Yang et al., 2011) (FIG. 11). Further, in all DGCs whose regulation has been studied at the structural level, enzyme activation has been shown or predicted to occur via alignment of the rigid GGDEF domains rather than via intradomain conformational changes (Schirmer and Jenal, 2009; Römling et al., 2013). Because of these considerations, bacteriophytochromes can regulate diverse output activities that depend on proper alignment of the two output domains.

Here we demonstrate that bacteriophytochrome photosensory modules can indeed regulate heterologous output domains.

Earlier, we and others described naturally occurring blue-light activated ACs whose utility in optogenetic applications in cell cultures and small animal models has been demonstrated (Schröder-Lang et al., 2007; Ryu et al., 2010; Stierl et al., 2011; Weissenberger et al., 2011; Efetova et al., 2013).

However, undesirable effects of blue light and its poor penetration through nontransparent tissues present major obstacles for the use of blue-light activated ACs, which can be solved by IlaCs. The teachings hereof make it possible for those of ordinary skill in the art to engineer new NIRW light-activated optogenetic tools.

Embodiments

Methods are provided herein for producing photoactive fusion proteins based on photoreceptor modules of bacteriophytochromes having a desired activity controllable by near-infrared (NIR) light, said methods comprising the steps:

a. identifying, based on biochemical information, candidate protein output domains that function as homodimers and can be activated by homodimerization;

b. using 3D structures or building 3D models to identify optimal fusion sites and peptide linkers for attaching the heterologous output modules to the bacteriophytochrome photoreceptor module;

c. producing a plurality of DNA molecules (a DNA library), each encoding a monomer of the homodimeric fusion protein that has at least one unique fusion site or linker sequence;

d. screening the DNA molecules for their ability to produce homodimeric photoactive fusion proteins capable of performing the desired activity in a test organism, wherein the screening is done by transforming the test organism designed to respond to the desired activity with the DNA library; allowing the expressed fusion proteins to spontaneously bind biliverdin IXα and form homodimers; applying light of selected wavelengths to the transformed organisms; and comparing the level of said desired activity of the expressed fusion proteins in the test organism in the dark and in the light;

e. optionally subjecting fusion proteins that have NIR light-activated activities identified by screening to random mutagenesis and subsequent screening (as described above) for mutant derivatives with improved qualities, e.g., low activity in the dark and high photoactivation ratio; and f. purification, and spectral and biochemical characterization of fusion proteins produced by screening to assess their activity levels and photoactivation ratios in vitro.

Candidate output activity to be regulated by NIR light resides within a homodimeric protein. Desired output activity is revealed upon homodimerization, while monomeric output domains should have no or low, background, activity.

Analysis of existing 3D structures and structure modeling of proteins having a desired activity can be performed to identify suitable output modules. The N-terminal boundaries of the functional output domains are defined, and a distance between the N-terminal boundaries is estimated based either on 3D structures or models of 3D structures. This distance is compared to the distance between the C-termini of α-helices extending from the PHY domains of the bacteriophytochome photoreceptor module (PAS-GAF-PHY) homodimer that will be used for fusion. These distances need to be within several angstoms (Å) from each other. Should the distances deviate by more than approximately 10 Å, prior to designing fusion sites, adjustments are made by increasing or decreasing the length of α-helixes extending from the PHY domains of the bacteriophytochome photoreceptor module. Said adjustments will change the distance between the C-termini of α-helixes to better match (within several Å) the distance between the N-terminal boundaries of the functional homodimeric output domains. Structures of many proteins having desired activities, protein 3D structure modeling approaches and software are known to the art. Extension of α-helixes may rely on native sequence of the bacteriophytochrome protein or on artificial amino acid sequences known to form α-helixes. Should modification of the lengths of α-helixes extending from the PHY domains be insufficient for bringing the distances between said α-helixes and the N-terminal boundaries of the homodimeric output domains in the proximity of several Å, positions of the N-terminal boundaries can be adjusted, i.e., shortened or extended, provided that such adjustments preserve activity of the homodimeric output modules. Prior to constructing fusion proteins, activities of homodimeric output modules are verified in vitro.

Once the fusion site is chosen, a fusion encoding the chimeric protein is made and tested for desired activity and photoactivation ratio. Typically, a plurality of fusions (a DNA library) is made where the N-terminal position of the output domain is fixed, while the α-helical linkers extending from the PHY domain of the bacteriophytochrome photoreceptor module are made to differ from each other by a single amino acid. Once a fusion protein having the desired NIR light-activated or NIR light-inactivated activity is identified, it has been found that shortening or lengthening the α-helices extending from the PHY domain by one or two α-helical turns will form additional proteins that are also light-activated (or light-inactivated). An α-helical turn, approximately 3.6 amino acids, can be approximated by 3 and 4 amino acid extensions and deletions.

The bacteriophytochrome photoreceptor module that provides sensitivity to light in embodiments is a photoreceptor module from the *Rhodobacter sphaeroides* BphG1 protein comprising PAS-GAF-PHY domains. The photoreceptor module binds its chromophore, a biliverdin IXα, in vivo and in vitro due to intrinsic biliverdin ligase activity.

The output module can be selected from enzymes and other proteins that have a desired biological activity, e.g., enzymatic activity, or ability to bind DNA, RNA or other proteins. In embodiments, the output modules can include protein kinases, proteases (including caspases), nucleotidyl cyclases, nucleases (including recombinases), DNA-binding and RNA-binding protein modules, and others that are activated by homodimerization.

Some photoactive fusion proteins can be activated or their activity can be enhanced by the application of light of an activating wavelength. They can be inactivated, or their activity can be reduced by the absence of light or by the application of light of an inactivating wavelength. Some photoactive proteins can be active or show enhanced activity in the dark or reduced light, and be inactivated or show reduced activity when light of an inactivating wavelength is applied. The "absence of light" can mean the absence of all light (i.e., darkness), or can mean the absence of light in a selected wavelength range that causes a change in the conformation of the bacteriophytochrome photoreceptor module.

In embodiments, in which the fusion protein is in a stable active form (i.e., the output module is in a conformation such that it performs a desired activity when no NIR light is applied), when NIR light of a first wavelength is applied, the conformation of the output module changes and the output module immediately becomes inactive. In such embodiments, the inactive state is relatively unstable. When NIR light of a second wavelength is applied to the fusion protein, it immediately reverts to the stable, active form. If light of the second wavelength is not applied, then the fusion protein gradually reverts to its stable, active form.

In embodiments, in which the fusion protein has a stable inactive form, the opposite is true: the fusion protein is inactive until NIR light of a first wavelength is applied. Then it immediately becomes active. It can be immediately inactivated by application of NIR light of a second wavelength or it can be gradually inactivated by not applying NIR light of the second wavelength.

Thus, in embodiments the desired activity is increased by the application of NIR light of a selected wavelength. In embodiments the desired activity is decreased by the application of NIR light of a selected wavelength. In embodiments the desired activity is gradually decreased or gradually increased by ceasing to apply NIR light of a selected wavelength. In embodiments the desired activity is immediately increased or decreased by the application of NIR light of a selected wavelength. Suitable selected wavelengths are determined by the spectral properties of the bacteriophytochrome photoreceptor module and readily ascertained by those of ordinary skill in the art without undue experimentation.

It is to be understood that the terms "active" and "inactive" in the foregoing explanation are relative and include complete activity of the protein to complete inactivity of the protein (complete "on/off" modes) as well as relative activity or inactivity of the proteins, i.e., the fusion proteins can have high activation ratios, low activation ratios, or activation ratios between high and low. In embodiments the fusion proteins can be controlled by light to have high ratios of activity to inactivity or of inactivity to activity under the control of light of appropriate wavelengths. High ratios are defined herein as ratios of about 2:1 or greater, in embodiments, about 5:1 to about 10:1 or greater. Low ratios are less than about 2:1.

In embodiments, the fusion proteins to be screened can be produced in test organisms already having endogenous chromophore molecules that will bind with the fusion proteins as they are expressed.

In embodiments where no or insufficient chromophore molecules are endogenously available in the test organisms, in addition to producing DNA molecules encoding the designed fusion proteins and expressing them in test organisms, DNA encoding a heme oxygenase can also be expressed in the test organisms, e.g. *Rhodobacter sphaeroides* heme oxygenase BphO1 (RSP_4190) (Tarutina et al., 2006). The heme oxygenase degrades heme that is present in the test organisms to produce biliverdin IXα chromophore, which then binds to the expressed fusion proteins and make them photoactive. The DNA encoding the fusion proteins can be introduced into the test organisms on the same expression cassette as the DNA encoding heme oxygenase. Suitable expression cassettes comprising DNA for expression under control of appropriate regulatory elements such as promoters are known to the art.

Test organisms for use herein can be any organisms known to the art in which the level of the desired activity can be detected, including cultured organisms selected from the group consisting of *E. coli*, yeast, plant, or animal cells selected or modified so as to detectably exhibit the level of activity of the expressed fusion proteins under control of NIR light.

When using the fusion proteins produced by the present methods to treat living cells or organisms by controlling processes in these cells or organisms, there can be sufficient endogenous chromophores in the organisms to bind with the expressed fusion proteins, or if not, the organisms can be transformed with a heme oxygenase gene that will be expressed to produce heme oxygenase, which degrades heme that is present in the organisms to produce the chromophore molecules that will bind with the expressed fusion proteins in vivo.

In embodiments, additional fusion proteins controllable by NIR light can be produced by mutagenizing genes encoding "first-generation" NIRLAHPs to create fusion proteins that have lower background activities and higher photoactivation ratios. Mutagenesis was found to improve such protein parameters when applied to DNA encoding the α-helical region linking the PHY domain with the output domain, as well as when applied to the full-length gene encoding a fusion protein.

Thus, fusion proteins that are found to be controllable by NIR light can be the basis for designing additional candidate fusion proteins by mutagenesis and repeating the steps of producing DNA encoding the additional fusion proteins, transforming suitable organisms with this DNA, expressing the DNA, and screening the resultant fusion proteins for additional fusion proteins controllable by NIR light. DNA molecules encoding such additional designed fusion proteins are then made, expressed in test organisms, and screened for their levels of the desired activity.

To further enhance the photoactivation ratios of fusion proteins, the second generation fusion proteins generated by mutagenesis of the first-generation fusion proteins can be mutagenized further to create improved NIRLAHPs. DNA molecules encoding such further designed fusion proteins are then made, expressed in test organisms, and screened for their levels of the desired activity.

The methods hereof comprise selecting or constructing a suitable organism for producing and screening the plurality of DNA (DNA library) encoding NIR light-activated fusion proteins. Any suitable organism known to the art for expression of fusion proteins can be used, so long as the level of the desired activity of the proteins in the organism can be detected. In embodiments, the level of the desired activity can be directly monitored by means known to the art, e.g., by detecting the blue color of β-galactosidase when it is a marker for a protein produced as the desired activity of the fusion protein. In embodiments, the test organism can be modified as is known to the art to allow detecting of the desired activity of the fusion protein. For example, the test organism can be engineered to allow detection of the desired activity by mutagenesis to prevent it from producing a substance that it would normally produce, so that it can only produce this substance if it expresses an active fusion protein.

The photoactive fusion protein can have any activity known to the art. Typically the activity involves control of a process in vivo such as a metabolic process, signal transduction, cell apoptosis, cell proliferation, cell adhesion, or cell differentiation. In embodiments, the photoactive fusion protein is selected from the group consisting of a light-activated nucleotidyl cyclase, such as adenylyl cyclases (also known as adenylate cyclases) or guanylyl cyclase (also known as guanylate cyclases), and a light-activated uncleavable procaspase-3.

NIR photoactive fusion proteins are also provided herein. Such proteins can be produced by the methods described above, or by methods analogous thereto that can be designed and carried out by those of ordinary skill in the art without undue experimentation.

Further provided herein are recombinant DNA molecules encoding the homodimeric fusion proteins described herein. Expression cassettes comprising such DNA molecules under control of appropriate regulatory elements are also provided.

Also provided herein are methods for controlling an in vivo process in a host, which is a living cell or organism. The method comprises:

a. introducing into the cell or organism or selected portion of the organism a DNA sequence encoding a homodimeric fusion protein comprising a bacteriophytochrome photoreceptor module and a heterologous output module capable of modulating the desired process;
b. introducing into the cell or organism a DNA sequence encoding a heme oxygenase capable of producing biliverdin IXα, if the endogenous level of biliverdin IXα in the cell or organism is insufficient for photoactivation;
c. providing a source of heme (the substrate for heme oxygenase), if the host cell or organism does not contain sufficient endogenous levels of heme; or providing biliverdin IXα;
d. allowing the fusion protein and heme oxygenase, where applicable, to be expressed in the host; and
e. applying NIR light of a selected wavelength to the host or preventing NIR light of a selected wavelength from reaching the host; thereby modulating the process under control of NIR light.

Methods of introducing DNA into selected portions of organisms are well-known to the art. Methods for selectively expressing DNA in chosen portions of an organism are also well-known to the art, including use of tissue-specific promoters. These techniques can be combined with the application of light to selective portions of an organism to control expression of the homodimeric proteins hereof in desired tissues and organs.

The in vivo process can be selected from the group consisting of metabolic processes, signal transduction, cell apoptosis, cell proliferation, cell adhesion, and cell differentiation.

The photoreceptor module can be as described above, e.g., that of *Rhodobacter sphaeroides* BphG1 protein.

Detailed Discussion

The engineering principles disclosed herein are applied to select and optimize NIR light-activated homodimeric proteins (NIRLAHPs). These proteins can be used to turn on (or turn off) desired activities in transgenic animals, plants or microbes.

Bacteriophytochromes can significantly expand the range of optogenetic applications: (i) They absorb light of the far-red/NIR spectrum (Rockwell et al., 2006, FIG. 1B), which penetrates animal tissues much deeper than visible light sensed by currently used photoreceptors (Cuberddu et al., 1999; Wan et al., 1981; Byrnes et al., 2005). (ii) NIR light is harmless; for example, it is currently used in human optical imaging and deep-tissue phototherapies (Fang et al., 2009; Desmet et al., 2006). (iii) The biliverdin chromophore of bacteriophytochromes is the first product of heme breakdown and thus is naturally produced by most animal cells (Rockwell et al., 2006). If insufficient, biliverdin (which is nontoxic in small doses) can be directly injected (Shu et al., 2009) or supplied by a bacterial heme oxygenase. (iv) Phytochromes can be instantly turned "off" (i.e., photoinactivated) by longer wavelength light (Rockwell et al., 2006), which provides for excellent temporal control. (v) Lastly, recently (far-red light absorbing) phytochrome-based fluorescent proteins have been expressed in mice and used for whole-body imaging, which proves that phytochromes expressed in deep tissues can be activated by external light sources in small mammals (Shu et al., 2009). In sum, NIR light-activated proteins can significantly broaden the range of optogenetic applications and allow researchers to use these approaches in the mammalian models of development and diseases as well as in other organisms.

Bacteriophytochromes function as homodimers. The light-induced conformational changes in the photosensory module of one monomer are presumed to rotate its output domain and bring it into proximity with the output domain of the second monomer, thus generating an active conformation of the homodimer. Natural bacteriophytochromes have different homodimeric outputs, e.g., His-kinases and diguanylyl cyclases.

Any bacteriophytochrome can be used in the methods and homodimeric proteins provided herein provided it is responsive to light. A few proteins classified as bacteriophytochromes may not respond to light. Responsiveness to light can be tested by those of ordinary skill in the art without undue experimentation.

In addition, those of ordinary skill in the art can determine the most effective wavelengths for controlling the activity of the homodimeric proteins provided herein without undue experimentation by means known to the art and described herein, such as spectroscopically observing differences between the spectra of the homodimeric proteins in light and dark (Rockwell et al., 2006).

This disclosure illustrates engineering of photoactivated versions of nucleotidyl cyclases and executioner caspase. Engineering principles for constructing NIR light-activated homodimeric proteins are provided. Since a large number of signaling proteins function as homodimers, NIR light-induced protein homodimerization can be used to control a variety of cellular functions including metabolic processes, signal transduction, cell apoptosis, differentiation, proliferation, transformation and adhesion.

This disclosure also illustrates the use of the homodimeric proteins hereof for controlling neuronal activity in the roundworm *Caenorhabditis elegans*. The homodimeric proteins hereof can be used to control other in vivo processes as described above, for example through the use of light-activated adenylate cyclases to control production of cAMP, which in turn controls are wide range of metabolic processes. See, e.g., Chin et al., 2002.

In addition, the proteins can be used to control metabolic processes in a wide range of living organisms. Bacteriophytochrome photosensors have also been used to engineer monomeric fluorescent proteins expressible in mammals (Shu et al., 2009). The expression of the engineered homodimeric proteins provided herein can be applied to any desired cell or organism by one skilled in the art without undue experimentation using the teachings hereof as well as art-known techniques of molecular biology. Specific techniques for transformation applicable to specific cells and host organisms, are well-known to the art. In addition, methods of introducing cells capable of expressing the homodimeric proteins hereof into host organisms are well known to the art. Those of ordinary skill in the art can determine effective levels of expression to accomplish desired metabolic results without undue experimentation using art-known knowledge and the teachings herein.

The methods and engineered homodimeric proteins provided herein can be used in research investigating the pathways, neural and chemical involved in various metabolic functions in vivo, and for treatment of various disease conditions including cancer, neurological and cardiac conditions and other diabetes and other hormonal dysfunctions. It can also be used in industrial biological processes to control the output of desired products.

This disclosure illustrates engineering of NIRLAHPs using the BphG1 protein from *R. sphaeroides*. However, numerous bacteriophytochromes are present in the genomes of microbes, primarily in bacteria. Because they likely undergo similar light-induced conformational changes to those that occur in BphG, these bacteriophytochromes can also be used as sources of photoreceptor modules for protein engineering.

Construction of photoactivated fusions starts with identification of output activities known to be activated by homodimerization. Subsequently, analysis of 3D structures (or structural models) of the photosensory module and homodimeric output module is undertaken. A fusion point for creating photoactivated chimeric proteins is based on using approximately the same distance (in three-dimensional space) between the C-termini of the α-helices extending from the PHY domains of the homodimeric photosensory modules as the distance between the N-termini of the homodimeric output modules. These distances are derived from 3D structures (X-ray and NMR) or structural models built based on 3D structures. The α-helices extending from the PHY domains can be shortened or extended to accommodate the N-termini of the output module. The fusions can occur at different boundaries of the output module; therefore, several fusion sites are tested to identify fusion proteins with optimal parameters, i.e., high photoactivation ratio (the ratio of protein activity in the light to that in the dark, also known as dynamic range) and low activity in the inactive state (which is the dark state for photoactivated proteins, or lit state in the photoinactivated proteins). Our analysis of an engineered NIRLAHP-adenylyl cyclases (where the output module is the adenylyl cyclase domain of the CyaB1 protein from *Nostoc* sp.) suggests that the light-induced conformational changes in the photosensory domain of a bacteriophytochrome monomer result in a movement, that may involve rotation, of its output domain that brings it in proximity with the output domain of the second monomer, thus generating an active homodimer.

The relative positions of the output domain monomers depend on the phase of the α-helices that link the PHY domains of the photosensory module to the output domains. The output domains that are linked on the same side of the α-helices display similar light responsiveness. For example, several light-activated fusion proteins have been obtained that differ from each other by multiples of 3 or 4 residues, which corresponds to one, two or more α-helical turns, where one α-helical turn is approximately 3.6 amino acid residues. The torque generated by the presumed rotation of the photosensory module following photon absorption is believed to change mutual arrangement (possibly via rotation) of the output domains. For transfer of the torque to the output domains, unstructured elements (e.g., loops) preceding the more rigidly structured elements of the output domains should be minimized.

Once a first-generation NIRLAHP is obtained, its photoactivation ratio can be improved via mutagenesis (e.g., via error-prone PCR mutagenesis using the whole fusion protein as a template at the rate of several mutations per gene, or via integration of degenerate synthetic DNA sequences).

NIRLAHPs possessing lower dark activities and higher photoactivation ratios, compared to the first-generation NIRLAHPs, can be identified following the same mutagenesis and screening procedures.

Selection and/or screening for the first-generation NIRLAHP of its class as well as identification of mutants with maximal photoactivation ratios can be achieved by using specifically designed microbial or animal cells. For example, screening for a light-activated adenylyl cyclase is done in the *E. coli* mutant impaired in the cya gene that encodes a native adenylyl cyclase.

Cyclic nucleotides are universal second messengers that control various important biological processes. However, precise roles of cAMP and cGMP in many physiological processes and diseases remain unknown. A number of drugs for chronic obstructive pulmonary disease, bone marrow transplant rejection, and cancer increase cellular cAMP, which in turn decreases inflammation (reviewed in Serezani et al., 2008). Some of the primary signals inducing cAMP synthesis in cells include epinephrine, norepinephrine, histamine, serotonin, and certain prostaglandins (Landry et al., 2006). The photoactivated adenylyl cyclase allows understanding of signaling pathways with higher precision than that provided by the use of hormones. Blue-light-activated adenylyl cyclase from *Euglena gracilis* (Iseki et al., 2002) and *Beggiatoa* sp. (Ryu et al., 2010; Stierl et al., 2011) can be applied to study various biological processes in cell cultures and animals transparent to light, e.g. zebrafish. The NIR light version of adenylyl cyclases allows researchers to study cAMP-signaling in both transparent model organisms and, importantly, organisms that are non-transparent to visible light, e.g. red-blooded animals.

The near-infrared light version of guanylyl cyclase can be made by site-directed mutagenesis of as few as 2-3 amino acid residues in the adenylyl cyclase (ACyc) domain as known in the art (Ryu et al., 2010)

Figure 2:
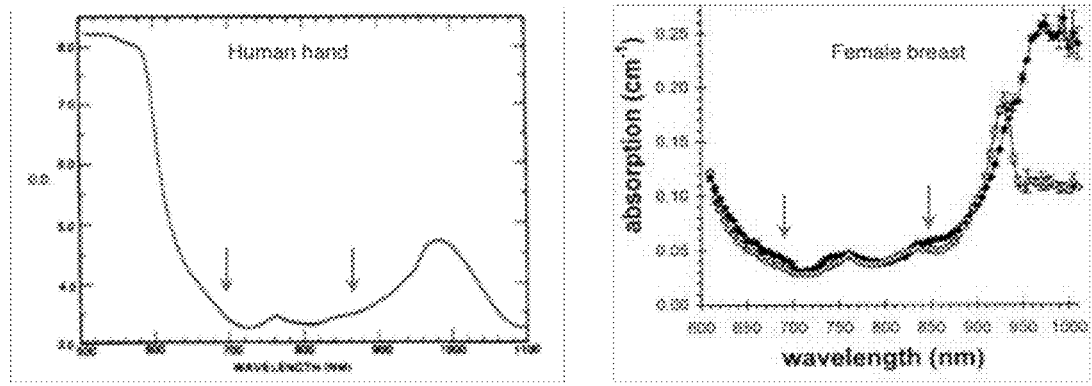
FIG. 2 (image from Cubeddu et al., 1999) illustrates major advantages of biliverdin IXα containing bacteriophytochromes as photoreceptor modules for engineering light-activated proteins for use in mammals. These advantages include deep penetration of NIR into mammalian tissue, lack of toxicity, ubiquity of biliverdin IXα in mammalian tissue (as natural product of heme turnover) and instant photoinactivation. Left top panel: absorbance of light passing through flesh of a human hand. Right top panel: the absorbance of human breast tissue at different wavelengths. Arrows approximately delimit the range of the spectrum with low light absorption by human tissues, which provide for deeper light penetration.
Figure 3:
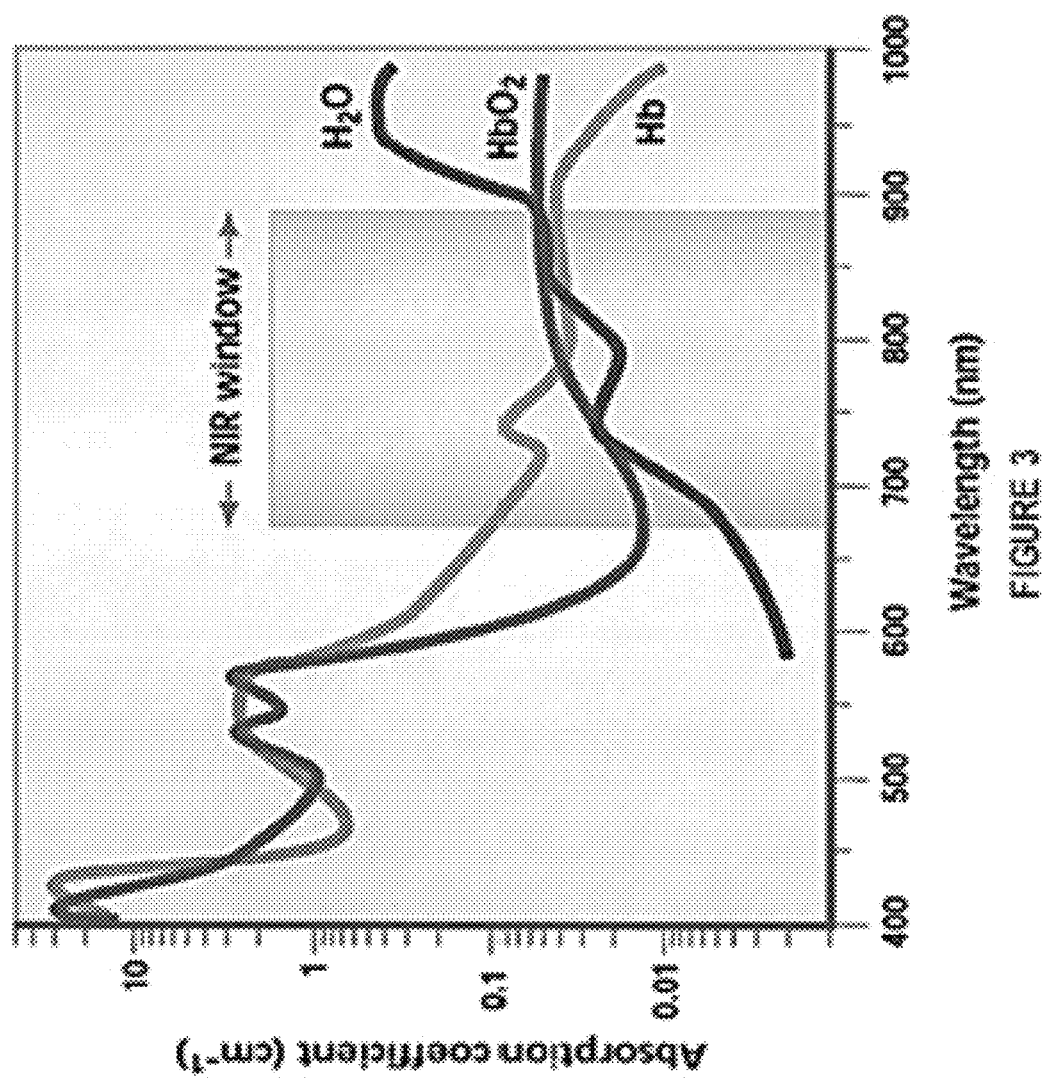
FIG. 3 (image from Weissleder, 2001) shows the "NIR window" from about 670 nm to about 890 nm, where cumulative absorption by three major light-absorbing components of flesh in red-blooded animals, deoxyhemoglobin (Hb), oxyhemoglobin (HbO$_2$) and water (H$_2$O), is lowest. The NIR window identifies the range of wavelengths that can be used for deepest penetration through mammalian tissues. Bacteriophytochrome absorption peaks fall into the NIR window.

Photoactivated caspases, are another biological tool disclosed herein. They allow researchers to conduct targeted cell/tissue killing in vivo using NIR light, and are applicable in many areas of biology and medicine, particularly in tumor biology, immunology and developmental biology. Currently-available approaches that target cells for killing, e.g., laser ablation, and chromophore-assisted light-inactivation with chemical or genetically encoded photosensitizers (Jacobson et al., 2002; Bulina et al., 2006), are harsher (i.e., damage nearby cells/tissues), less precise and/or poorly applicable to mammalian models. A photoactivated caspase, whose gene can be delivered in tumors (e.g., by recombinant viruses, bacteria or nanoparticles), can be used as a readily controllable cancer gene therapy. It can be used in isolation or in combination with already-existing cancer treatments (e.g., cytotoxic drugs). A blue-light activated executioner caspase-7 has recently been engineered and shown to efficiently kill cells in cell culture in response to blue light (Mills et al., 2012). However, the utility of blue-light activated caspase, as well as other blue-light activated proteins is limited in red-blooded animals because of low light penetration through animal tissues (FIGS. 2, 3). Therefore, a NIR-activated caspase represents a transformative improvement that enables its use in animal models of disease and development.

Engineering and Optimizing Near-Infrared Light-Activated Nucleotidyl Cyclases.

Cyclic nucleotides are universal second messengers that control a variety of processes including cell growth and differentiation, blood glucose levels, cardiac contractile function, learning, memory, and other processes known to the art. The ability to activate cAMP and/or cGMP synthesis in desired cells at specific development/disease times is used to provide new and important mechanistic insights into cyclic nucleotide signaling.

Figure 7:
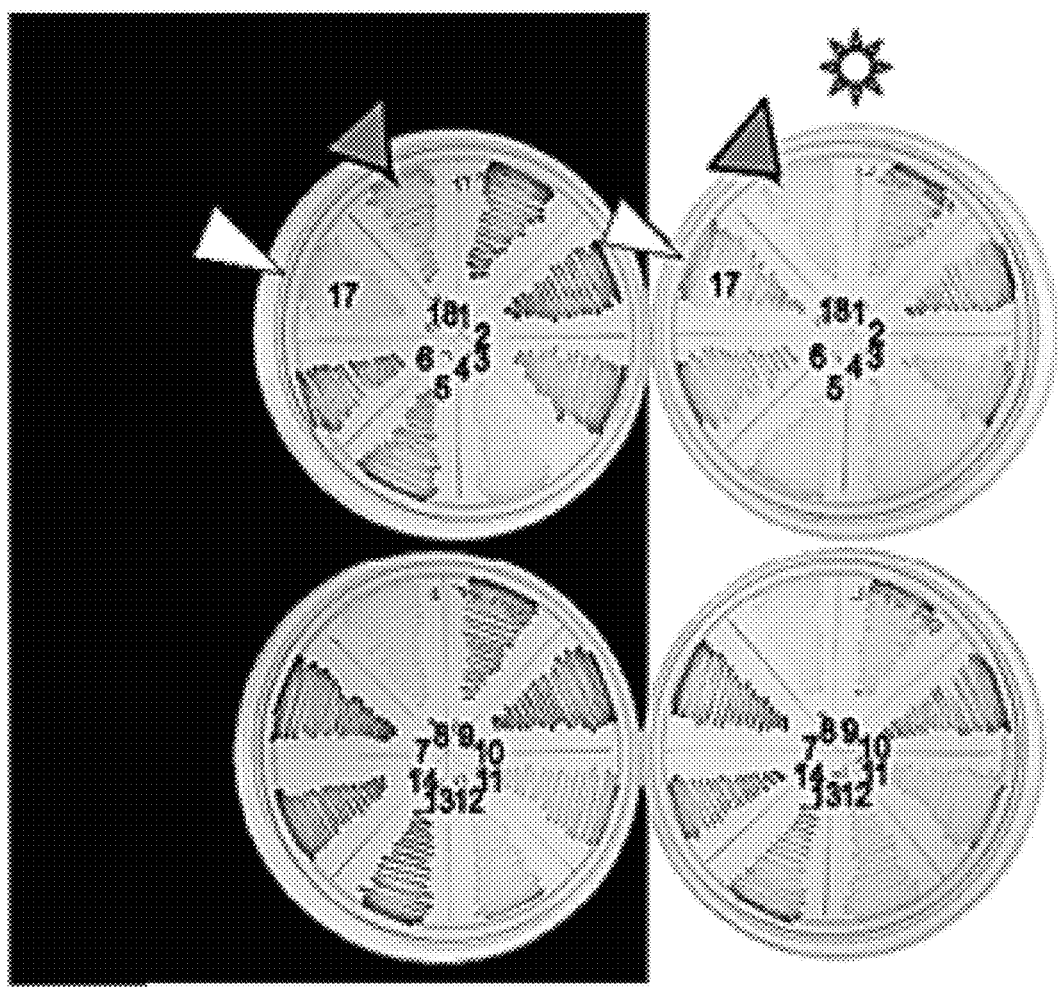
FIG. 7 illustrates XGal indicator plates containing representative *E. coli* clones, each having a gene encoding a different (numbered) fusion adenylyl cyclase protein construct, grown either in the dark (left panel) or in the light (right panel). Blue color indicates how each clone responds to light. The white arrowhead points to the clone containing a light-activated adenylyl cyclase including the sequence: MAQRTRAELERKEVT [SEQ ID NO:6] the black arrowhead points to one of the light-inactivated adenylyl cyclases, RlaC18, including the sequence MAQRTRAELARLRHYDERKEVT [SEQ ID NO:1].
Figure 8:
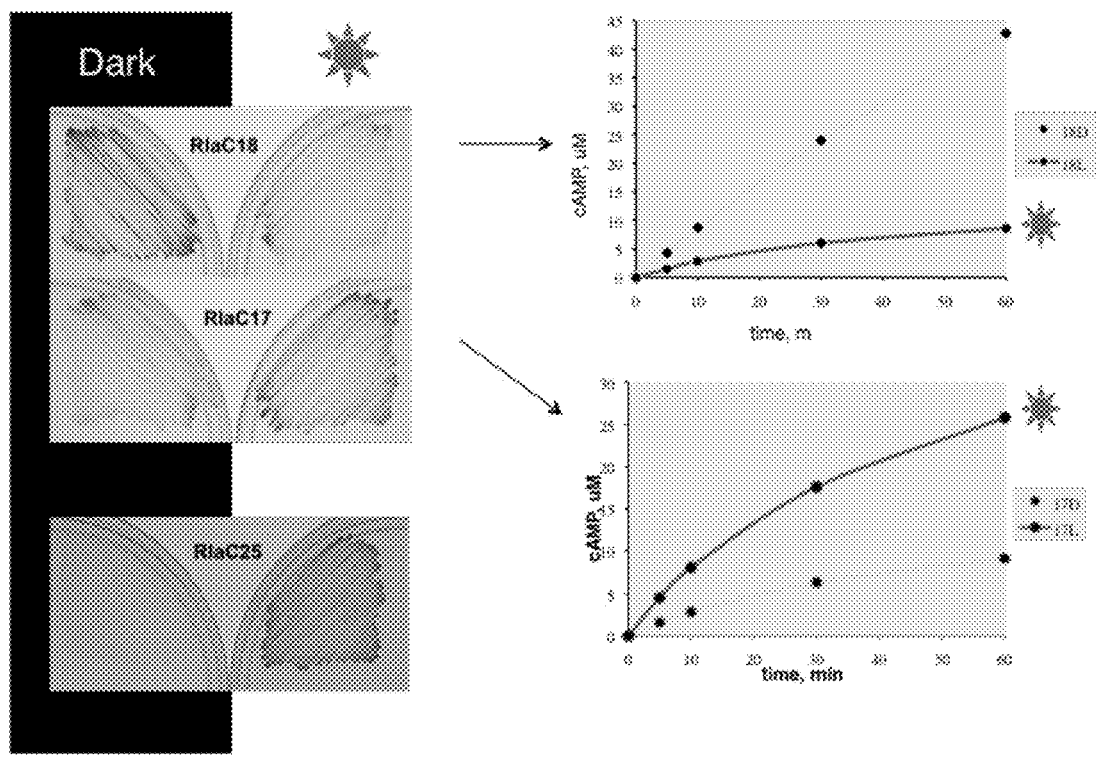
FIG. 8 shows images of *E. coli* clones containing selected and relevant sequences for light-activated RlaC17 (SEQ ID NO:6), RlaC25, MAQRTERKEV T [SEQ ID NO:10] and light-inactivated RlaC18, (SEQ ID NO:1) fusion adenylyl cyclase proteins grown in the dark and light, along with adenylyl cyclase activities of the purified proteins measured under light and dark conditions in vitro.
Figure 8:
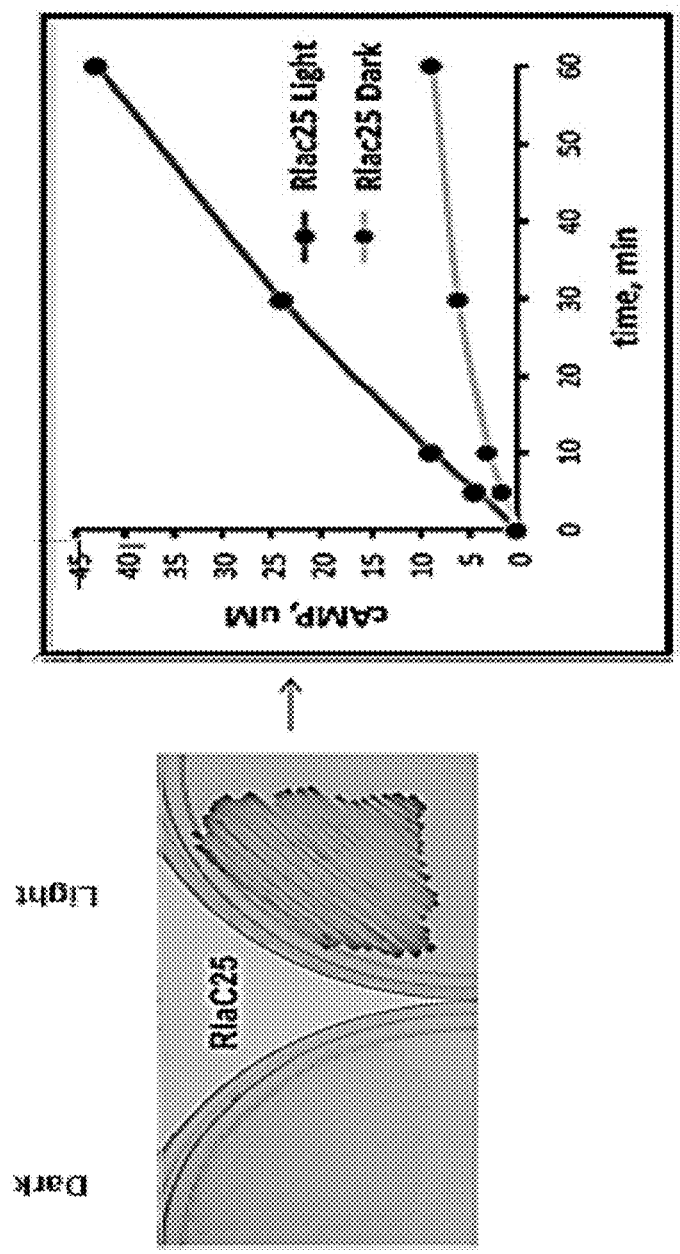

As shown herein, bacteriophytochrome photosensory modules were engineered to activate heterologous outputs. In an embodiment hereof, to construct NIR light-activated nucleotidyl cyclases, the diguanylyl cyclase GGDEF domain from the photoactivated diguanylyl cyclase, designated BphG, from *Rhodobacter sphaeroides* was replaced with a distantly related adenylyl cyclase (ACyc) domain from *Nostoc* sp. protein CyaB1 resulting in the production of photoactivated adenylyl cyclase, designated RlaC (FIG. 7-9). The first-generation adenylyl cyclases were mutagenized to identify variant enzymes with the highest photoactivation ratio and lowest activities in the dark. Optimized adenylyl cyclase is used as a template to engineer a NIR light-activated guanylyl cyclase as described by Ryu et al. (2010).

Engineering and Optimizing Near-Infrared Light-Activated Executioner Caspases.

Executioner (effector) caspases are terminal cysteine proteases initiating apoptosis (programmed cell death). An engineered photoactivated executioner caspase is useful to induce apoptosis in desired cells or tissues of recombinant animals expressing it in specific tissues. A gene for a photoactivated caspase can also be delivered to tumors and used in noninvasive cancer gene therapy. In an embodiment hereof, a derivative of the executioner caspase, procaspase-3, which is activated by homodimerization, is engineered using principles developed from engineering and optimizing near-infrared light-activated nucleotidyl cyclases to construct a near-infrared light-activated caspase. All engineered enzymes are biochemically characterized in vitro. Prioritized constructs are moved into *Drosophila melanogaster*, mice and other organisms.

The following description of various specific embodiments is exemplary in nature and is in no way intended to limit the scope of the claims hereof. In embodiments, art-known equivalents of exemplified components, materials and method steps can be substituted for those specifically described herein and these embodiments are considered to fall within the scope of the claims. Embodiments including less than all the components, materials and method steps of embodiments specifically described herein are also considered to be encompassed within this disclosure.

Figure 1:
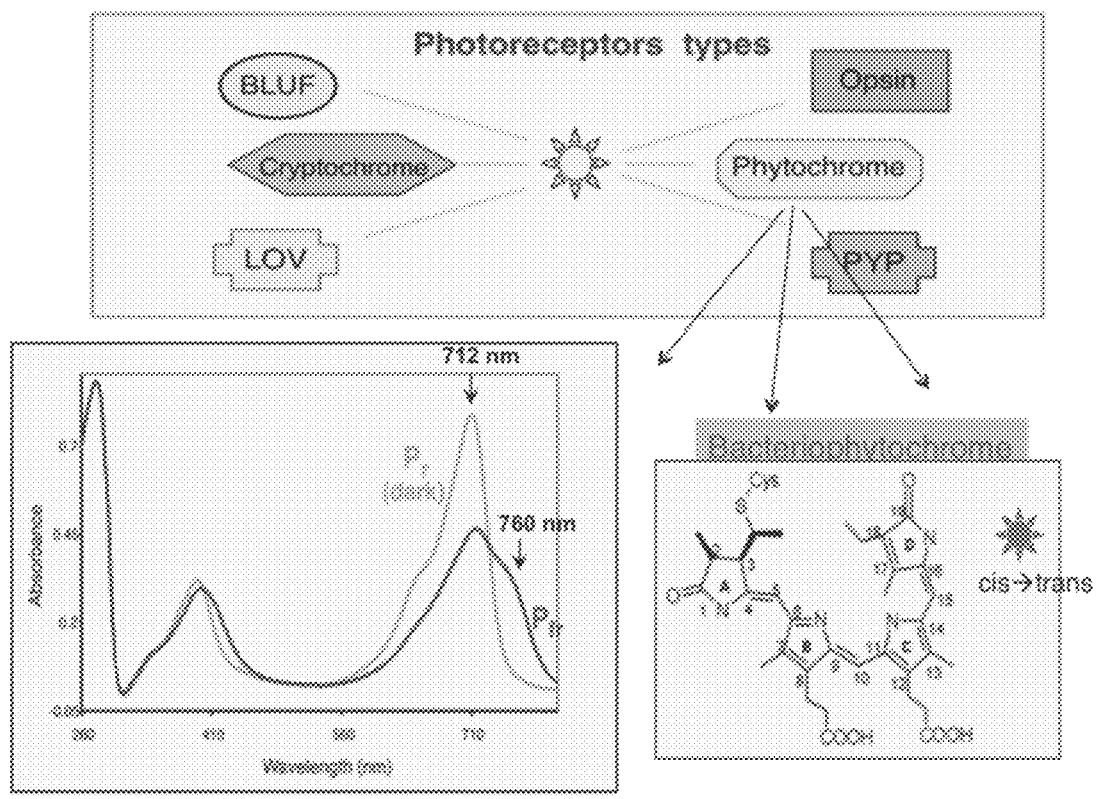
FIG. 1 shows six major photoreceptor types (Gomelsky & Hoff, 2011) (top panel) including a subclass of phytochromes known as bacteriophytochromes. The photoreceptor module from the BphG1 protein from *Rhodobacter sphaeroides* (Tarutina et al., 2006) was used into illustrate the present methods. The molecular structure of the chromophore of the BphG1 protein (biliverdin IXα) is shown in the lower right panel. The lower left panel shows light-induced spectral changes in the BphG1 protein. The protein exists in the "dark" (Pr) form (absorption maximum 712 nm) when it is not exposed to light or irradiated with light of ~740-780 nm. Upon irradiation with light of ~650-715 nm, the protein is converted to the "lit" (Pfr) form (absorption maximum ~760 nm).
Figure 4:
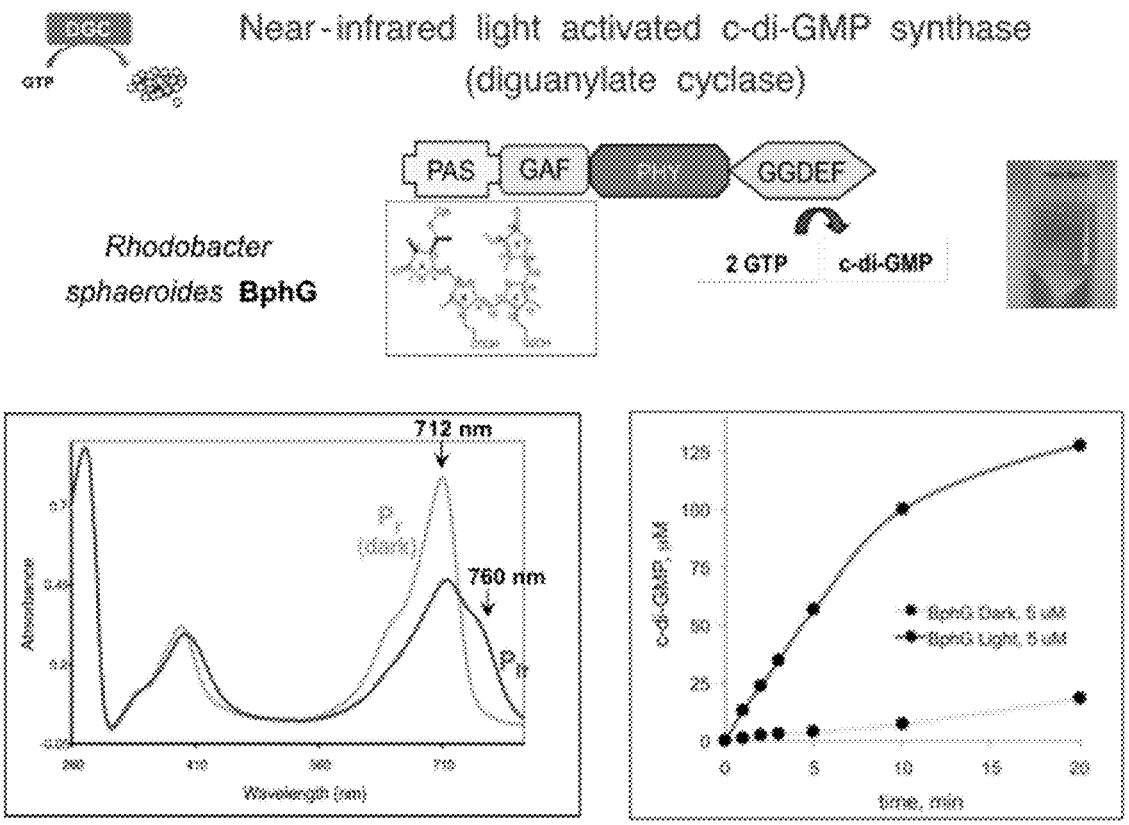
FIG. 4 illustrates protein domain architecture (top panel) as well as spectral and enzymatic properties (bottom panel) of the BphG protein used for protein engineering. Top panel, *R. sphaeroides* BphG (PAS-GAF-PHY-GGDEF), a derivative of BphG1 (PAS-GAF-PHY-GGDEF-EAL) lacking the EAL domain (Tarutina et al., 2006). BphG converts two guanosine triphosphate (GTP) molecules into cyclic dimeric GMP (c-di-GMP) by means of a diguanylate cyclase activity of the GGDEF domain (Ryjenkov et al., 2005). Bottom panel, left: spectral properties of BphG (same as in FIG. 2). Bottom panel, right: synthesis of c-di-GMP by *R. sphaeroides* BphG in vitro, in the dark (grey line) and in the light (black line). BphG has an approximately 10-fold photoactivation ratio (relative activity in the light divided by relative activity in the dark).

FIG. 1 (top panel) depicts six major types of photoreceptors (molecules that organisms use to detect light): opsins, which are human retinal photosensors and rhodopsins of various microbes; cryptochromes, which are blue light-sensitive flavoproteins found in plants, animals and microbes; photoactive yellow protein (PYP) photosensors, which are found in certain bacteria; photoreceptors of blue-light using flavin adenine dinucleotide (BLUF) and Light, Oxygen, or Voltage sensing (LOV) types, which are plant and bacterial photoreceptors; and phytochromes, which are used by plants and microbes and are sensitive to light in the red-to-NIR region. Work done to illustrate the presently-claimed methods was done using a bacteriophytochrome, a subclass of phytochromes that covalently bind biliverdin IXα as a chromophore (a molecule bound to the photoreceptor protein that detect slight and cause a conformational change in the protein when hit with a photon of light). The bacteriophytochrome (Bph) used herein was *Rhodobacter sphaeroides* BphG, which converts two guanosine triphosphate (GTP) molecules into cyclic dimeric guanosine monophosphate, c-di-GMP. As shown in the lower left panel of FIG. 1, the dark form of BphG, has a protein conformation designated Pr, which is present in the dark or absence of 650-715 nm light. When light having a wavelength between about 650 and about 715 nanometers strikes the chromophore, it causes a rearrangement of the molecule to an isomeric form designated as far-red, Pfr, conformation, in which the double bond (between C15 and C16) shifts from the cis to trans conformation. The protein absorbs light maximally at 712 nm resulting in the red-shifted, Pfr, form, whose diguanylyl cyclase activity is approximately 10-fold higher compared to the activity of the Pr form, as shown in FIG. 4. The chromophore of the bacteriophytochrome has the chemical structure depicted in the lower right panel of FIG. 1.

Once formed upon irradiation, the Pfr form of BphG is fairly stable. In the dark it spontaneously converts to the Pr form in approximately 45 min (Tarutina et sl., 2006). If light of about 760 nm is applied, the Pfr form is converted to the Pr (dark) instantly. This reversible photoconversion feature is a unique to phytochromes.

The present methods are especially useful for application in humans and other mammals because mammalian flesh is relatively transparent to far-red/NIR light. As shown in FIG. 2, left panel the absorption of light by a human hand decreases as the wavelength of the light changes from blue to far-red and NIR light, being at its lowest between about 680 to about 890 nm, in the so-called "NIR window" (FIG. 3). FIG. 2, right panel shows absorption of light in female breast tissue, again being minimal in the NIR window. The light in the NIR window can penetrate deeply into the body (many centimeters). The light in the NIR window is harmless because there are no chromophores in animals that absorb in the NIR window.

The main advantages of bacteriophytochromes in use in optogenetics are that their chromophore, biliverdin IXα, is made in mammals, where, as indicated in FIG. 2, it is produced as a natural breakdown product of heme. For use of the chimeric proteins hereof in mammals, there is no need for a step of administering the chromophore separately. Bacteriophytochromes can be instantly photoinactivated, e.g., by applying light of 750-780 nm for BphG. This provides for superior, compared to other photoreceptor types, temporal regulation of output activities of chimeric bacteriophytochromes.

In embodiments when using the fusion proteins hereof for treating an organism, the organism will produce sufficient chromophore molecules for effective use of the NIR-light-controlled fusion protein. However, if biliverdin Ixa is insufficient in a particular tissue or animal model, it can be administered externally (it is nontoxic to animals at low doses), or it can be synthesized by heme oxygenase that can be delivered as a gene on the same gene delivery platform as the chimeric bacteriophytochrome.

FIG. 3 shows the "NIR window" from about 670 nm to about 890 nm, where cumulative absorption by three major light-absorbing components of flesh in red-blooded animals, deoxyhemoglobin (Hb), oxyhemoglobin (HbO$_2$) and water (H$_2$O), is lowest (Weissleder, 2001). The "NIR window" identifies the range of wavelengths that can be used for deepest penetrating through mammalian tissues. Bacteriophytochrome absorption peaks fall into the "NIR window".

FIG. 4 illustrates protein domain architecture (top panel) as well as spectral and enzymatic properties (bottom panel) of the BphG protein used for protein engineering. Top panel: *R. sphaeroides* BphG (PAS-GAF-PHY-GGDEF) is a derivative of BphG1 (PAS-GAF-PHY-GGDEF-EAL) lacking the EAL domain (Tarutina et al., 2006). BphG converts two guanosine triphosphate (GTP) molecules into cyclic dimeric GMP (c-di-GMP) by means of a diguanylate cyclase activity of the GGDEF domain (Ryjenkov et al., 2005). Bottom panel, left: Spectral properties of BphG (same as in FIG. 2). Bottom panel, right: Synthesis of c-di-GMP by *R. sphaeroides* in vitro, in the dark (grey line) and in the light (black line).

FIG. 5A is a schematic depiction of the *R. sphaeroides* BphG protein comprising the photoreceptor (PAS-GAF-PHY) and output (GGDEF) modules. The BphG protein is depicted as a parallel homodimer. FIG. 5B is a 3D model of the BphG protein based on the 3D structure 3c2w for the phototreceptor module and 3icl for the output domain (3D structures from Protein Data Bank, PDB, rcsb.org/pdb). The dashed line represents approximate position in the α-helices extending from the photoreceptor domain for fusion with a heterologous homodimeric output module. An arrow indicates rotation of an output domain as a potential outcome of light-induced conformational changes in BphG. FIG. 5C depicts a 3D model of the homodimeric adenylyl cyclase domains of protein CyaB1 from *Nostoc* sp. (modeled based upon the PDB structure 1wc5). The output module of *R. sphaeroides* BphG, the diguanylyl cyclase GGDEF domain was replaced with a distantly related adenylyl cyclase (ACyc) domain from *Nostoc* sp. CyaB1 resulting in the photoactivated adenylyl cyclase. FIG. 5D is a schematic representation of the protein domain architecture (GAF-PAS-ACyc) of *Nostoc* sp. CyaB1 depicted as a homodimer.

Figure 6:
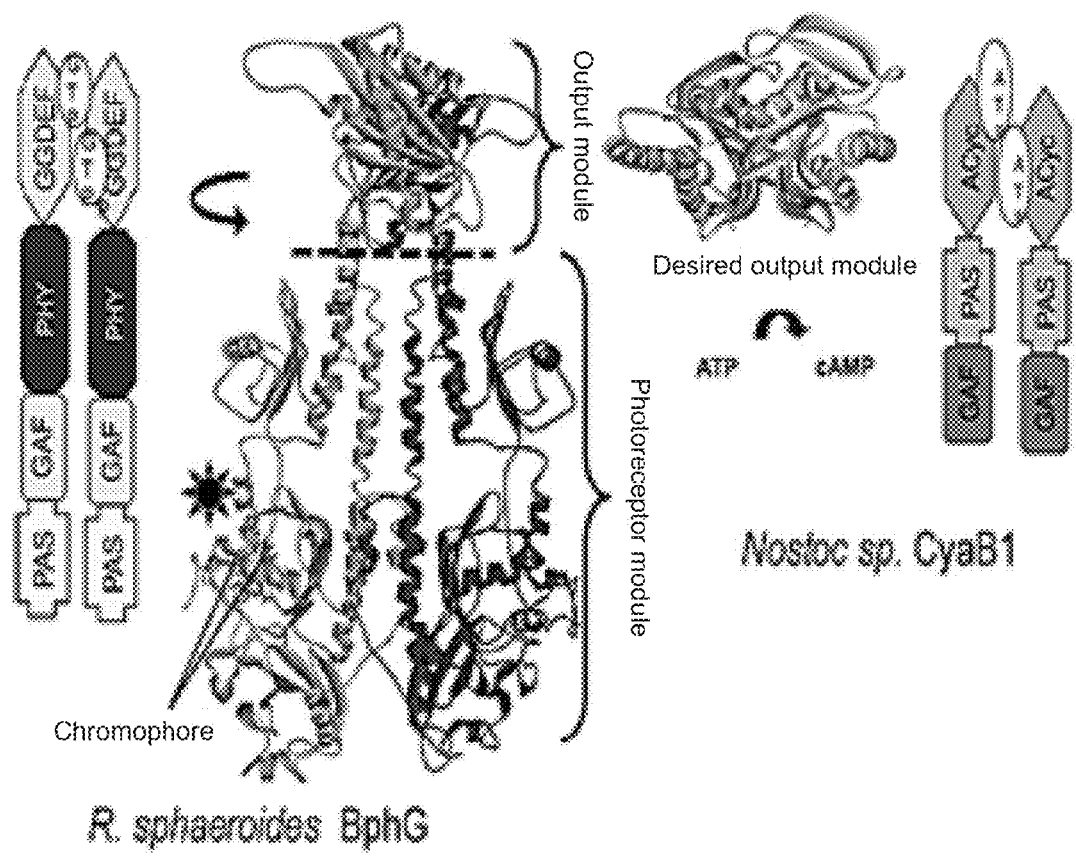
FIG. 6 illustrates the use of *E. coli* as a test organism to screen a DNA library of fusion protein constructs for adenylyl cyclase activity. A library of fusion proteins encoded by the "chimeric AC (adenylyl cyclase) genes" is expressed (e.g., from a $P_{BAD}$ promoter) in the *E. coli* strain having a cya gene deletion, which does not naturally produce cAMP. If the fusion protein generates cAMP, it enables expression of the (CRP-cAMP)-dependent lacZYA operon, which results in blue colonies on XGal indicator plates. In the absence of cAMP, the colonies are colorless. By comparing the color of colonies grown in the light (650-nm LED panel) and in the dark, one can identify light-activated and light-inactivated versions of adenylyl cyclases. The colonies appearing blue in the light and colorless (or less blue colored) in the dark contain candidate light-activated adenylyl cyclases. The colonies appearing colorless in the light and blue in the dark contain candidate light-inactivated adenylyl cyclases.
Figure 6:
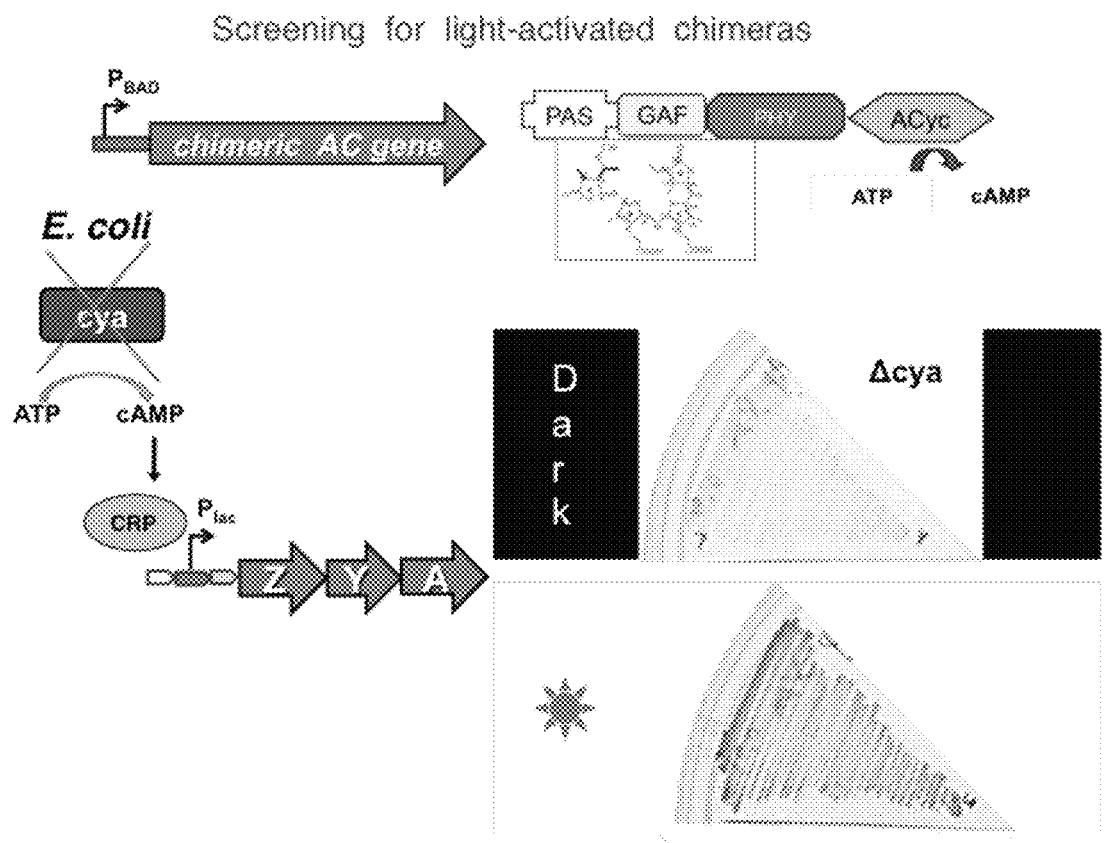

FIG. 6 illustrates the use of *E. coli* as a test organism to screen a library of fusion protein constructs for adenylyl cyclase activity. A library of fusion proteins encoded by the "chimeric AC (adenylyl cyclase) genes" is expressed (from a $P_{BAD}$ promoter) in the *E. coli* strain having a cya gene deletion, which does not naturally produce cAMP. If the fusion protein generates cAMP, it enables expression of the (CRP-cAMP-dependent) lacZYA operon, which results in blue colonies on XGal indicator plates. In the absence of cAMP, the colonies are colorless. By comparing the color of colonies grown in the light (650-nm LED panel) and in the dark, one can identify light-activated and light-inactivated versions of adenylyl cyclases. The colonies appearing blue in the light and colorless (or less blue colored) in the dark contain candidate light-activated adenylyl cyclases.

FIG. 7 illustrates XGal indicator plates containing representative *E. coli* clones, each having a gene encoding a different (numbered) fusion adenylyl cyclase protein construct, grown either in the dark (left panel) or in the light (right panel). Blue color indicates how each clone responds to light. The white arrowhead points to the clone containing a light-activated adenylyl cyclase (SEQ ID NO:6); the black arrowhead points to one of the light-inactivated adenylyl cyclases SEQ ID NO:1).

FIG. 8 shows images of *E. coli* clones containing selected light-activated [(#17, #25)] SEQ ID NO:6, SEQ ID NO:10) and light-inactivated SEQ ID NO:1 fusion adenylyl cyclase proteins grown in the dark and light, along with adenylyl cyclase activities measured using purified proteins under light and dark conditions.

FIG. 9 provides protein sequences near fusion points of selected engineered adenylyl cyclase fusions between the photoreceptor module of BphG and adenylyl cyclase (ACyc domain) of CyaB1. Photoresponses in *E. coli* of the fusion proteins were expressed at two levels of expression: low (5 µM isopropyl-beta-D-thiogalactopyranoside, (IPTG)) and high (50 µM IPTG). β-galactosidase expression (judged by the intensity of blue color) is dependent on intracellular cAMP levels. A, light-activated (higher β-galactosidase expression in the light versus dark); I, light-inactivated (higher β-galactosidase expression in the dark versus light); +, light-independent activity; –, no activity (in the dark or light). It is emphasized that protein fusions containing approximately one helical turn (+/–3-4 amino acids, aa) longer or shorter linkers had the same type of light-responsiveness, e.g. light-activated SEQ ID NO:6; SEQ ID NO:2 ([#17] SEQ ID NO:6+4 aa); SEQ ID NO:10 (SEQ ID NO:6–4 aa); SEQ ID NO:9 (SEQ ID NO:6–3 aa).

Key to the invention is the discovery of the parameters for choosing linkers which will allow for the creation of far-red/NIR light activated nucleotidyl cyclases as described in the invention. As discussed herein, functional fusion proteins can be achieved by decreasing or increasing the lengths and amino acid sequences in the linker to achieve a linker that forms an alpha helix, in particular one that is of a length that allows for complete alpha helical turns. As discussed elsewhere herein, each turn of the alpha helix is about 3.6 aa, so linkers that differ from each other from approximately 3-4 amino acids which are predicted to form complete turns should result in light-activated fusion proteins. Indeed, the active fusions as provided in FIG. 9, FIG. 12, FIGS. 21, and 22 illustrates this principle. Specifically, as an example, in FIG. 9, a linker of no or 1 amino acids (see, e.g., SEQ ID NO:8 and 9) provides for light activated activity when the adenyl cyclase domain is joined to a phytochrome domain. The next active fusion protein was achieved with a linker of four amino acids which are predicted to form alpha helix, see, e.g., SEQ ID NO:6 (linker is RAEL). After that, inactive fusions are found until a linker of eight amino acids which are predicted to form alpha helix was used (see, e.g., SEQ ID NO:2, linker is RAELARLR. In FIGS. 21 and 22, additional linkers which conform to this pattern were found, e.g., These linkers include RAEL (SEQ ID NO:39), RAELA (SEQ ID NO:40), RAE (SEQ ID NO:41), RAELARLR (SEQ ID NO:42), RAELARLRA (SEQ ID NO:43), RAELARL-RHYD (SEQ ID NO:44); RAELARLRAELA (SEQ ID NO:45).

Accordingly, it can be seen that the invention includes alpha helical linkers that comprise or consist essentially of an amino acid sequence which is capable of forming one or more complete alpha helical turns. The number of alpha helical turns that the linker is capable of forming is at least one, at least two, at least three, at least four, at least five, at least six, at least seven or more. Since the number of amino acids that comprise a complete alpha helical turn is not an integer, it is predicted that the number of amino acids for one complete turn will vary between 3 and 5 residues, or between 3 and 4 residues, and multiples thereof. Thus, linkers of 3-5 amino acids form active fusions (SEQ ID NO:39, SEQ ID NO:40, SEQ ID NO:41) and are predicted to form one helical turn; linkers of 7-9 amino acids form active fusions (SEQ ID NO:42, SEQ ID NO:43) and are predicted to form two helical turns; and linkers of 11-13 amino acids (SEQ ID NO:44, SEQ ID NO:45) are predicted to form three helical turns. The principles on linkers illustrated herein are also applicable to linkers forming four helical turns, five helical turns, six helical turns, seven helical turns or more.

One of skill in the art can easily determine appropriate linkers which are capable of forming alpha helix. The art of protein structure (secondary structure) prediction of the three dimensional structure from its amino acid sequence is quite well developed, particularly for well-ordered structures such as an alpha helix. The art shows that amino acid content of a given sequence can predict a helical region(s), and that particular amino acids tend to form an α helix. This art is quite mature. See, e.g., Kotelchuck, The Influence Of Short-Range Interactions On Protein Conformation, Ii. A Model For Predicting The A-Helical Regions Of Proteins, *Proc Natl Acad Sci* USA. 1969 January; 62(1): 14-21. Regions richer in alanine (A), glutamic acid (E), leucine (L), and methionine (M) and poorer in proline (P), glycine (G), tyrosine (Y), and serine (S) tend to form an α helix. Methods to predict secondary structure include statistical methods (Chou-Fasman method), nearest neighbor method, neural network method, among others. See, e.g., "Current Topics in Computational Molecular Biology, edited by Tao Jiang, Ying Xu, and Michael Zhang, MIT Press, 2002. Accordingly, while literal sequence provided by Applicant is useful for the present invention, one of skill can easily substitute one or more of the amino acid residues provided with another residue which is also predicted to contribute to alpha helix formation. As known in the art, not every residue present in the linkers of the present invention must be an amino acid that is particularly favorable for forming alpha helix. Rather, an amino acid sequence for a linker may be chosen in accordance with techniques known in the art for forming a primary sequence that will be predicted to form an alpha helix. FIG. 10 illustrates an overview of principles elucidated herein. The photosensory module of a bacteriophytochrome is shown schematically in the lower left with a modeled heterologous active module shown above. In the center of the figure, a modeled photosensory module is shown with the active module symbolized by a "homodimeric head." On the right, a generic modeled active module is illustrated above a list of examples of modules that can be used to engineer NIRLAHPs, e.g., kinases, proteases, transcription factors, nucleases, etc.

To make a chimeric (fusion) protein hereof, one skilled in the art applying the principles taught herein can (1) pick a protein having an activity desired to be controlled by NIR light, that is active in a homodimeric form as two fused monomers, to supply the output module of the fusion protein that is capable of performing the desired activity; (2) provide a photosensory module comprising a bacteriophytochrome, such as that of the BphG protein of *Rhodobacter sphaeroides*; (3) determine possible fusion sites of the output module and receptor module by matching distances between fusion sites on the output module and the receptor module by lengthening and/or shortening the α-helix linkers of the output and/or photoreceptor module until their fusion sites correspond in space; (4) screen the constructs for light and dark activity; (5) upon identifying active constructs, find additional active constructs by making constructs with α-helical linkers 3-4 amino acids longer or shorter than those of the identified active constructs and screening them for activity; (6) further optimize the performance of the constructs by mutagenesis of either or both of the photosensory and active modules to find fusions that perform better, i.e., low activity in the dark and high activity in the light, or vice versa.

EXAMPLES

The near-infrared light-activated diguanylyl cyclase from *R. sphaeroides*, designated BphG, converts two GTP molecules into cyclic dimeric GMP (c-di-GMP) (Tarutina et al., 2006). The dark, Pr, form of BphG absorbs maximally at 712 nm resulting in the red-shifted, Pfr, form (FIG. 4, lower left panel), whose diguanylyl cyclase activity is approximately 10-fold higher compared to the activity of the Pr form (FIG. 4, right panel). To our knowledge, the photoactivation ratio in BphG is the highest among bacteriophytochromes for which such a ratio was measured. This makes BphG particularly attractive for protein engineering. The Pfr form of BphG can be brought back to the ground (dark, Pr) state by irradiation at 750-780 nm (maximum 760 nm, FIG. 4, left panel), which instantly turns the diguanylyl cyclase activity off (Tarutina et al., 2006).

Conformational changes following photon absorption result in the rotation or other movement type in the photosensory module that is transmitted as torque through the α-helixes extending from the PHY domain of the photoreceptor to the output domain of the photoactivated monomer (FIG. 5B). This motion brings two output domains into an active homodimeric state (Yang et al., 2008; Yang et al., 2009). The photosensory module of bacteriophytochromes is capable of activating diverse homodimeric outputs. A two-tiered test of this model was performed. First, we replaced the diguanylyl cyclase GGDEF domain of BphG with a distantly related (~15% sequence identity) bacterial adenylyl cyclase (ACyc) domain such that the structural relatedness (Pei and Grishin, 2001; Sinha and Sprang, 2006) would increase the chance of a successful domain swap as shown in FIG. 5. Next, we focused on optimizing performance of the photoactivated adenylyl cyclase and constructing a near-infrared light-activated guanylyl cyclase using engineering principles developed in this work to construct a photoactivated homodimeric caspase-3 whose structure is completely unrelated to GGDEF.

We engineered several light-activated fusion proteins that differed from each other by approximately one or two α-helical turns, showing that positioning of the output domains in the same phase of the helix is important for light-dependent activity. Extensive mutagenesis of one of these fusions resulted in an adenylyl cyclase with a six-fold photodynamic range. Additional mutagenesis produced an enzyme with a more stable photoactivated state. When expressed in cholinergic neurons in *Caenorhabditis elegans*, the engineered adenylyl cyclase controlled worm behavior in a light-dependent manner.

Example 1. Engineering and Optimizing Near-Infrared Light-Activated Adenylyl and Guanylyl Cyclases Engineering a First NIR Light-Activated Adenylyl Cyclase:

For selecting photoactivated adenylyl cyclases, we constructed a cya deletion mutant, *E. coli* BL21 cya. This strain is devoid of its native adenylyl cyclase (cya mutation) and, therefore, produces white colonies on XGal indicator plates. Plasmid pBphO expressing the *R. sphaeroides* heme oxygenase, bphO1, which makes biliverdin IXα is introduced in this strain.

We constructed a structural model of the BphG homodimer based upon the most closely related protein structures available in the Protein Data Bank (PDB), i.e., 3c2w for the (PAS-GAF-PHY) photosensory module and 3icl for the GGDEF domain (FIG. 5B) (Kuzin et al., 2009). As a source of the ACyc domain we chose an extensively biochemically characterized cyanobacterial adenylyl cyclase CyaB1. An important consideration for choosing CyaB1 was that its ACyc domains are known to spontaneously dimerize and form homodimers with significant cyclase activity (even in the absence of the regulatory domains) (Bruder et al., 2005). Therefore, once the two ACyc domains are brought in proximity, they were expected to form an active enzyme. The ACyc domain dimer of CyaB1 was modeled based upon the PDB structure 1wc5. See FIG. 5C.

Based on the analysis of distances between the C-termini of the α-helices in the PAS-GAF-PHY homodimer and the N-termini of the ACyc homodimer, an approximate fusion point is chosen (FIG. 9, MAQRTRAERKEVT [SEQ ID NO:8] A library of PAS-GAF-PHY fusions to the ACyc domain of *Nostoc* sp. CyaB1 was constructed using one fixed site in the ACyc domain (FIG. 9) and variable (by a single amino acid) lengths of the α-helixes extending from the PHY domain of the photosensory module of BphG. These fusions were expressed in *E. coli* BL21 cya from an IPTG-inducible promoter.

The fusions were plated in the dark with no IPTG, and subsequently screened on a medium containing low and high levels of IPTG, in the absence (foil-wrapped plates) or presence of far-red (650 nm) light provided by LED panels. A set of the fusions with variable length linkers is shown in FIG. 9, where proteins are designated RlaC (red light-activated adenylyl cyclase). We identified four classes of fusion proteins; (a) constitutively active (e.g., RlaC28), (b) constitutively inactive (or nonfunctional, e.g., RlaC15), (c) light-inactivated (e.g., RlaC18), and the desired class of (d) light-activated fusions (e.g., RlaC29, 17, 22, and 25). Analysis of these fusions revealed several important findings. First, we learned that a starting point for creating photoactivated fusions should be based on approximately the same distance (in three-dimensional space) between the helices extending from the PHY domains and between N-termini of the output domains. These distances are derived from structural models (or crystal structures). Second, photoactivated fusion proteins can be obtained at different boundaries of the output domains (however, not all). Therefore, multiple fusion sites should be tested to identify optimal fusions. Importantly, our data are consistent with the signaling helix rotation mechanism of bacteriophytochrome photoactivation. In accord with this mechanism, fusions differing by a complete α-helical turn (i.e., approximately 3.6 aa) position output domains in the same phase of the helix, and thus α-helices differing in length by 3 or 4 amino acids (aa) should have enzymatic activities that respond to light in a similar manner. This is exactly what we observed. For example, all photoactive forms shown in FIG. 9 differ from each other by 3 or 4 aa, i.e., close to a helical turn: RlaC29=RlaC17+4 aa; RlaC25=RlaC17−4 aa, and RlaC22=RlaC17−3 aa (FIG. 9).

First-generation near-infrared light-activated adenylyl cyclases shown in FIG. 9 show useful photoactivation ratios (~5.5-fold for RlaC25, according to the in vitro activity measurements (FIGS. 7 and 8C). To improve the photoactivation ratios and decrease adenylyl cyclase activity in the dark, error-prone PCR-based mutagenesis using the full-length rlaC25 gene as a template (at the mutation frequency of 3-4 mutations per gene) can be undertaken.

Substrate specificity in class III nucleotidyl cyclases depends on just a few residues (Winger et al., 2008). We have verified this hypothesis by converting the blue-light-activated adenylyl cyclase, BlaC, into a guanylyl cyclase, BlgC (Ryu et al., 2010) using as few as three mutations.

The RlaC and RlgC derivatives are purified and characterized in vitro using methods described by us earlier (Tarutina et al., 2006; Barends et al., 2009; Ryu et al., 2010). The sequences of these mutants are analyzed to elucidate the underlying causes of lower dark activity and higher photoactivation ratios.

Engineering a Second NIR Light-Activated Adenylyl Cyclase (IlaC=RlaC):

We constructed a near-infrared light activated adenylyl cyclase, IlaC, which can control cAMP-dependent processes in live animals. FIG. 18 shows the selection strategy used for isolating IlaC22 R509W mutants with decreased dark AC activities. A library of mutant IlaC22 R509W genes was generated by error-prone PCR (mutation frequency of 3-4 mutations per gene) and cloned in plasmid pET-ilaC22 R509W to replace the IlaC22 R509W gene. *E. coli* BL21 [DE3] cya (pT7-ho1-1) transformed with the library of mutants was grown at 30° C., in the dark, on LB plates supplemented ampicillin (100 μg/mL), kanamycin (50 μg/mL) and IPTG (100 μM). Colonies containing original pET-ilaC22 R509W produce blue colonies under these conditions. White colonies were picked and subsequently retested in the presence or absence of light at low (10 μM) and high (100 μM) IPTG concentrations. Irradiation was provided to by All-red LED Grow Light panel 225 (30.5× 30.5 cm, LED Wholesalers, Calif.). Mutants that produced white colonies in the dark at 100 μM IPTG but blue colonies in the light at 10 μM IPTG were analyzed further. This screen led to identification of the triple mutant, IlaC22 k27 (arrowhead at the bottom of the Figure).

When expressed in cholinergic neurons of a roundworm *Caenorhabditis elegans*, IlaC affected worm behavior in a light-dependent manner. We engineered a series of photoactivated adenylyl cyclases (AC) (FIG. 11) designated IlaC (NIRW light-activated AC) by fusing a photosensory module from the *Rhodobacter sphaeroides* bacteriophytochrome DGC, BphG1 (Tarutina et al., 2006; Ryu and Gomelsky, 2014), to an AC domain from the *Nostoc* sp. CyaB1 protein (Kanacher et al., 2002; FIG. 11), which, like all bacterial type III ACs, works as a homodimer (Sinha and Sprang, 2006). We chose to make IlaCs because cyclic AMP (cAMP) is an important second messenger involved in regulation of diverse biological processes (Sinha and Spring, 2006; Linder, 2006). The ability to manipulate cAMP levels in specific cells or tissues in live animals is of significant interest in biomedical research.

Components of the NIRW Light-Activated AC.

For the photosensory module of the NIRW light-activated AC, we chose the PASGAF-PHY module from BphG1 from *R. sphaeroides*, where PAS, GAF and PHY (Phytochrome) are protein domain names (Pfam database). The truncated derivative of BphG1, BphG, where the PAS-GAF-PHY module is linked to a GGDEF domain, functions as a light-activated DGC (Tarutina et al., 2006) (FIG. 11). BphG was particularly attractive because (i) absorption maxima of its dark (Pr) and lit (Pfr) forms, 712 and 756 nm, respectively, lie within the NIRW, and (ii) its DGC activity is activated by light by approximately 11-fold, the largest photodynamic range (fold-activation) among bacteriophytochromes for which such ratio has been quantified (Ryu and Gomelsky, 2014).

For the output AC domain, we looked for a protein (i) whose AC activity is confined to the AC domains, i.e., where regulatory domains are not required for basal activity, and (ii) whose AC activity in the dark can be detected in a bacterial screening system.

CyaB1 from *Nostoc* sp. fit these requirements (Kanacher et al. 2002). The native CyaB1 protein has the following domain architecture, GAFGAF-PAS-PAS-AC (where AC domain is responsible for AC activity (FIG. 11). The C-terminal AC domain of CyaB1 untangled from the regulatory domains possesses some AC activity (Kanacher et al., 2002).

To monitor cAMP synthesis, we used *Escherichia coli* BL21[DE3] cya which lacks the endogenous AC, Cya. In this strain, expression of the chromosomal lacZ gene encoding (3-galactosidase is low because of the absence of activation by the cAMP-responsive protein, CRP, also known as catabolite activator protein (Busby and Ebright, 1999). BL21[DE3] cya produces white colonies on agar containing 5-bromo-4-chloro-3-indolyl-β-Dgalactopyranoside (X-Gal) (Ryu and Gomelsky, 2014). The C-terminal AC domain of CyaB1 (amino acids [aa2] 585-857) restores lacZ expression thus generating blue colonies. To endow this bacterial system with the ability to synthesize biliverdin IXα, we introduced the cyanobacterial heme oxygenase gene ho1 (Gambetta and Lagarias 2001), whose product converts heme synthesized by *E. coli* into biliverdin IXα.

Engineering a NIRW Light-Activated AC.

We synthesized the DNA fragment encoding the AC domain of CyaB1 (aa 585-857) and fused it to aa 526 in the unstructured (loop) region of the GGDEF domain of BphG. Leu585 of CyaB1 is also in the loop region, 8 aa upstream of the first structural element, β-strand, of the AC domain (FIG. 11 and FIG. 17).

FIG. 17 shows structural models of BphG and the AC domain of CyaB1. Protein modeling was performed by J. Siltberg-Liberles (Ryu et al., 2014). The parallel dimer of the phytochrome domains was constructed using two PDB structures, combined in several steps. First, a parallel dimer was built using 3C2W (Yang et al., 2008) as a template. Second, a monomer based using 4GW9 (Bellini and Papiz, 2012) as a template was built in order to model the extended C-terminal α-helix from the PHY domain. In order to extend the aligned region of the C-terminal α-helix so that it could be modeled, the sequence was anchored to 4GW9 by including the anchoring sequence fragment 'YEQF-SSQVHASMQPVLITDAEGRIL' from 4GW9. This allowed us to model the region that is critical for the estimating the distance between the extended α-helices that lead to the output domains despite low sequence identity. Third, the extended monomers were trimmed of the anchoring segment and superimposed onto the parallel dimer. Finally, the parallel dimer was modeled based on the combined template from the first three steps. This multistep modeling procedure was required to model the region important for the estimating the distance between the extended α-helices that connect PHY and AC domains. Steps 1, 3, and 4 were modeled using Swiss Model project mode, while the second step was built using the beta version of the next Swiss Model (Arnold et al., 2006). The dimer of GGDEF was constructed using 4H54 (Zahringer et al., 2013) as a template. The dimer of AC domains was constructed using 3R5G (Topal et al., 2012) as a template. Both dimers of the output domains were built using the beta version of Swiss Model (Bordoli et al., 2006).

The unstructured linkers were meant to prevent potential steric interference between the fusion partners. In accord with this intent, the chimeric protein, IlaC6, namely IAAE-MAQRTRAELARLRHYDPLTGILANLGEDALM-VGERKEVT [SEQ ID NO:14], possessed AC activity, yet this activity was nonresponsive to light (FIG. 12 and FIG. 17). Next, we determined the minimal AC domain size that retained enzymatic activity in the BphG-CyaB1 fusions.

We fixed the fusion point in BphG at aa 526 and progressively shortened the AC domain, from Leu585 to Glu594 of CyaB1, where Glu594 is in the predicted β-strand of the AC domain (FIG. 12). All fusions in this series, IlaC 10-13, proved to be enzymatically active and nonresponsive to light (FIG. 12). The sequences of the IlaC 10-13 fusions are provided below:

IlaC10:
[SEQ ID NO: 15]
IAAEMAQRTRAELARLRHYDPLTGILANGEDALMVGERKEVT

IlaC11:
[SEQ ID NO: 16]
IAAEMAQRTRAELARLRHYDPLTGILANEDALMVGERKEVT

IlaC12:
[SEQ ID NO: 17]
IAAEMAQRTRAELARLRHYDPLTGILANALMVGERKEVT

IlaC13:
[SEQ ID NO: 18]
IAAEMAQRTRAELARLRHYDPLTGILANERKEVT

In the next round of engineering, the AC domain border was fixed at Glu594 but the unstructured region of the GGDEF domain and the α-helical linker extending from the PHY domain were subject to shortening. The fusion to Arg507 of BphG (IlaC30) IAAEMAQRERKEVT [SEQ ID NO:30] and fusions containing shorter BphG fragments (IlaC 26, 27, 31) had no AC activity (FIGS. 12 and 13) likely because of the steric hindrance between the fusion components (FIG. 11), thus the engineering space was limited to aa 508-526 of BphG. The sequences of the IlaC 26, 27 and 31 fusions are provided below:

IlaC26: IAAEMAQERKEVT [SEQ ID NO:31]
IlaC27: IAAEMAERKEVT [SEQ ID NO:32]
IlaC31: IAAEMERKEVT [SEQ ID NO:33].
IlaC15: IAAEMAQRTRAERKEVT [SEQ ID NO:27] was also inactive One of the fusions in this region, IlaC 18 produced a protein whose AC activity was higher in the dark than in the light, i.e., light-inactivated AC (FIGS. 12 and 13). This result showed that light induces conformational changes that are sufficient to misalign the enzymatically productive AC homodimer. The sequence of IlaC18 is provided below:

IlaC18:
[SEQ ID NO: 20]
IAAEMAQRTRAELARLRHYDERKEVT.

Notably, light-inactivated fusions were also obtained at other fusion points, e.g., IlaC5 (FIG. 11). The sequence of IlaC5 is provided below:
IlaC5: IAAEMAQRTRAELARLRHYDMVGERKEVT [SEQ ID NO:19].

Four fusions, IlaC29 (Arg516), IlaC17 (Leu512), IlaC22 (Arg509), IlaC25 (Thr508) produced the desired, photoactivated enzymes. The AC activity of these fusions differed from each other as judged by colony color on X-Gal agar at two different isopropyl-1-thio-β-D-galactopyranoside (IPTG2) concentrations used to regulate IlaC expression levels (FIG. 13). The sequences of IlaC29, IlaC 17, IlaC22 and IlaC25 are set forth below:

IlaC29:
[SEQ ID NO: 21]
IAAEMAQRTRAELARLRERKEVT.

IlaC17:
[SEQ ID NO: 25]
IAAEMAQRTRAELERKEVT.

IlaC22:
[SEQ ID NO: 28]
IAAEMAQRTRERKEVT.

IlaC25:
[SEQ ID NO: 29]
IAAEMAQRTERKEVT.

Three photoactivated cyclases, IlaC17, IlaC22 and IlaC25, as well as one photoinactivated cyclase, IlaC18, were overexpressed as C-terminal His6-fusions and purified. The AC activity of IlaC18 was decreased by 3-fold upon irradiation with 700-nm light (FIG. 14), whereas the activities of IlaC17 and IlaC25 were increased by light by approximately 2-fold (FIG. 14). In agreement with the colony phenotypes, the basal AC activity of IlaC17 was higher than the activities of IlaC25 or IlaC22. The AC activity of IlaC22 in vitro was below detection (FIG. 14).

IlaC28, IlaC24, IlaC23 and IlaC20 were also active. Their sequences are set forth below:

IlaC28:
[SEQ ID NO: 22]
IAAEMAQRTRAELARLERKEVT.

IlaC24:
[SEQ ID NO: 23]
IAAEMAQRTRAELARERKEVT.

IlaC23:
[SEQ ID NO: 24]
IAAEMAQRTRAELAERKEVT.

IlaC20:
[SEQ ID NO: 26]
IAAEMAQRTRAEERKEVT.

Improving Photodynamic Range of the Photoactivated ACs.

Since the photodynamic range of the first-generation NIRW light-activated ACs were significantly lower than the photodynamic range of BphG, we intended to improve this parameter by random PCR-based mutagenesis. Here, we focused on IlaC22 as a template because of its low dark activity. In the light, IlaC22 produced blue colonies only when expressed at high, 50 µM, IPTG concentration. We screened the library of the PCR-mutagenized IlaC22 gene for blue colony appearance at low, 10 µM, IPTG concentration. After screening approximately $10^5$ mutant clones, we found mutants with significantly increased AC activity. The best one had an R509W (BphG numbering) substitution, right at the junction between the PHY and AC domains (FIG. 12).

The photodynamic range of AC activity of the purified IlaC22 R509W was approximately 4-fold (FIG. 14). To further improve the photodynamic range, we mutagenized the ilaC22 R509W gene at high mutation frequency. Our primary goal was to decrease the dark AC activity of IlaC22 R509W. We therefore searched for white colonies at high, 100 µM, IPTG, in the dark. The strategy used in this screen is illustrated in FIG. 18. After screening of >$10^5$ mutant clones, we identified a derivative, IlaC22 k27, that had significantly lower activity in the dark but only slightly lower activity in the light, compared to IlaC22 R509W (FIG. 14), which resulted in the photodynamic range of 6-fold. IlaC22 k27 was found to contain three new mutations, compared to IlaC22 R509W, two of which were in the BphG photosensory module (L164M, Q371H) and one in the AC domain (Q670R of CyaB1).

The protein sequences of IlaC22 k27 are provided below. Four mutations distinguishing IlaC22 k27 from IlaC22 are shown in boldface in normal font (R209W) and boldface larger font. Y259 mutated in and IlaC22 k27 Y259F is show in boldface and smaller font. The sequence derived from BphG is shown in brown; the sequence derived from CyaB1 is shown in italics, the C-terminal His6-tag at the end of the sequence is shown in black normal size font.

[SEQ ID NO: 34]
MARGCLMTISGGTFDPSICEMEPIATPGAIQPHGALMTARADSGRVAHAS

VNLGEILGLPAASVLGAPIGEVIGRVNEILLREARRSGSETPETIGSFRR

-continued

SDGQLLHLHAFQSGDYMCLDIEPVRDEDGRLPPGARQSVIETFSSAMTQV

ELCELAVHGLQLVMGYDRVMAYRFGADGHGEVIAERRRQDLEPYLGLHYP

ASDIPQIARALYLRQRVGAIADACYRPVPLLGHPELDDGKPLDLTHSSLR

SVSPVHLDYMQNMNTAASLTIGLADGDRLWGMLVCHNTTPRIAGPEWRAA

AGMIGQVVSLLLSRLGEVENAAETLARQSTLSTLVERLSTGDTLAAAFVA

ADQLILDLVGASAAVVRLAGHELHFGRTPPVDAMQKVLDSLGRPSPLEVL

SLDDVTLRHPELPELLAAGSGILLLPLTSGDGDLIAWFRPEHVQTITWGG

NPAEHGTWNPATQRMRPRASFDAWKETVTGRSLPWTSAERNCARELGEAI

AAEMAQRT*WERKEVTVLFSDIRGYTTLTENLGAAEVVSLLNQYFETMVEA*

*VFNYEGTLDKFIGDALMAVFGAPLPLTENHAWQAVRSALDMRQRLKEFNQ*

*RRIIQAQPQIKIGIGISSGEVVSGNIGSHKRMDYTVIGDGVNLSSRLETV*

*TKEYGCDHLSEFTYQLCSDRIRVRQLDKIRVKGKHQAVNIYELISDRSTP*

*LDDNTQEFLFHYHNGRTAYLVRDFTQAIACFNSAKHIRPTDQAVNIHLER*

*AYNYQQTPPPPQWDGVWTIFTK*HHHHHH.

FIG. 19 illustrates identification of residues involved in slowing the dark thermal recovery of IlaC. Shown is alignment of the *R. sphaeroides* BphG bacteriophytochrome (SEQ. ID NO:34) and the *Arabidopsis thaliana* phytochrome PhyB. Residues of PhyB affecting its photocycle and conserved in BphG are highlighted in dark gray. Mutations of PhyB that extend the lit (Pfr) state of PhyB are shown in light gray. The *Arabidopsis thaliana* PhyB amino acid sequence is publicly available on Genbank, identified as NCBI Reference Sequence: NM_127435.3.

Since the photodynamic range of IlaC22 k27 was within 2-fold of the photodynamic range of the BphG, we did not attempt to increase it further. Instead, we focused on modifying another important parameter, i.e., stability of the photoactivated state.

Extending Lifetime of the Light-Activated State of an AC.

Following photoactivation, bacteriophytochromes in the lit (Pfr) state spontaneously return to the ground, dark (Pr), state via thermal reversion (Rockwell and Lagarias, 2006). The half-life of IlaC22 k27 in the Pfr state is 46±3 s (FIG. 14A). A relatively short half-life is desirable for optogenetic applications that require short pulses of cAMP, whereas applications involving sustained light-induced increases in cAMP levels will benefit from enzymes with more stable lit state.

To increase lifetime of the lit state of IlaC22 k27, we relied on success in extending this parameter in the *Arabidopsis thaliana* phytochrome PhyB (Adam et al., 2011; Zhang et al., 2013). Four residues in the proximity of the chromophore involved in controlling dark recovery of PhyB are conserved in BphG (FIG. 19). We introduced in IlaC22 k27 the same mutations as those that prolonged the half-life of PhyB.

Three mutations (R205A, G450E, and R468A) resulted in the loss of AC activity and were discarded (FIG. 15B). The fourth mutant, IlaC22 k27 Y259F, was purified and characterized in vitro. Its absorption maxima were slightly shifted compared to IlaC22 k27, i.e., Pr (713 nm) and Pfr (755 nm) (FIG. 15C), and the half-life of thermal reversion was significantly (by 4.3-fold), increased to 197±9 s, compared to IlaC22 k27 (FIG. 15A).

The higher stability of the lit state of IlaC22 k27 Y259F was expected to allow its use in the pulsed light regiments, which may decrease such negative effects of constant irradiation as tissue heating. To test this possibility, we compared the effect of IlaC22 k27 and IlaC22 k27 Y259F on the cAMP-CRP-dependent lacZ gene expression in E. coli (FIG. 20).

FIG. 20 shows effects of IlaC k27 and IlaC k27 Y259F on cAMP-CRP-dependent lacZ gene expression in E. coli. Strain BL21[DE3] cya (pT7-ho1-1) containing either pET-ilaCK27 or pET-ilaC k27 Y259F were grown in culture tubes on a shaking platform at 30° C. in LB supplemented with ampicillin (50 μg/mL) and kanamycin (50 μg/mL). When optical densities of the cultures reached $A_{600}$ 1.5, IPTG (1 mM, final concentration) was added to induce IlaC gene expression. Irradiation was provided to by All-red LED Grow Light panel. Tubes containing "dark" samples were wrapped in aluminum foil to avoid light exposure. Samples were withdrawn at the indicated time points (0.5, 1 and 3 h) post-induction for determination of β-galactosidase activities, which was measured by the Miller method (Sambrook et al., 1989). (A), IlaC k27; (B), IlaC k27 Y259F. A, B, constant irradiation; C, D, pulsed irradiation (30 s light, 90 s dark). Black or dark-grey bars, dark; light gray bars, light. Error bars show standard deviation derived from three independent experiments. The β-galactosidase measurements were performed by A. I. Lyuksyutova (Ryu et al., 2014).

While both ACs showed similar increases in lacZ expression in constant light, compared to the dark, when pulsed light (30 s light, 90 s dark) was used, the IlaC22 k27 Y259F mutant outperformed IlaC22 k27 (FIG. 20), as expected.

Example 2. Engineering a Near-Infrared Light-Activated Executioner Caspase

Executioner caspases are terminal apoptosis-inducing proteases. They catalyze cleavage of essential cellular proteins thus irreversibly leading to apoptosis (reviewed in Crawford & Wells, 2011). Photoactivated executioner caspases can thus be used to induce specific spatiotemporal apoptosis to study molecular and cellular topics in animal development or disease. Caspase-3 functions as homodimer (reviewed in Mackenzie & Clay, 2008). In order to gain proteolytic activity, procaspase-3 undergoes proteolytic activation carried out by the upstream initiator caspases. However, Clark et al. constructed a noncleavable mutant D9A D28A D175A (designated D3A). An additional mutation, V266E, makes procaspase-3 active without proteolytic processing. The V266E mutant protein has a 60-fold higher enzymatic activity compared to the procaspase-3 D3A (which is inactive), and approximately ⅓ of the activity of the fully processed (active) caspase-3 (Pop et al., 2003; Walters et al., 2009). Since the procaspase-3 D3A V266E homodimer is intrinsically active, a distorted homodimer interface in the dark can be engineered, and restored by the light-induced helix rotation. This is conceptually identical to the task of engineering NIR light activated adenylyl cyclase.

The screening system developed by Hayashi et al. (Hayashi et al., 2009) for high throughput screening of DNA libraries in Saccharomyces cerevisiae is used for screening of photoactivated procaspase-3 fusions. In this system, the (pro)caspase-3 activity is monitored in yeast using a blue/white colony screening based on the level of expression of the lacZ reporter. Expression of the lacZ reporter gene is dependent on the transcription activator whose cellular localization is determined by the caspase-3 activity. If caspase-3 is active, the transcription activator is cleaved off from its transmembrane domain, released from the membrane, moves to the nucleus and activates lacZ expression. If caspase activity is low, the transcription activator remains as a fusion with the transmembrane domain and therefore is sequestered to the membrane and unable to activate lacZ expression. Active caspase-3 releases the transcription activator by cleaving at its recognition site, DEVD, engineered between the transmembrane and activator modules of the transcription activator. In addition to lacZ, LEU2 (providing for leucine prototrophy when expressed in the S. cerevisiae LEU2 mutant) can also be used as a reporter of caspase-3 activity.

The procaspase-3 D3A V266E is fused to the photoreceptor PAS-GAF-PHY module of BphG and expressed in S. cerevisiae under the galactose-inducible GAL1 promoter, in a dose-dependent fashion with the varying galactose concentration in the media. The photoactivated caspase-3 derivatives are identified as blue color colonies on X-gal leucine-deficient media on plates grow in the light. Responsiveness of such colonies to light is subsequently investigated upon comparing colony color in the light and in the dark as shown for photoactivated adenylyl cyclase (FIG. 7). The yeast strain also expresses the R. sphaeroides heme oxygenase BphO1 that provides biliverdin to the chimeric caspase.

First-generation photoactivated caspases identified are subjected to iterative mutagenesis and screening to identify those with the lowest dark activities and the highest photoactivation ratios (similar to those described for the photoactivated adenylyl cyclase). The optimized photoactivated procaspase-3 D3A V266E proteins are purified via the C-terminal His6-tag (Pop et al., 2003), and assayed in vitro using commercially available fluorescence- or chromogenic assays of caspase-3 activity.

Example 3. NIRW Light-Activated Control of Caenorhabditis elegans Behavior

To test performance of the NIRW light-activated AC oin an animal model, we expressed IlaC k27 in cholinergic neurons of the roundworm C. elegans.
Materials and Methods
Microbiological Methods.

Escherichia coli BL21[DE3] cya lacking endogenous adenylyl cylase CyaA (26) and containing two plasmids, pT7-ho1-1 (25) that express the Synechocystis sp. heme oxygenase ho1 (Gambetta & Lagarias, 2001) and pETilaC# (expressing IlaC proteins) were used for IlaC screening. Strains were grown at 30° C. in LB supplemented with X-gal (40 μg/mL), ampicillin (50 μg/mL) and kanamycin (25 μg/mL). IPTG was added for induction of IlaC proteins. For light-sensitive experiments, Petri dishes were placed onto All-red (660 nm) LED2 Grow Light panels 225 (30.5×30.5 cm, LED Wholesalers, Calif.). Light irradiance was approximately 0.2 mW cm$^{-2}$. For growth in the dark, Petri dishes were wrapped in aluminum foil.

Recombinant DNA Techniques.

The DNA fragment of bphG1 gene (RSP4191) encoding the photosensory PAS-GAF-PHY module was amplified by PCR from the R. sphaeroides 2.4.1 genome. The DNA fragment of cyaB1 from Nostoc (formerly Anabaena) sp. PCC 7120 was synthesized by BioBasics, Inc. with the codon usage optimized for R. sphaeroides. Two fragments were joined by fusion PCR using GoTaq (Promega) and subsequently cloned into the XbaI and HindIII sites of pET23a(+) (Invitrogen) to yield a series of plasmids, pETilaC#. Each of these plasmids encodes a unique BphG-CyaB1::His6 fusion protein. Site-directed mutagenesis was performed using QuickChange kit (Stratagene). Error-prone PCR mutagenesis was carried out using GeneMorph II Random mutagenesis kit (Agilent Technologies).

The Punc-17:ilaC plasmid, pNQ149, was constructed using the MultiSite Gateway Three-Fragment Vector Construction Kit (Invitrogen). The ilaC22 k27 cDNA PCR product was first cloned into the pdonr221 entry vector by BP cloning. pNQ149 was then constructed by using the LR reaction to combine the unc-17 promoter (obtained from the Promoeome library in the pdonrP4-P1r entry vector), the ilaC22 k27 cDNA in the pdonr221 entry vector, and the unc-54 3'UTR in the pdonrP2R-P3 entry vector.

Protein Purification and AC Assays.

The IlaC proteins were purified as C-terminal His6-tagged fusions using Ni-NTA affinity chromatography (Novagen). AC assays were performed using freshly purified proteins at room temperature, essentially as described earlier (Ryjenkov et al. 2005).

Spectroscopy.

Electronic absorption spectra were recorded with a UV-1601 PC UV-visible spectrophotometer (Shimadzu) at room temperature. Protein solution (100 µL) in a 10-mm light path quartz cuvette was irradiated by 1-W (700 nm) LED directly in the spectrophotometer from the top of the cuvette.

Bioinformatics.

Multiple sequence alignments were generated using MUSCLE (Edgar RC 2004). Secondary structures predictions were performed using Jpred3 server (Bordoli and Schwede, 2006). Modeling of 3D structures was done using Swiss Model (Barber and Barton 2008) project mode and beta version of the next Swiss Model (Benkert and Schwede 2011).

Protein Overexpression and Purification.

The IlaC proteins were purified as C-terminal His6-tagged fusions using Ni-NTA affinity chromatography according to specifications of the manufacturer (Novagen). Protein purification was performed under green light. The overnight cultures of E. coli BL21[DE3] expressing the IlaC::His6 proteins were grown in LB supplemented with appropriate antibiotics at room temperature to A600 0.7. Protein expression was induced with IPTG at final concentration of 0.5 mM, and the cultures were incubated with shaking at 250 rpm at 18° C. for additional 20 h. Bacteria were collected by centrifugation at 4,000×g for 10 min, washed and resuspended in the binding buffer (50 mM sodium phosphate [pH 8.0], 300 mM NaCl) supplemented with 0.2 mM phenylmethylsulfonyl fluoride and 10 mM imidazole. Cells were disrupted using a French pressure cell, and cell debris was removed by centrifugation at 35,000×g for 45 min at 4° C. Three milliliters (bed volume) of Ni-NTA resin (Novagen) preequilibrated with the binding buffer were added to the soluble cell extract derived from a 1 L culture and agitated for 1 h at 4° C. The mix was loaded onto a column, and the resin was washed with 200 mL of column binding buffer. Fractions were eluted with 12 mL of binding buffer containing 250 mM imidazole. The proteins were either used immediately or stored at −80° C. in 20% v/v glycerol (final concentration). Protein concentrations were measured using a Bradford protein assay kit (BioRad) with bovine serum albumin as the protein standard. Proteins were analyzed using SDS-PAGE.

AC Assays.

A standard reaction mixture (300 µl) contained 5 mM enzyme in the assay buffer (50 mM Tris-HCl [pH 8.0], 10% glycerol, 10 mM MgCl2, 0.5 mM EDTA). The protein was irradiated either with dim green light or far-red light emitted from a 1-W (700 nm) LED at the approximate irradiance of 0.2 mW cm-2. The reaction was started by the addition of ATP.

Aliquots (50 µL) were withdrawn at different time points and immediately boiled for 5 min. The precipitated protein was removed by centrifugation at 15,000×g for 5 min. The supernatant was filtered through a 0.22-µm pore size filter (MicroSolv, N.J.). cAMP levels were analyzed by reversed-phase high-pressure liquid chromatography (HPLC) as described earlier (Ryjenkov et al. 2005).

C. elegans Cultivation and Transgenesis.

Animals were cultivated on nematode growth medium (NGM) agar and were fed E. coli DA837 derived from strain OP50 (Davis et al. 1995). All experiments were performed onhermaphrodites. The following strains were used in this study: N2 (Bristol), NQ719 qnEx386[Punc-17:iLac; Pmyo-2:mCherry], NQ721 qnEx388[Punc-17:iLac; Pmyo-2:mCherry]. Transgenic animals were created by microinjection (Stinchcomb et al. 1985) using a Leica DMIRB inverted DIC microscope equipped with an Eppendorf Femtojet microinjection system. N2 animals were injected with 25 ng/µL of pNQ149 in combination with 5 ng/µL of pCFJ90 (Pmyo-2:mCherry) and 120 ng/µL 1 kb molecular weight ladder (New England Biolabs).

C. elegans Behavioral Assays.

Animals were grown in the dark for one generation on NGM agar seeded with DA837 bacteria. For the assays performed on agar, L4 larvae were transferred to NGM plates seeded with DA837 and grown to early adulthood overnight. Individual adult animals were transferred in the presence of green light onto an NGM plate without bacteria and left unperturbed for 15 min. Animals were observed using a Leica MZ16 stereomicroscope. During this time the animals were exposed to green light for 30 s, red light for 30 s, and green light for 30 s. Body bends were counted by the observer. Irradiation was provided by LED Color Changing Kit IP66 (LED Wholesalers, Calif.). No biliverdin IXα was added to the agar.

For the swimming assays, we followed, with minor modifications, the protocols described by Weissenberger et al. (2011). L4 larvae were transferred to NGM plates seeded with DA837 bacteria supplemented with 1 mM biliverdin hydrochloride (Sigma) and grown to early adulthood for one day.

Individual early adult animals were transferred in the presence of green light into a 10 µL drop of NGM and M9 in a 1:1 ratio supplemented with 1 mM biliverdin hydrochloride. Animals were video monitored for 2 min using a USB 2.0 monochrome camera (ImagingSource, model DMK 72AUC02), mounted on a Leica MZ16 stereomicroscope. During the 2 min recording, the animals were exposed to green light for 30 s, red light for 30 s, and green light again for 60 s. Body bend frequency was counted by observing the video recordings.

Previously, a blue-light activated AC, PACα, has been utilized in C. elegans as a tool for optogenetic manipulation of behavior. Expression of PACα in the cholinergic neurons, using the promoter for the vesicular acetylcholine transporter unc-17, followed by stimulation with blue light resulted in increased locomotory activity (Weissberger et al., 2011). However, blue light activates a C. elegans avoidance response and is toxic upon prolonged irradiation (Weissberger et al., 2011; Edwards et al. 2008), thus confounding the interpretation of the behavioral response to cAMP optogenetic manipulation. Therefore, we used IlaC for behavioral analyses in *C. elegans*.

We generated transgenic animals expressing IlaC22 k27 in cholinergic neurons using the unc-17 promoter. IlaC22 k27 transgenic animals cultivated on an agar surface and exposed to daily light from the environment were more active than wild-type animals, as evident by the frequency of their body bends (FIG. 16A).

Hyperactivity is characteristic of animals with increased activity of cAMP-dependent protein kinase A (PKA), such as mutants for the gene kin-2, which encodes for the regulatory subunit of PKA (Schade et al., 2005). To test the effect of red light, we grew wild-type and Punc-17:ilaC animals in the dark for a single generation.

Individual animals were transferred to an agar surface that did not contain food. Animals were monitored under monochromatic LED irradiation for 90 s. During this time, body bends were counted during the following light regiment: green light 0-30 s, red 31-60 s, and green 61-90 s. While control animals did not alter their locomotory activity in response to red light (FIG. 16B), Punc-17:ilaC animals performed more body bends in the presence of red light (FIG. 16B).

We also monitored the effects of AC activation in cholinergic neurons on the frequency of thrashing movements in liquid medium. Swimming animals, which were reared in the dark, were video monitored for a total of 2 min during the following light regiment: green 0-30 s, red 31-60 s, green 61-120 s. While control animals did not alter their thrashing rate in response to red light, Punc-17:ilaC animals increased their thrashing rates when exposed to red light (FIG. 16C). Interestingly, their thrashing rates significantly decreased during the second exposure to green light (FIG. 16C), due to post-stimulatory fatigue. Thus, our results indicate that the NIRW light-activated AC can be used as a tool for optogenetic manipulation of cAMP levels in animals Discussion:

Unique photochemical properties of bacteriophytochromes, i.e., (i) light absorbance in the NIRW, optimal for use in red-blooded animals; (ii) naturally available in animal cells chromophore (biliverdin IXα), and (iii) innocuous nature of NIRW light, position them as superior photoreceptors for optogenetic applications in animals (Sambrook et al., 1989). However, bacteriophytochrome engineering for optogenetic applications has been hindered by the lack of understanding of mechanisms through which light-induced conformational changes induce changes in output domains. Two most common bacteriophytochrome types, histidine kinases and DGCs, operate as homodimeric enzymes, where proper alignment of two monomeric kinase or GGDEF domains is essential for enzymatic activity. The constructed-here NIRW light-activated ACs, IlaCs showed that α-helices extending from the PAS-GAF-PHY photosensory modules are primarily responsible for alignment of the output domains (FIG. 11) and that the light-induced movements mediated by the α-helices can regulate alignment of unrelated, heterologous domains whose activity requires properly aligned homodimers. The recently solved structures of the photosensory module of the *Deinococcus* bacteriophytochrome showed that the distance between the signaling α-helices changes by as much as 30 Å in response to light (Takala et al., 2014).

We have enabled the following for future homodimeric bacteriophytochrome engineering: First, we have provided guidance for the choice of the output domains and screening schemes. For example, the ability of the AC domains of CyaB1 to spontaneously homodimerize helped us to distinguish between enzymatically active and inactive fusions (FIGS. 12 and 13). The high sensitivity of the screening system employed here was useful for detecting relatively low (2-fold) photodynamic ranges (FIG. 13). An engineering strategy that involves (i) construction of permissive fusions (involving unstructured linkers) as the first step, (ii) subsequent minimization of the output domain size, and finally, (iii) shortening (or extending) signaling α-helices, are also applicable.

We have also shown that photoactivation ratios of the first-generation light-responsive fusions can be significantly improved by extensive mutagenesis.

The energy associated with the light-induced conformational changes should be sufficient to manipulate the output domain alignment. For overly tight homodimers, monomer interactions can be weakened. Another important issue is reasonable correspondence in distances between fusion points in the signaling and output components. We estimated the distance between the α-helical residues of BphG that resulted in photoactivated fusions were in the range of 11-22 Å, while the distances the distances between the N-terminal β-strands of the catalytically inactive CyaB1 AC domain homodimer were approximately 40 Å (see FIG. 17). These distances turned out to fit nicely in the 10-40 Å spread between the α-helices of the *Deinococcus* BphP in the dark and lit states (Takala et al., 2014).

We found not one but several photoactivated IlaC fusions. Interestingly, they differed from each other by either 3-4 residues (IlaC29=IlaC17+4 aa; IlaC25=IlaC17−4 aa; IlaC22=IlaC17−3 aa) (FIG. 12), which places their AC domains roughly in the same helical phase but separated by one or two α-helical turns (1 turn=3.6 aa [Lehninger et al., 2000]) (FIG. 17). This result is consistent with the model where α-helices act as rods involved in aligning rigid output domains located at their tips. It is therefore unsurprising that the 1 or 2-aa shifts out of helical phase destroy proper domain alignment and result in the loss of light responsiveness (FIG. 12).

IlaC expressed in neurons of the roundworm *C. elegans* affected behavior in response to light. In the case of *C. elegans*, the main advantages of IlaC over blue-light activated ACs are the absence of the photoavoidance response and the lack of phototoxicity associated with prolonged exposure to blue light (Weissenberger et al., 2011; Edwards et al., 2008). However, IlaC will be most useful in applications in deep mammalian tissues inaccessible by blue light.

Our demonstration that homodimeric bacteriophytochromes are amenable to protein engineering and recent progress in structural understanding of dark-to-light conformational changes (Takala et al., 2014) enables the design of new NIRW light-activated proteins.

Since activities of many signal transduction components depend on homodimerization, including membrane receptors, cyclic nucleotide phosphodiesterases, certain protein phosphatases, proteases, nucleases, and transcription factors, we have enabled significant expansion of the optogenetic toolset involving NIRW light.

Optimized versions of the photoactivated chimeric enzymes, adenylyl- and guanylyl cyclases and procaspase-3 can be expressed under cell- or tissue-specific promoters and delivered to desired organisms via gene delivery procedures known in the art by those of ordinary skill in the art without undue experimentation.

This work has shown for the first time the engineering of a near-infrared light-activated heterologous activities based on bacteriophytochrome photoreceptor modules, revealed engineering principles applicable to a variety of homodimeric proteins, and demonstrated the utility of random mutagenesis and screening in test organisms for identifying bacteriophytochrome-based proteins with improved photoactivation ratios and low dark activities.

Example 3. Engineering Additional Near-Infrared Light-Activated Adenylyl and Guanylyl Cyclases Provided are examples of new far-red/NIR light-activated adenylyl cyclases engineered by following the methodology described herein. Specifically, the newly engineered proteins were made by fusing the components as described herein. Successful engineering of the far-red/NIR light-activated adenylyl cyclases from different bacteriophytochrome photoreceptors and different nucleotidyl cyclases verify utility of the engineering principles described herein. These examples emphasize the importance of the alpha-helical secondary structure of linkers connecting the photoreceptor and nucleotidyl cyclase domains and show that the primary sequences of the said alpha-helices may vary (Example 2, +9aa and +12aa).

IlaD Protein

IlaD-Protein Series are Made from the Following Domains:

a. the photoreceptor domain from the *Deinococcus radiodurans* bacteriophytochrome BphP (SEQ ID NO:37) [this domain is different from *Rhodobacter sphaeroides* BphG1 used in the previous Examples], b. the nucleotidyl cyclase domain from *Nostoc* sp. CyaB1 [this domain is identical to the domain used in the previous Examples], c. the linker sequence between the photoreceptor and the nucleotidyl cyclase comprising an amino acid sequence that forms an alpha helix [this linker is identical to the sequences of alpha-helical linkers described in previous Examples].

The FIG. 21) shows the subset of the engineered fusion DrBphP-CyaB1 proteins possessing far-red/NIR light activated adenylyl cyclase activities. The font for the amino acid (and numbers) correspond to the proteins shown above the sequences. Bold font, PHY domain from *Deinococcus radiodurans* BphP; regular font, alpha-helical linker; italicized font, adenylyl cyclase domain from CyaB1. Helix, predicted secondary structure of the linker; arrow, predicted β-strand. Adenylyl cyclase activities were assessed as in Ryu et al. (2014) *Proc Natl Acad Sci* USA 111:10167-72.

IlaDM-Protein Series are Made from the Following Domains:

a. the photoreceptor domain from the *Deinococcus radiodurans* bacteriophytochrome BphP (SEQ ID NO:38) [this is different from *Rhodobacter sphaeroides* BphG1 used in the previous Examples], b. the nucleotidyl cyclase domain from the *Mycobacterium tuberculosis* Rv1264 protein (sequence 2) [this is different from CyaB1 used in the previous Examples]

c. the linker sequence between the photoreceptor and the nucleotidyl cyclase domains comprising an amino acid sequence that forms an alpha helix. The linker sequences are either identical (−1aa to +8aa, figure below) or partially different (+9aa and +12aa, figure below) from the sequences of alpha-helical linkers described in the previous Examples].

The FIG. 22 shows the subset of the engineered fusion DrBphP-MtCya proteins possessing far-red/NIR light activated adenylyl cyclase activities. The amino acid fonts (and numbers) correspond to the proteins shown above the sequences. Bold font, PHY domain from *Deinococcus radiodurans* BphP; regular font, alpha-helical linker; italicized font, adenylyl cyclase domain from CyaB1; bold italicized font, AC domain from *Mycobacterium tuberculosis* Rv1264. Helix, predicted secondary structure of the linker; arrow, predicted β-strand. Adenylyl cyclase activities were assessed as in Ryu et al. (2014) *Proc Natl Acad Sci* USA 111:10167-72.

Accordingly, it can be seen that a number of alpha-helical linkers are disclosed herein, which result in light-activated fusion proteins as described herein. These linkers include RAEL (SEQ ID NO:39), RAELA (SEQ ID NO:40), RAE (SEQ ID NO:41), RAELARLR (SEQ ID NO:42), RAEL-ARLRA (SEQ ID NO:43), RAELARLRHYD (SEQ ID NO:44); RAELARLRAELA (SEQ ID NO:45).

The methods provided herein have been described in terms of specific illustrations. It will be appreciated by those of ordinary skill in the art that reagents, starting materials, and process steps and conditions can be varied without undue experimentation by substitution of equivalents thereto to achieve analogous results and produce analogous fusion proteins and DNA encoding them. All such variations are considered equivalent to those specifically illustrated herein, and are intended to be covered the claims hereof.

The invention claimed is:

1. A homodimeric fusion protein controllable by far red and/or near-infrared (NIR) light, said fusion protein comprising:
   (a) a photoreceptor domain from a bacteriophytochrome;
   (b) a heterologous nucleotidyl cyclase domain; and
   (c) a linker sequence between the C-terminal end of the bacteriophytochrome domain and the N-terminal end of the nucleotidyl cyclase domain, wherein the linker sequence is selected from the group consisting of SEQ ID NO:39, SEQ ID NO:40, SEQ ID NO:41, SEQ ID NO:42, SEQ ID NO:43, SEQ ID NO:44, and SEQ ID NO:45;
wherein said nucleotidyl cyclase domain of said homodimeric fusion protein is capable of dimerizing with another nucleotidyl cyclase domain of another of said homodimeric fusion protein when treated with far-red or NIR light, and wherein the nucleotidyl cyclase is enzymatically activated upon homodimerization.

2. The homodimeric fusion protein of claim 1, wherein the nucleotidyl cyclase is a light-activated adenylyl cyclase or a light-activated guanidyl cyclase.

3. The homodimeric fusion protein of claim 1, wherein the linker sequence is SEQ ID NO: 40.

4. The homodimeric fusion protein of claim 1, wherein said bacteriophytochrome photoreceptor domain is from the BphG1 protein from *Rhodobacter sphaeroides*.

5. A recombinant DNA molecule encoding the homodimeric fusion protein of claim 1.

6. A host organism capable of expressing the fusion protein of claim 1, which is transformed with the DNA sequence of claim 5.

7. The host organism of claim 6, which is a cultured organism selected from the group consisting of bacteria, yeast, plant, insect or mammalian cells selected or modified so as to detectably exhibit the level of activity of said expressed fusion protein controllable by the presence or absence of far red or NIR light.

8. The host organism of claim 6, which is a multicellular organism selected from the group consisting of insects, plants, and animals.

9. The host organism of claim 6, also comprising heme oxygenase introduced into the organism from outside or by transforming the organism with a heme oxygenase gene or heme oxygenase precursor gene.

10. A method for controlling an in vivo process in a host which is a living cell or organism comprising:
    (a) introducing into the cell or organism, or selected portion of the organism a DNA sequence of claim 6;
    (b) allowing said fusion protein to be expressed in said host; and
    (c) applying NIR light of a selected wavelength to the host or preventing NIR light of a selected wavelength from contacting the host; thereby modulating the process under control of NIR light.

11. The method of claim 10, wherein said process is selected from the group consisting of metabolic processes, signal transduction, cell apoptosis, cell proliferation, cell adhesion, and cell differentiation.

12. The method of claim 10, wherein said process is selected from the group consisting of cyclic AMP production, cyclic GMP production, muscle activity, neuronal activity, heart rate, and hormone production.

13. The homodimeric fusion protein of claim 1, wherein the linker sequence is selected from the group consisting of SEQ ID NO:39, SEQ ID NO:40, and SEQ ID NO:41.

14. The homodimeric fusion protein of claim 1, wherein the linker sequence is selected from the group consisting of SEQ ID NO:42 and SEQ ID NO:43.

15. The homodimeric fusion protein of claim 1, wherein the linker sequence is selected from the group consisting of SEQ ID NO:44 and SEQ ID NO:45.

* * * * *